US010761043B2

(12) United States Patent
Drndic et al.

(10) Patent No.: US 10,761,043 B2
(45) Date of Patent: Sep. 1, 2020

(54) GRAPHENE-BASED NANOPORE AND NANOSTRUCTURE DEVICES AND METHODS FOR MACROMOLECULAR ANALYSIS

(75) Inventors: Marija Drndic, Philadelphia, PA (US); Ken Healy, Cambridge, MA (US); Meni Wanunu, Chestnut Hill, MA (US); Christopher Ali Merchant, Baltimore, MD (US); Matthew Puster, Philadelphia, PA (US); Kimberly Elizabeth Venta, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 295 days.

(21) Appl. No.: 13/553,853

(22) Filed: Jul. 20, 2012

(65) Prior Publication Data
US 2013/0309776 A1    Nov. 21, 2013

Related U.S. Application Data

(60) Provisional application No. 61/510,650, filed on Jul. 22, 2011.

(51) Int. Cl.
*G01N 27/26* (2006.01)
*G01N 33/487* (2006.01)
*G01N 27/00* (2006.01)

(52) U.S. Cl.
CPC ....... *G01N 27/26* (2013.01); *G01N 33/48721* (2013.01); *Y10T 156/10* (2015.01); *Y10T 156/1056* (2015.01); *Y10T 436/143333* (2015.01)

(58) Field of Classification Search
CPC ........ G01N 33/48; G01N 27/00; G01N 27/26; G01N 33/48721; B82Y 15/00; Y10T 436/14333; Y10T 156/1056; Y10T 156/10
USPC ........... 436/94; 422/82.01; 257/253; 156/60, 156/272.2, 272.6, 252
See application file for complete search history.

(56) References Cited

U.S. PATENT DOCUMENTS 8,173,335 B2    5/2012  Drndic et al.
2009/0236609 A1*  9/2009  de Heer ................ H01L 21/321
                                                    257/77

(Continued)

FOREIGN PATENT DOCUMENTS

WO    WO 2011/046706 A1    4/2011
WO    WO 2012/005857 A1    1/2012

(Continued)

OTHER PUBLICATIONS

Aarik, J. et al., "Atomic layer deposition of TiO2 thin films from TiI4 and H2O", Appl Surf Sci Jun. 2002, 193, 277.

(Continued)

*Primary Examiner* — Rebecca M Fritchman
(74) *Attorney, Agent, or Firm* — BakerHostetler

(57) ABSTRACT

Provided are graphene-based nanopore and nanostructure devices, which devices may include an insulating layer disposed atop the graphene, which can be in a planar shape or nanostructured into a ribbon or other shapes, containing a single graphene layer or several layers. Graphene layers and nanostructures can be placed nearby horizontally or stacked vertically. Also provided are related methods of fabricating and processing such devices and also methods of using such devices in macromolecular analysis.

23 Claims, 66 Drawing Sheets

(56) References Cited

U.S. PATENT DOCUMENTS

2010/0327847 A1    12/2010    Leiber et al.
2011/0227044 A1*    9/2011    Kawanaka et al. ............. 257/29

OTHER PUBLICATIONS

Astier Y, et al. Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Branton D et al. "The potential and challenges of nanopore sequencing", Nat Biotechnol. Oct. 2008;26(10):1146-53.
Burns MA et al. "Nanopore sequencing technology: research trends and Applications", Trends Biotechnol. Dec. 2006;24(12):580-6. Epub Oct. 19, 2006.
Chen, P. et al., "Atomic Layer Deposition to Fine-Tune the Surface Properties and Diameters of Fabricated Nanopores", Nano Lett Jun. 2004,7,1333-1337.
Chen, P. et al., "Probing Single DNA Molecule Transport Using Fabricated Nanopores", Nano Lett. Oct. 2004, 4, 2293-2298.
Cho, S. et al., "Gate-tunable graphene spin valve", Appl Phys Lett 2007, 91, 123105.
Clarke J, et al. "Continuous base identification for single-molecule nanopore DNA sequencing", Nat Nanotechnol Apr. 2009;4(4):265-70. doi: 10.1038/nnano.2009.12. Epub Feb. 22, 2009.
Dekker C. "Solid-state nanopores", Nat Nanotechnol. Apr. 2007;2(4):209-15. Epub Mar. 4, 2007.
Fischbein MD et al. "Sub-10 nm device fabrication in a transmission electron microscope", Nano Lett. May 2007;7(5):1329-37. Epub Apr. 17, 2007.
Fischbein, M.D. et al., "Electron Beam Nanosculpting of Suspended Graphene Sheets" Appl Phys Lett 2008, 93, 113107.
Garaj S, et al. "Graphene as a subnanometre trans-electrode membrane", Nature. Sep. 9, 2010;467(7312):190-3. Epub Aug. 18, 2010.
Gracheva ME, et al. "Multilayered semiconductor membranes for nanopore ionic conductance modulation", ACS Nano. Nov. 25, 2008;2(11):2349-55.
Gracheva ME, et al. "p-nSemiconductor membrane for electrically tunable ion current rectification and filtering", Nano Lett. Jun. 2007;7(6):1717-22. Epub May 22, 2007.
Gu LQ, et al. "Single molecule sensing by nanopores and nanopore devices", Analyst. Mar. 2010;135(3):441-51. Epub Dec. 22, 2009.
Han MY, et al. "Energy band-gap engineering of grapheme nanoribbons", Phys Rev Lett. May 18, 2007;98(20):206805. Epub May 16, 2007.
Hashimoto A, et al. "Direct evidence for atomic defects in graphene layers", Nature. Aug. 19, 2004;430(7002):870-3.
Healy K, et al. "Solid-state nanopore technologies for nanopore-based DNA analysis", Nanomedicine (Lond). Dec. 2007;2(6):875-97.
Kasianowicz JJ, et al. "Characterization of individual polynucleotide molecules using a membrane channel", Proc Natl Acad Sci U S A. Nov. 26, 1996;93(24):13770-3.
Kim KS, et al. "Large-scale pattern growth of graphene films for stretchable transparent Electrodes", Nature. Feb. 5, 2009;457(7230):706-10. Epub Jan. 14, 2009.
Li J, et al. "DNA molecules and configurations in a solid-state nanopore microscope", Nat Mater. Sep. 2003;2(9):611-5. Epub Aug. 24, 2003.
Li J, et al. "Ion-beam sculpting at nanometre length scales", Nature. Jul. 12, 2001;412(6843):166-9.
Li X, et al. "Large-area synthesis of high-quality and uniform graphene films on copper foils", Science. Jun. 5, 2009;324(5932):1312-4. Epub May 7, 2009.
Liu H, et al. "Translocation of single-stranded DNA through single-walled carbon nanotubes", Science. Jan. 1, 2010;327(5961):64-7.
Liu Z, et al. "Open and closed edges of graphene layers", Phys Rev Lett. Jan. 9, 2009;102(1):015501. Epub Jan. 5, 2009.
Lu, et al., "In Situ Electronic Characterization of Graphene Nanoconstrictions Fabricated in a Transmission Electron Microscope," Nano Lett., 2011, 11 (12), pp. 5184-5188.
Meller, A et al., "Single molecule measurements of DNA transport through a nanopore", Electrophoresis 2002, 23, 2583-2591.
Merchant CA, et al. "DNA translocation through grapheme nanopores", Nano Lett. Aug. 11, 2010;10(8):2915-21.
Meyer JC, et al. "The structure of suspended graphene sheets", Nature. Mar. 1, 2007;446(7131):60-3.
Novoselov KS, et al. "Electric field effect in atomically thin carbon films", Science. Oct. 22, 2004;306(5696):666-9.
Novoselov KS, et al. "Room-temperature quantum Hall effect in grapheme", Science. Mar. 9, 2007;315(5817):1379. Epub Feb. 15, 2007.
Postma HW. "Rapid sequencing of individual DNA molecules in graphene nanogaps", Nano Lett. Feb. 10, 2010;10(2):420-5.
R. Wang et al. "Light-induced amphiphilic surfaces", Nature 1997, 388, 431-432.
Schneider GF, et al. "DNA translocation through grapheme nanopores", Nano Lett. Aug. 11, 2010;10(8):3163-7.
Simmons JM, et al. "Effect of ozone oxidation on single-walled carbon nanotubes", J Phys Chem B. Apr. 13, 2006;110(14):7113-8.
Siwy ZS, et al. "Engineered voltage-responsive nanopores", Chem Soc Rev. Mar. 2010;39(3):1115-32. Epub Dec. 4, 2009.
Skinner GM, et al. "Distinguishing single- and double-stranded nucleic acid molecules using solid-state nanopores", Nano Lett. Aug. 2009;9(8):2953-60.
Smeets RM, et al. "Nanobubbles in solid-state nanopores", Phys Rev Lett. Aug. 25, 2006;97(8):088101. Epub Aug. 24, 2006.
Storm AJ, et al. "Fabrication of solid-state nanopores with single-nanometre precision", Nat Mater. Aug. 2003;2(8):537-40.
Storm AJ, et al. "Translocation of double-strand DNA through a silicon oxide nanopore", Phys Rev E Stat Nonlin Soft Matter Phys. May 2005;71(5 Pt 1):051903. Epub May 6, 2005.
Varghese N, et al. "Binding of DNA nucleobases and nucleosides with grapheme", Chemphyschem. Jan. 12, 2009;10(1):206-10.
Venkatesan BM, et al. "Highly Sensitive, Mechanically Stable Nanopore Sensors for DNA Analysis", Adv Mater. Jul. 20, 2009;21(27):2771.
Venkatesan, B. M., et al. "DNA Sensing Using Nanocrystalline Surface-Enhanced Al2O3 Nanopore Sensors", Adv. Funct. Mater., Apr. 2010, 20:1266-1275.
Wang S, et al. "Wettability and surface free energy of graphene films", Langmuir. Sep. 15, 2009;25(18):11078-81.
Wanunu M, et al. "DNA translocation governed by interactions with solid-state nanopores", Biophys J. Nov. 15, 2008;95(10):4716-25. Epub Aug. 15, 2008.
Zhang Y. et al., "Formation of metal nanowires on suspended single-walled carbon nanotubes", Appl Phys Lett. Nov. 2000, 77, 3015-3017.
Zwolak M, et al. "Electronic signature of DNA nucleotides via transverse transport", Nano Lett. Mar. 2005;5(3):421-4.

\* cited by examiner

SiNx hole diameter ~ 20 nm
Graphene hole diameter ~ 3.5 nm

GRAPHENE-BASED NANOPORE AND NANOSTRUCTURE DEVICES AND METHODS FOR MACROMOLECULAR ANALYSIS

RELATED APPLICATION

The present application claims priority to U.S. patent application 61/510,650, "DNA Translocation Through Graphene Nanopores," filed Jul. 22, 2011, the entirety of which application is incorporated herein by reference for all purposes.

STATEMENT OF GOVERNMENT RIGHTS

This invention was made with government support under grant numbers HG004767 and HG006313 awarded by the National Institutes of Health, grant number DMR0832802 awarded by the National Science Foundation, and grant number W911NF-06-1-0462 awarded by the Army/Army Research Office. The government has certain rights in the invention.

TECHNICAL FIELD

The present disclosure relates to the field of nanotechnology and to the field of graphene solid-state devices.

BACKGROUND

Nanopore-bearing membranes are an emerging technology for DNA, RNA, protein (or other macromolecule) analysis; such devices are used to analyze biological molecules by observing a signal related to macromolecular passage through the nanopore. Such devices, however, suffer from signal noise, sufficient speed, and other shortcomings. Accordingly, there is a need in the art for improved nanopore devices and related methods of using such devices.

SUMMARY

In meeting the described challenges, the present disclosure first provides devices, comprising a first graphene sheet having at least one pore extending therethrough or nearby the pore, a membrane contacting the first graphene sheet, the membrane having an aperture in register with the pore of the first graphene sheet, the pore having a characteristic cross-sectional dimension in the range of from about 0.1 nm to about 100 nm. The graphene sheet itself can be in the shape of a plane, a ribbon, bow-tie or other shape.

Also disclosed are methods of analyzing a sample, comprising translocating at least a portion of a macromolecule through a pore extending through or nearby a graphene sheet; collecting a signal related to the translocation; and correlating the signal to a structural characteristic of the macromolecule.

Further provided are methods of fabricating a device, comprising disposing a graphene sheet atop a membrane having an aperture formed therethrough such that a pore extending through the graphene sheet or nearby the graphene sheet is in register with the aperture of the membrane.

Also disclosed are methods for constructing a device, comprising applying a voltage to a graphene sheet having a pore formed therethrough or nearby, the voltage being in the range of from about 10 mV to about 10 V.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

In some embodiments, the cross-sectional dimension of the aperture differs from the cross-sectional dimension of the pore by less than about 5 nm, or even by less than about 20 nm. In some embodiments, the user may seek to minimize the area of graphene that is suspended above the aperture formed an a support membrane. Without being bound to any particular theory, this may improve the signal-to-noise characteristics of a device.

The device is inserted into a polymer (PDMS) measurement cell with microfluidic channels that form reservoirs in contact with either side of the chip. A bias voltage, $V_B$, is applied between the reservoirs to drive DNA through the nanopore. (b) TEM image of a nanopore in a graphene membrane. Scale bar is 10 nm. (c) Ionic current-voltage measurement for this 10-nm graphene nanopore device in 1M KCl, pH 9.

Figure 2:
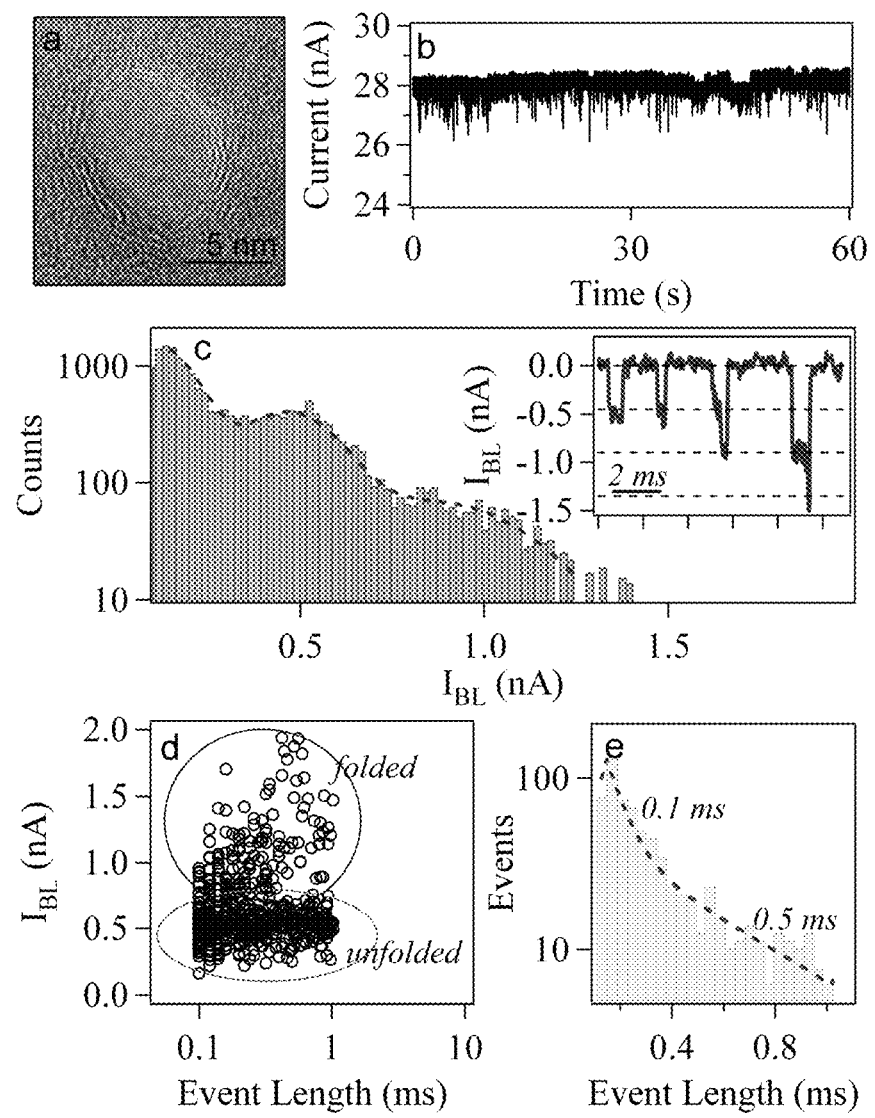

FIG. 2. DNA translocations through graphene nanopore. (a) TEM image of an ~8-nm diameter graphene nanopore. (b) Time trace (i.e., ion current vs. time) of events for nanopore device shown in (a). (c) Histogram of blocked currents for measured translocation events for the same device at $V_B$=100 mV in 1M KCl solution. Data is fit using two Gaussian functions with mean values at 0.45 and 0.90 nA. Inset displays concatenated events including some unfolded and folded events which have been observed. $I_{BL}$ values of 0.45, 0.9, and 1.35 nA are indicated with dashed black lines, indicating unfolded, singly-folded, and doubly-folded entries, respectively. (d) Scatter plot of event length vs. event depth for same device at $V_B$=100 mV. Regions of unfolded and folded events are highlighted inside the circled areas. (d) Histogram of event lengths for the same device. Data is fit (dashed red line) by a double exponential of the form $a_1 \exp(-t/\tau_1)+a_2 \exp(-t/\tau_2)$ with time constants $\tau_1=0.07$ and $\tau_2=0.5$ ms, t is the time, and $a_1$ and $a_2$ are constants.

Figure 3:
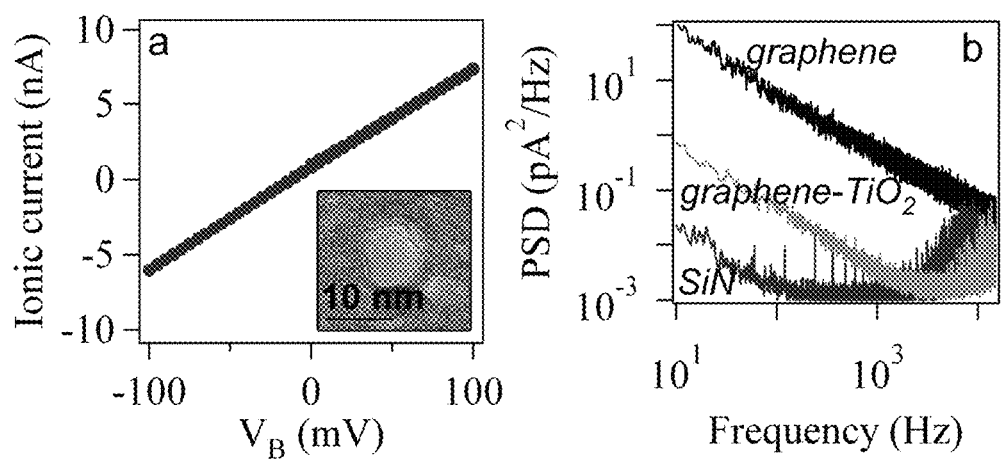

FIG. 3. Characterization of $TiO_2$-covered graphene nanopore devices. (a) Current-voltage measurement for a $TiO_2$-covered graphene nanopore. Inset is a TEM image of this 7.5-nm diameter nanopore. Scale bar is 10 nm. Ion current noise characterization: (b) Power spectral density of the pore current for an 8-nm diameter nanopore bare graphene device (black) at $V_B=100$ mV, 7.5-nm nanopore $TiO_2$-covered graphene (green) at $V_B=100$ mV, and 6-nm nm diameter silicon nitride nanopore device (blue) at $V_B=120$ mV.

Figure 4:
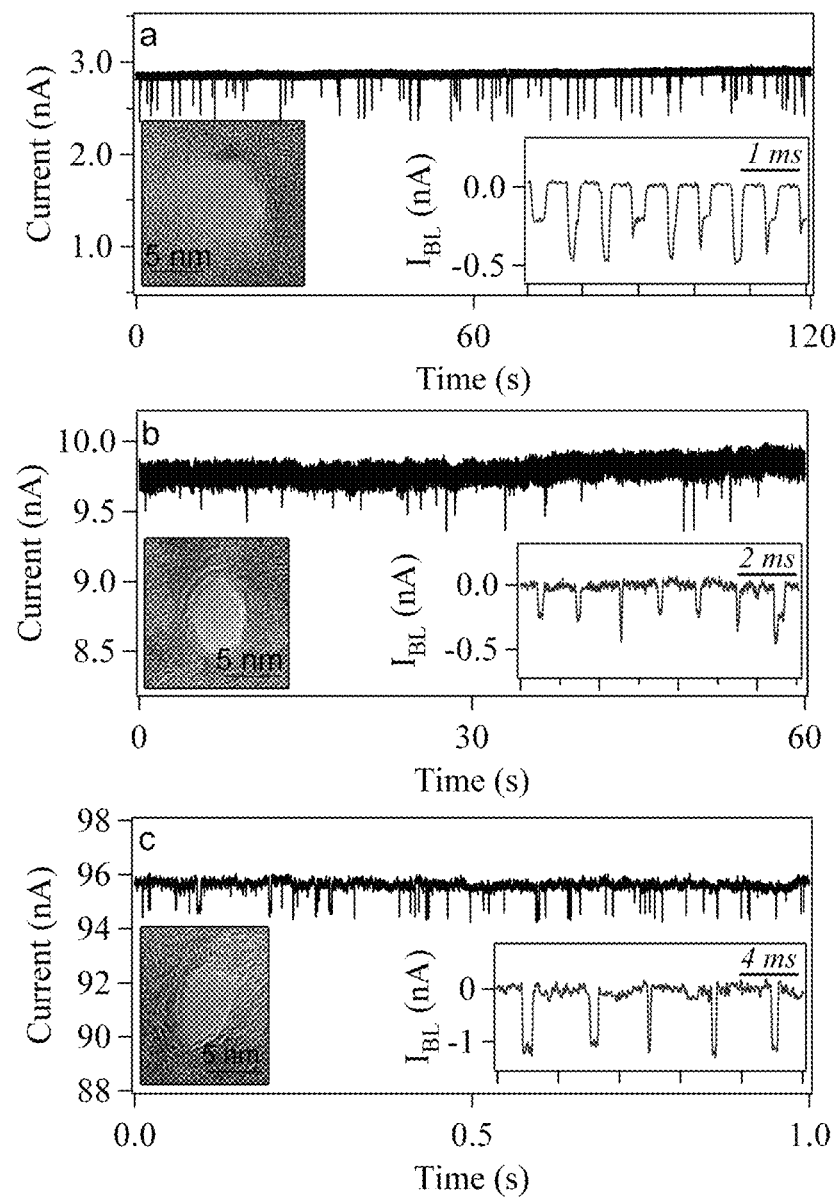

FIG. 4. DNA translocations through graphene nanopores coated with an insulating layer of 5-nm $TiO_2$. Time traces of ionic current showing DNA translocations for (a) a 7.5 nm diameter nanopore with 1 nM 15 kbp dsDNA, (b) an 8-nm diameter nanopore with 1 nM 15 kbp dsDNA, and (c) a 5.5-nm diameter nanopore with 20 nM 400 bp dsDNA. All devices were coated with 5 nm $TiO_2$ to separate the graphene surface from the salt solution. Left inset in each figure is a TEM image of the actual nanopores used. Scale bars are 5 nm. Right inset in each figure shows a concatenated sequence of sample events with the open pore current subtracted. $V_B$ for each trace is (a) 100 mV, (b) 100 mV, and (c) 150 mV.

Figure 5:
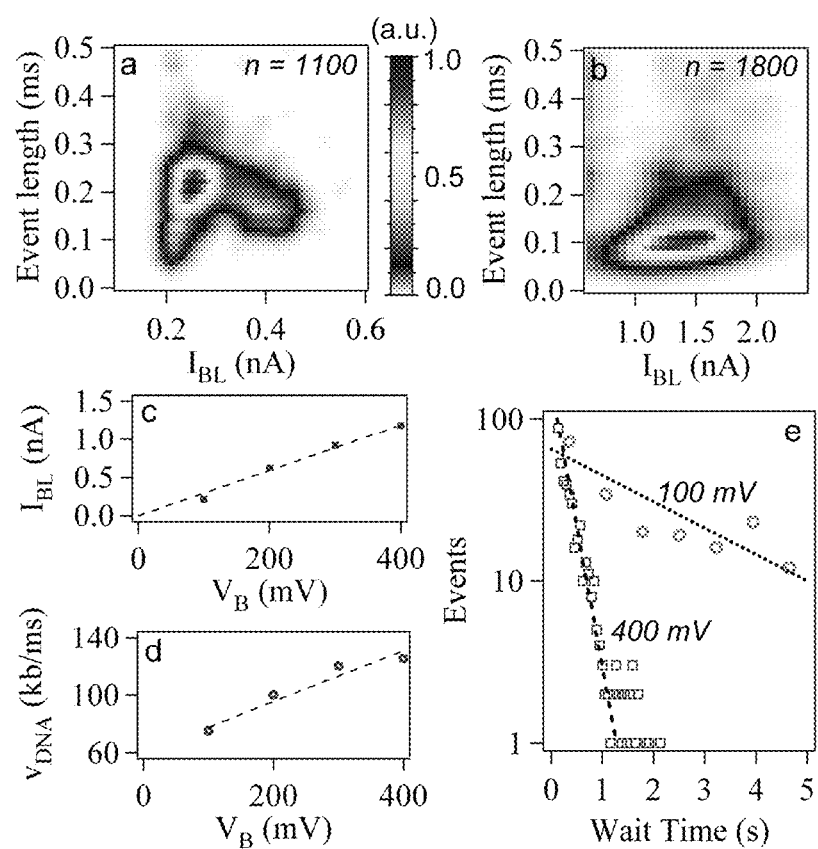

FIG. 5. Characterization of translocation events for a $TiO_2$ coated graphene nanopore device. (a) 2-D histogram of event length vs. blocked currents for an 8-nm diameter pore with 5 nm $TiO_2$ for 15 kbp dsDNA at $V_B=100$ mV. The color scale corresponds to the normalized frequency of events. (b) 2-D histogram of event lengths vs. blocked currents for same device at $V_B=400$ mV. (c) Blocked current, $I_{BL}$, as a function of $V_B$. $I_{BL}$ values (red squares) are extracted using a Gaussian fit from current histograms taken at each bias voltage. A linear fit is provided for reference (dashed black line). (d) Translocation velocity, $v_{DNA}$, as a function of $V_B$. Velocity values are computed using mean event length values at each bias voltage and DNA length. A linear fit is provided for reference (black dashed line). (e) Histogram of wait times for 250 events at $V_B=100$ mV (green circles) and 850 events at $V_B=400$ mV (blue squares). Data was fit with a Poissonian (black dashed line) of the form $\Pi(\lambda,t)=c\lambda\exp(-\lambda t)$, with capture rates $\lambda=0.3$ s$^{-1}$ for $V_B=100$ and $\lambda=4$ s$^{-1}$ for $V_B=400$ mV, and c is a constant.

Figure 6:
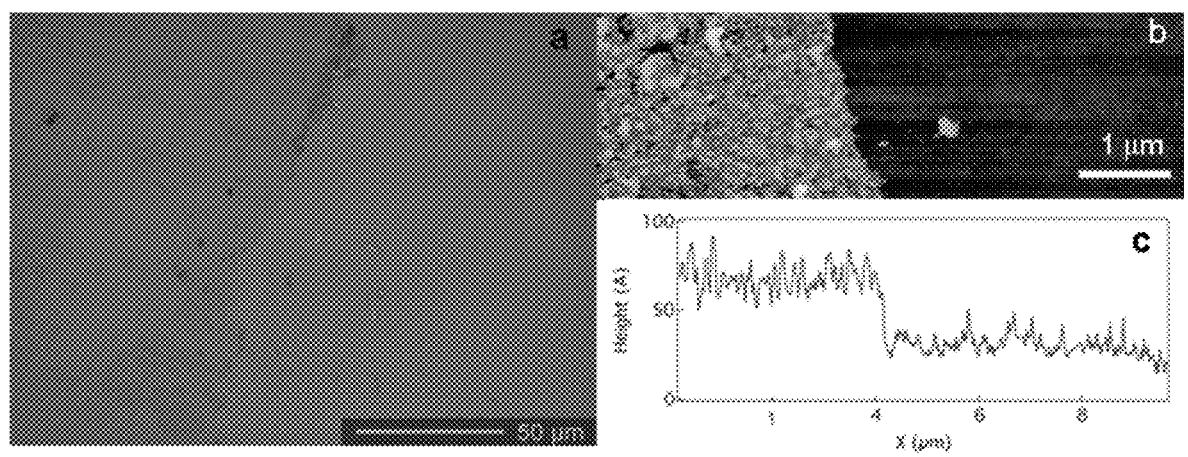

FIG. 6. (a) Optical image of a large chemical vapor deposition (CVD) graphene sheet deposited on 90-nm thick $SiO_2$ on top of Si. Growth occurs under 10 minutes of $H_2$ and $CH_4$ at 1000° C. followed by rapid cooling. Substrates for graphene growth are 1"×2" Cu foils. Foil is dissolved in 1M $FeCl_3$ solution followed by 4M HCl treatment. (b) AFM image of edge of graphene sheet. (c) Linescan through AFM image in (b). Sheet is approximately 5 nm thick (~15 layers).

Figure 7:
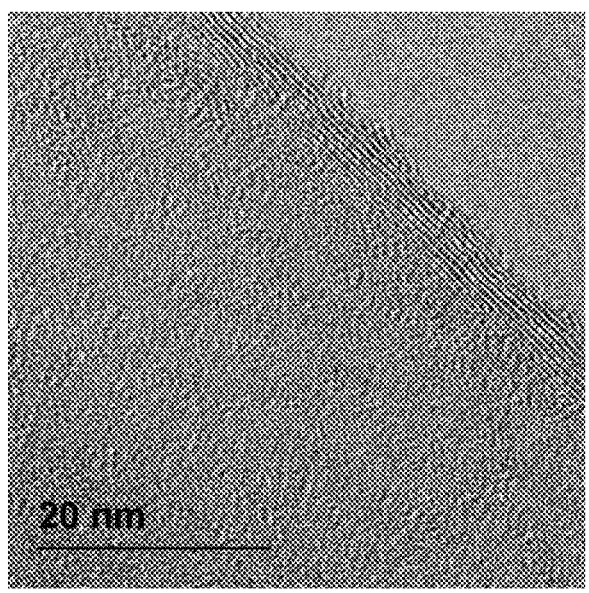

FIG. 7. TEM image of suspended CVD graphene sheet. Lines at edge indicate this particular sheet is ~8 layers thick.

Figure 8:
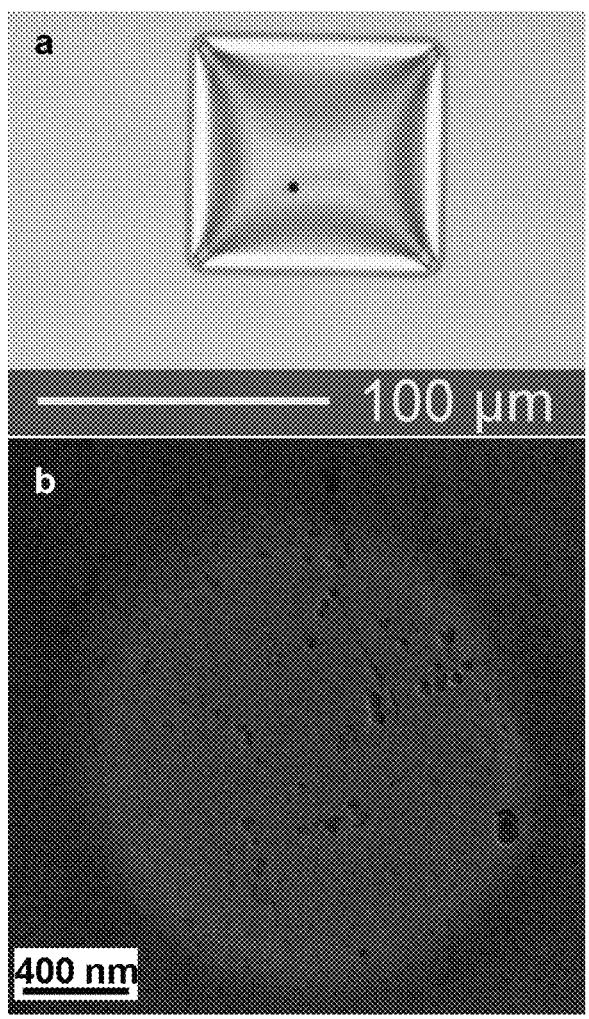

FIG. 8. (a) Optical image of silicon nitride (SiN) membrane with ~1-micron hole etched by electron-beam lithography and $SF_6$ plasma. (b) TEM image of graphene suspended over such a 1 μm hole in SiN. Dark spots are impurities on the graphene surface.

Figure 9:
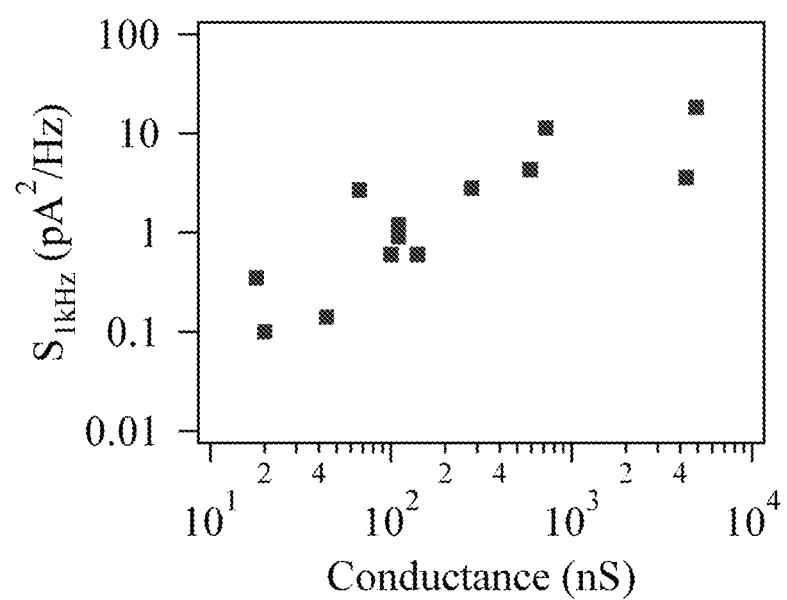

FIG. 9. Nanopore current noise at ~1 kHz as a function of open pore conductance. Each point is the median power spectral density over the range 1 to 2 kHz. Open pore conductance is computed using $V_B$ and the measured open pore current for each device.

Figure 10:
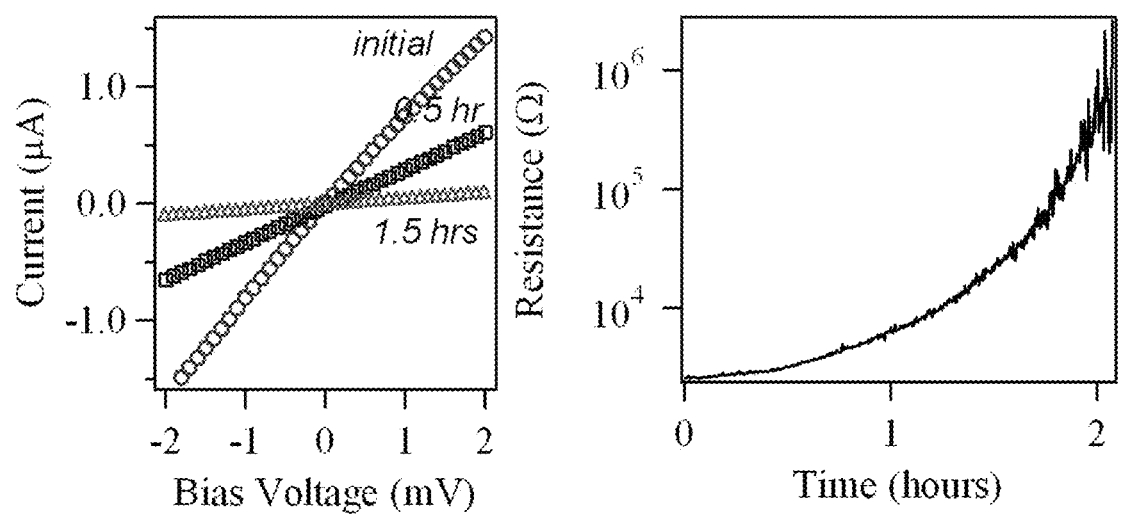

FIG. 10. In-plane electrical characterization of the graphene sheet during UV/ozone treatment. (a) Current-voltage (IV) measurement of a graphene sheet contacted by ~1 mm long Ti/Au electrodes that are separated by approximately 100 μm. Current-voltage traces are taken before any UV/ozone treatment (red circle), after 0.5 hours of treatment (blue squares) and after 1.5 hours of treatment (green triangles). (b) Resistance of the sheet is plotted as a function of time during UV/ozone treatment.

Figure 11:
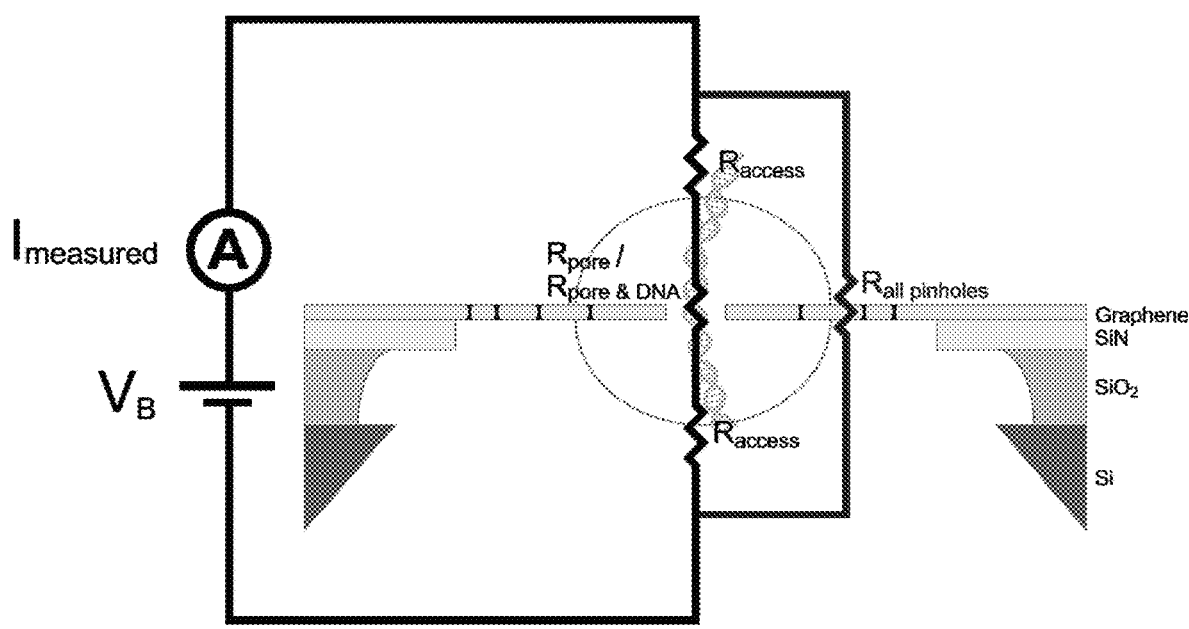

FIG. 11. Equivalent circuit for graphene nanopore devices with possible pinholes indicated in the graphene sheet, illustrating how they can contribute to the measured current. Pinholes are represented as red holes through the graphene layer and modeled as resistances in parallel with that of the nanopore. $R_{access}$, $R_{pore}$, $R_{pore\&DNA}$, $R_{all\ pinholes}$ are the access resistance, the nanopore resistance, the nanopore resistance when DNA is in the pore and the equivalent resistance of all the pinholes in graphene, respectively. The blue circle indicates the region of interest around the nanopore.

Figure 12:
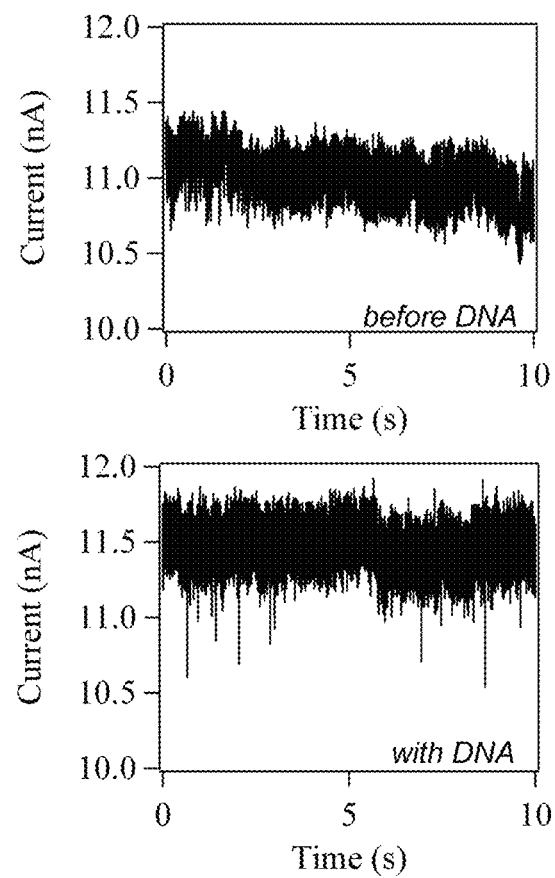

FIG. 12. Time trace of ionic current for an 8-nm diameter graphene nanopore at $V_B=200$ mV before and after the addition of DNA. Translocation events are only observed in the latter case. There is a slight change in the open pore current after the addition of DNA which is not significant and likely due to slight concentration differences between the solutions with and without DNA. DNA translocation is observed using 1 nM 15 kbp dsDNA in 1M KCl, mM Tris, pH=8.5 electrolyte solution. Current was recorded for $V_B=100$ mV, filtered at 30 kHz and sampled at 200 kHz.

Figure 13:
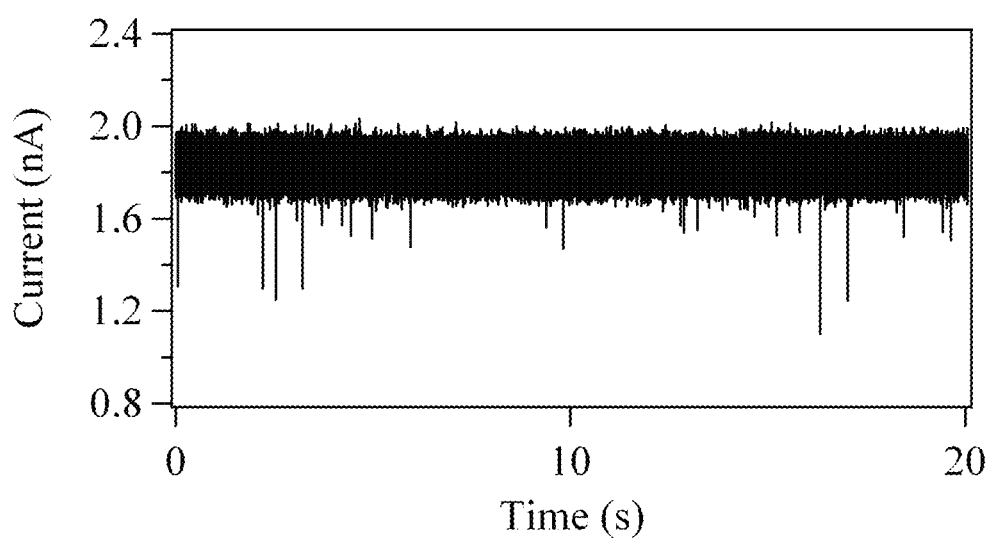

FIG. 13. Time trace of DNA translocation through a 6-nm diameter, 40 nm thick SiN nanopore for 1 nM 15 kbp dsDNA in 1M KCl, 10 mM Tris, pH=8.5 electrolyte solution. Current was recorded for $V_B=100$ mV, filtered at 30 kHz and sampled at 200 kHz.

Figure 14:
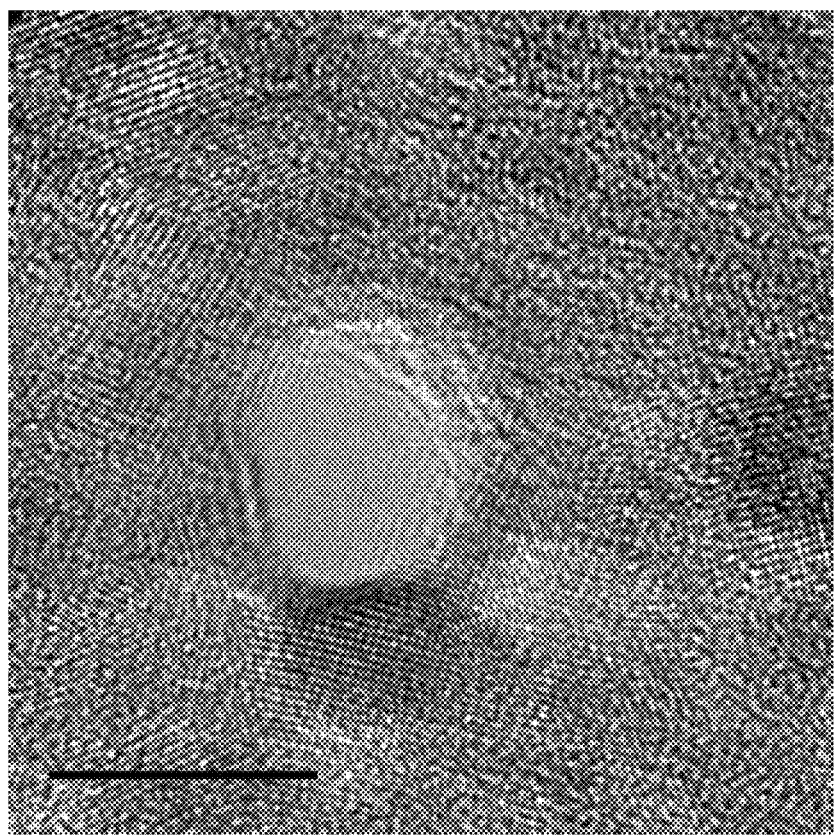

FIG. 14. TEM image of crystallized $TiO_2$ around a newly drilled nanopore ~8-nm in diameter. $TiO_2$ is deposited at 200° C. from Ti(IV) Isopropoxide and $H_2O$ in a Savannah 200 atomic layer deposition system (Cambridge Nanotech, Cambridge, Mass.). Growth rate is approximately 0.35 Å per cycle. Scale bar is 10 nm.

Figure 15:
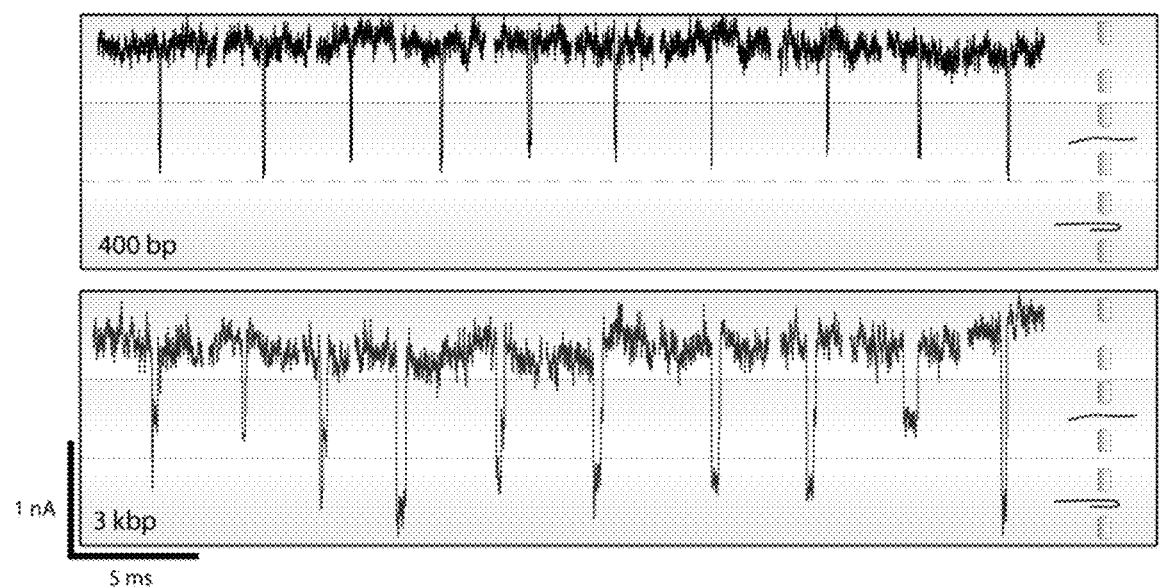

FIG. 15. Translocation events for 400 and 3000 bp dsDNA with the $TiO_2$-coated graphene nanopore shown in FIG. 4c. Top and bottom panels show data for 400 bp (same measurement presented in FIG. 4c) and 3000 bp dsDNA, respectively. While events for the 400 bp exhibit a single characteristic amplitude, for the 3000 bp DNA one may observe a significant number of events that are attributed to folded entry of the DNA The amplitude of a folded entry (1.6 nA) is ~ double the amplitude of unfolded entry (~0.8 nA), and the appearance of a large fraction of folded and unfolded translocations is in line with previous translocation measurements in silicon nitride membranes.

Figure 16:
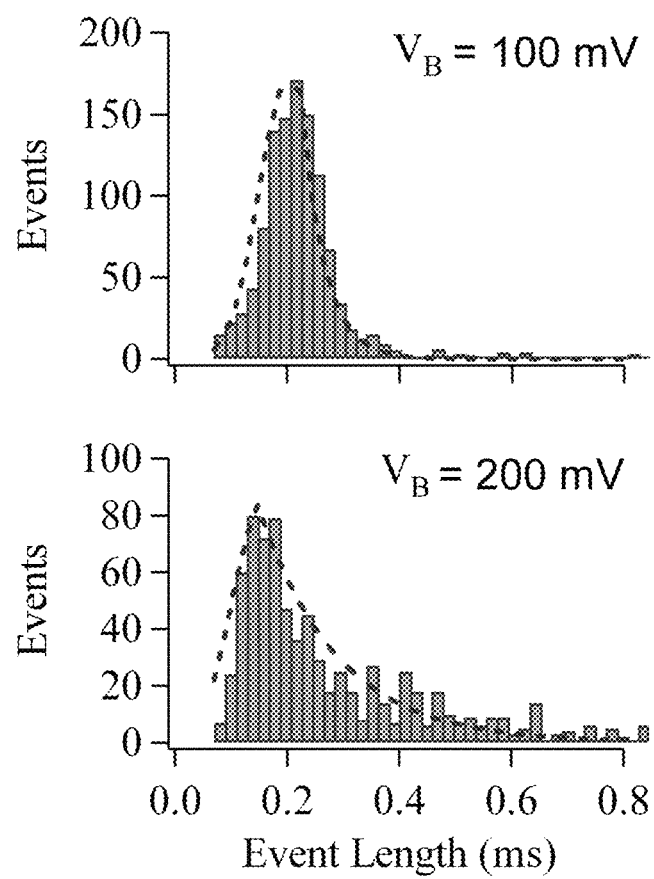

FIG. 16. Event length as a function of $V_B$. Mean event length as a function of bias voltage in FIG. 5 (c) computed by fitting (red dashed line) a Gaussian to points before the most probable value and with an exponential of the form $\exp(-t/\tau)$ to points after the most probably value.

Figure 17:
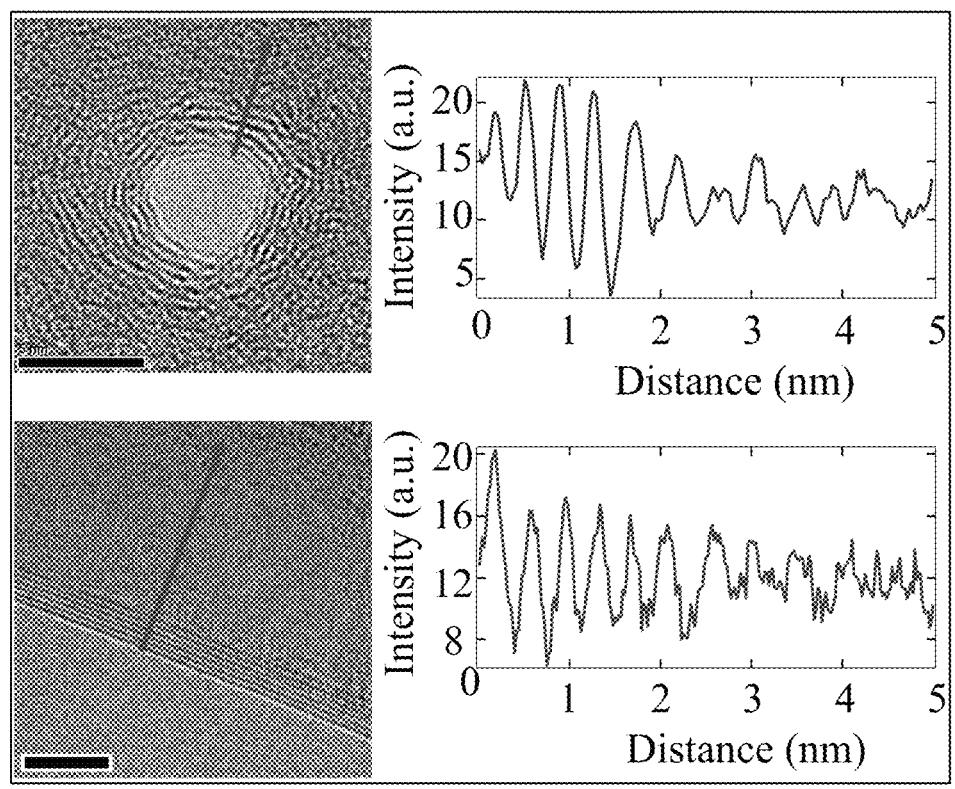

FIG. 17. TEM images of nanopore in multilayer graphene and the edge of a multilayer graphene sheet showing the structure of the edges, including linescans of intensity vs. distance along the red lines indicated. The ringlike structure of the pore bears a close resemblance to the dark lines observed at the edge of a folded graphene sheet. These ringlike structures are terraces formed in multilayer graphene. Consequently, the membrane thickness decreases from several layers thick for membrane regions away from the nanopore, down to single layer thick graphene membrane at the nanopore. Intensity cross-sections obtained from images of the folded graphene sheet and nanopore reveal an average spacing between dark lines of 0.38±0.02 and 0.39±0.02 nm, respectively. These values are equivalent within the error introduced by finite TEM resolution and are close to the interlayer distance of highly oriented pyrolitic graphite (~0.34 nm). Additionally, for nanopore drilling at room temperature inside of the TEM, it is possible that the nanopore edges may be contaminated by hydrocarbons. This results in nanopore edges that are effectively thicker than desired because the deposited contaminants form a crater-like accretion of material near the pore. If nanopores are drilled at elevated temperatures of ~300° C. or higher, this accumulation of contamination near the pore is reduced or eliminated.

Figure 18:
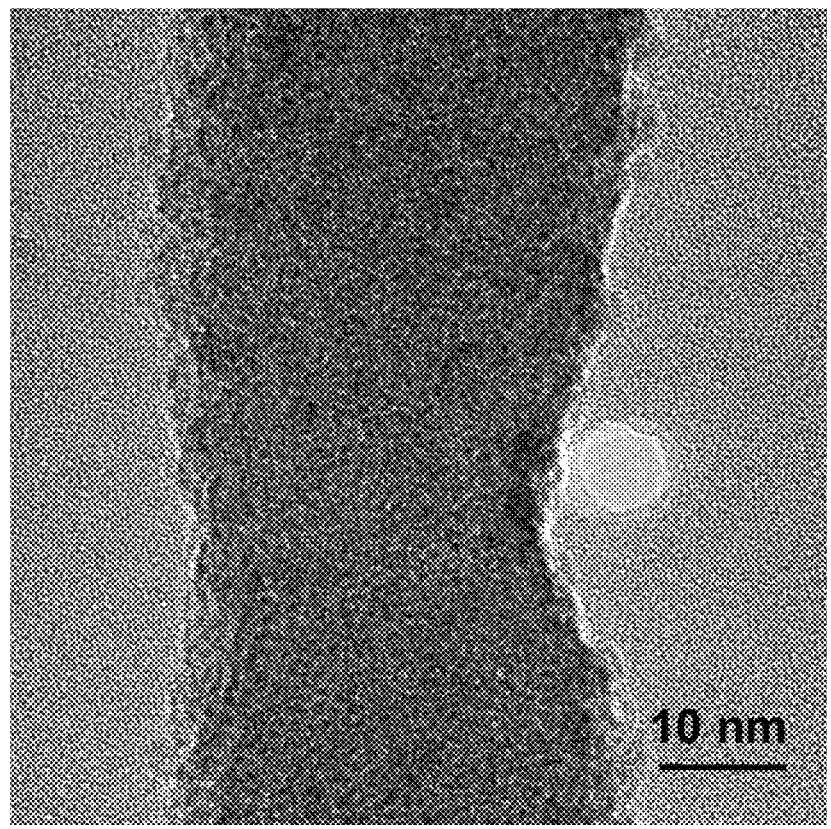

FIG. 18 illustrates a TEM image showing a 40 nm wide graphene nanoribbon sculpted with the electron beam. The nanopore is 7 nm in diameter located 2 nm away from the ribbon. The ribbon is covered by the HSQ resist to allow TEM imaging. Exemplary sculpting and manufacture techniques applicable to graphene are described in U.S. Pat. No. 8,173,335, "Beam Ablation Lithography," issued May 8, 2012, the entirety of which is incorporated herein by reference for all purposes. Graphene nanoribbons below 10 nm wide and down to sub-nm width can be created in this way with single atom precision using high resolution TEM and aberration corrected TEM.

Figure 19:
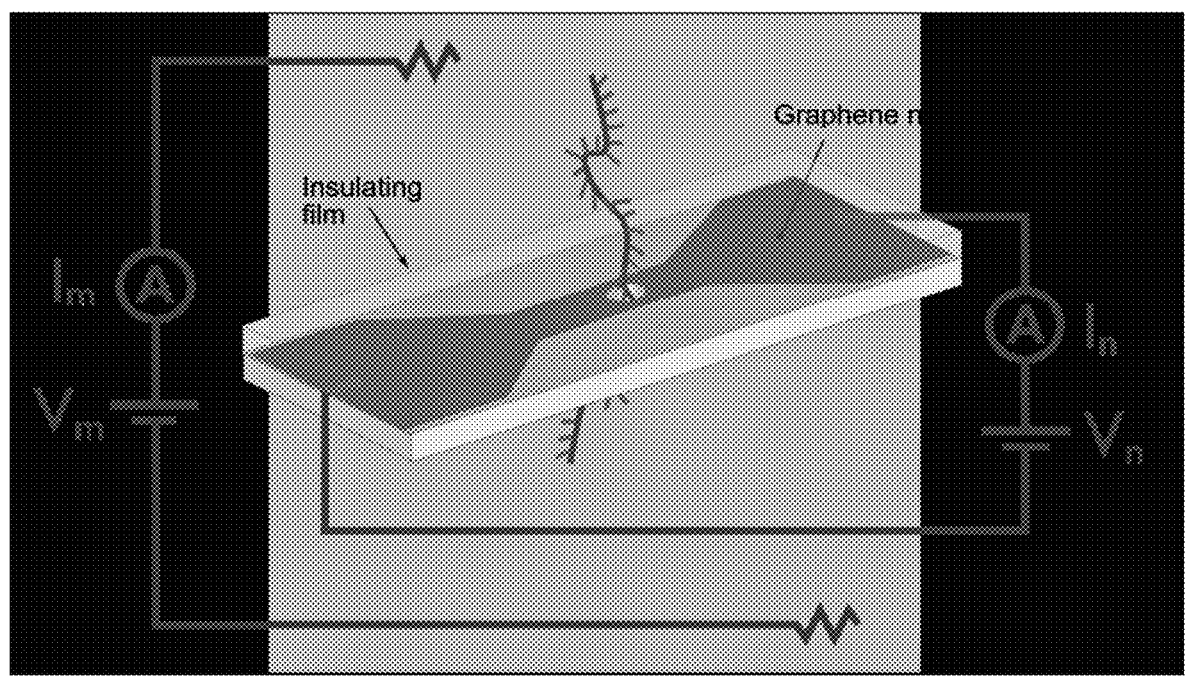
Figure 20:
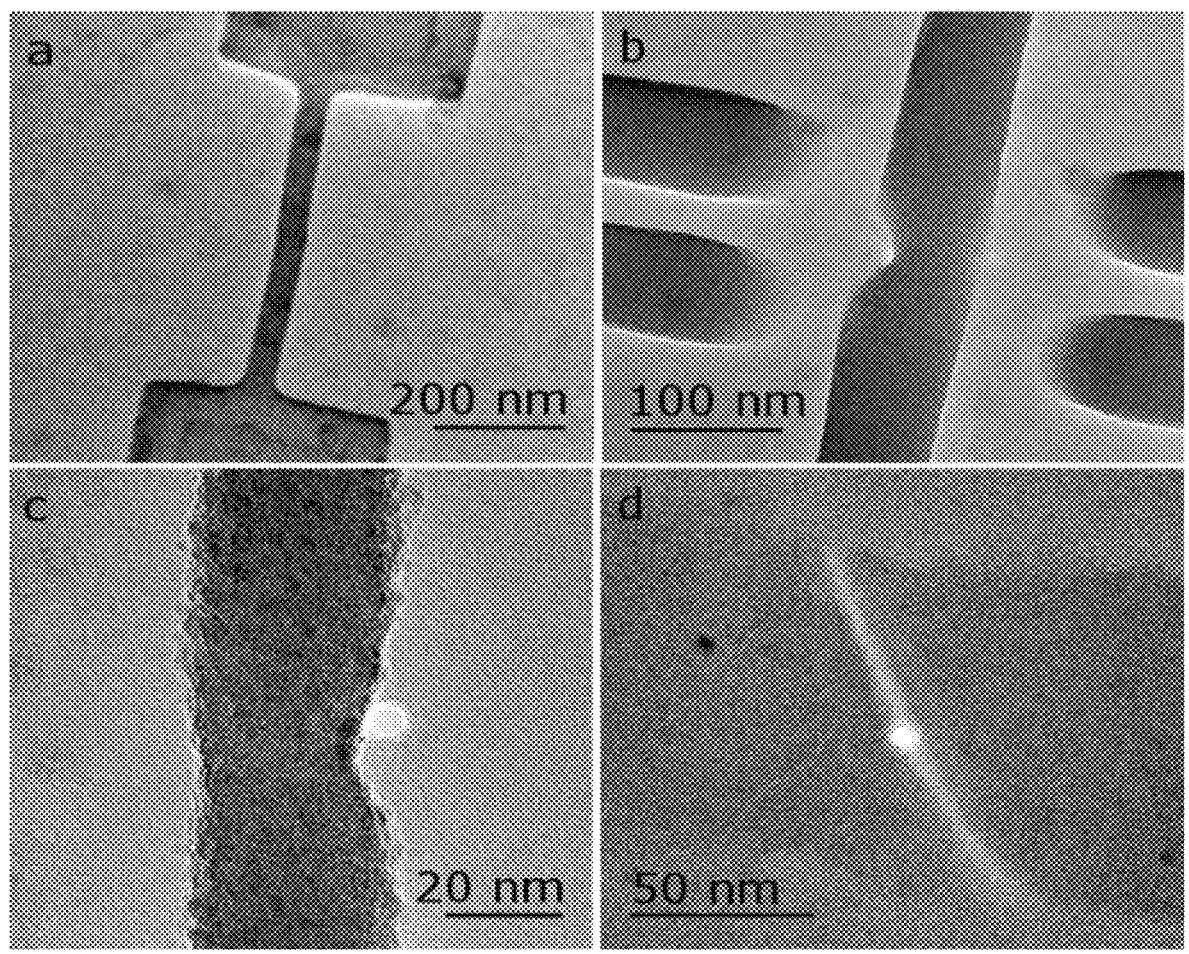
Figure 21:
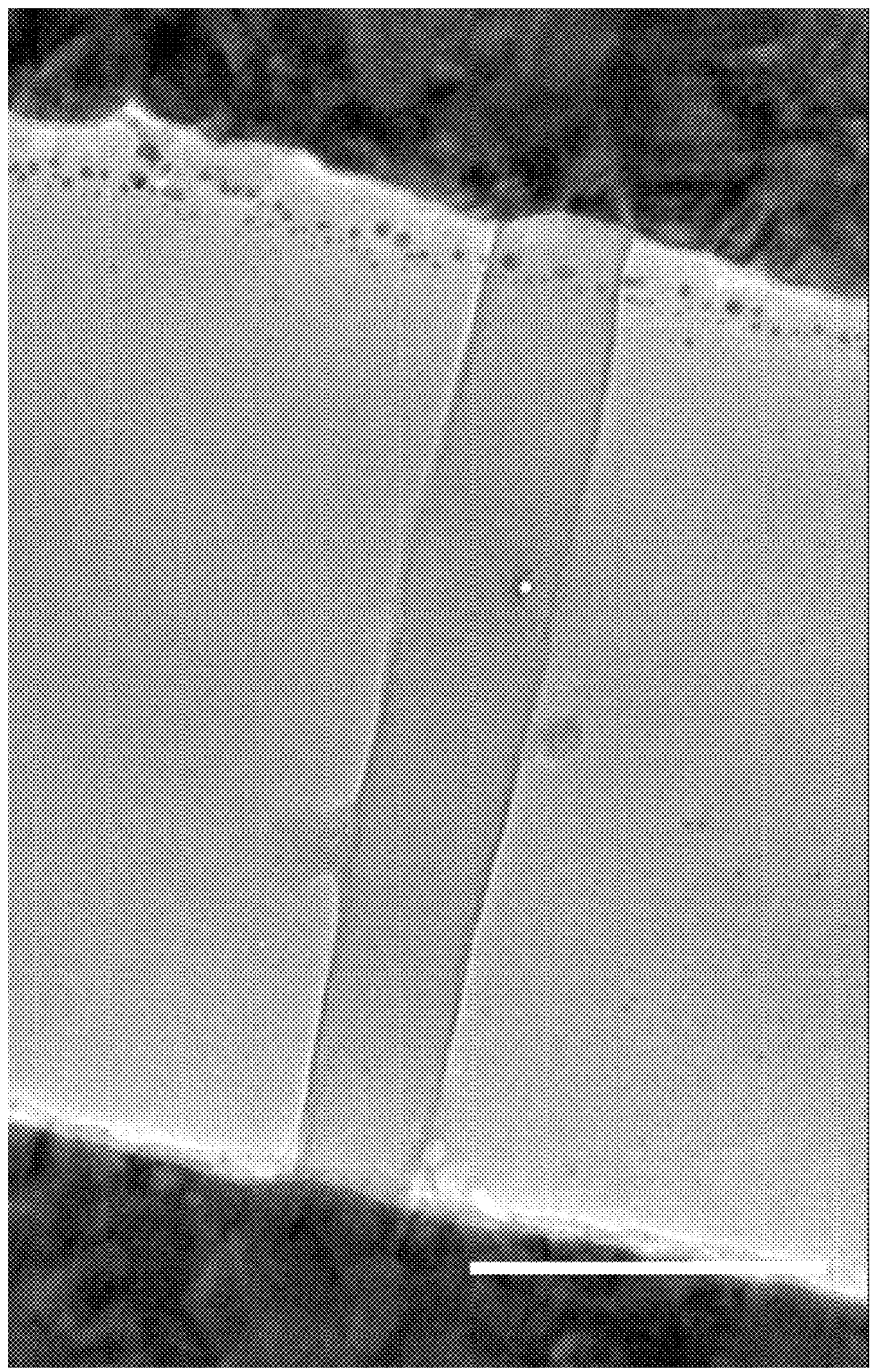
Figure 22:
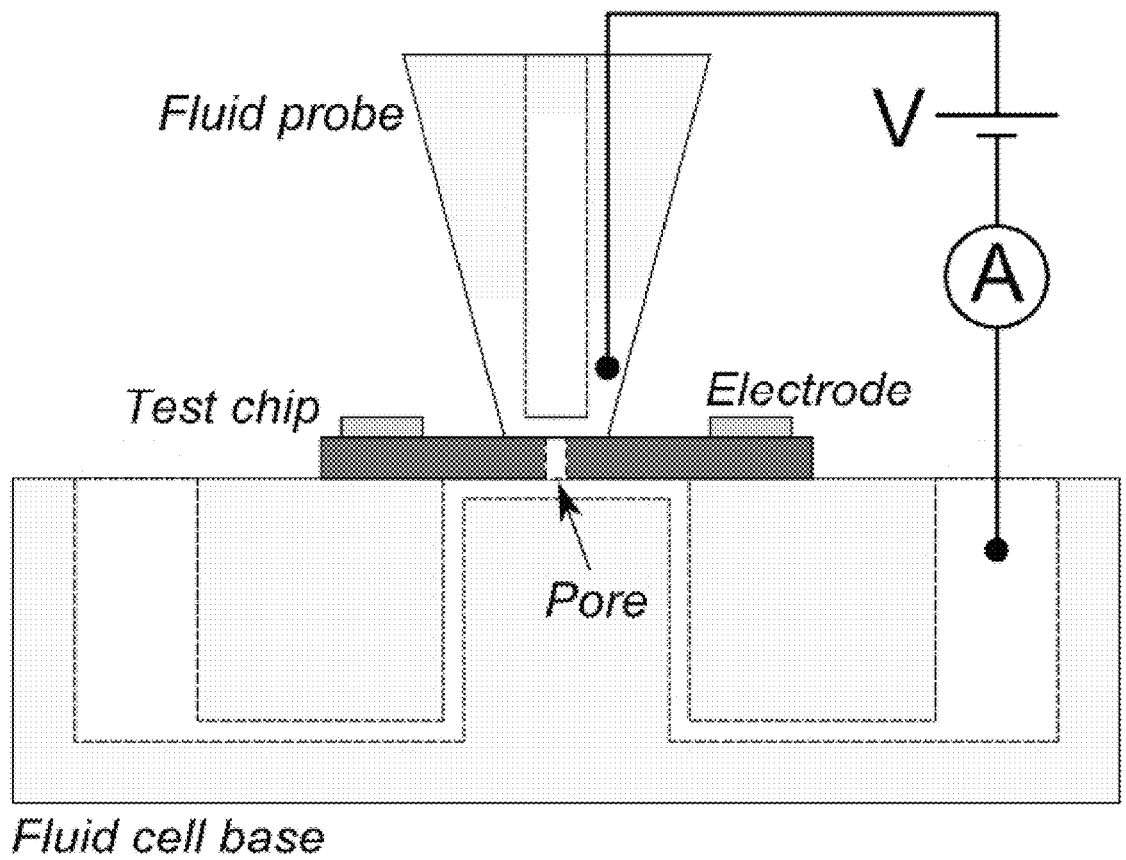
Figure 23:
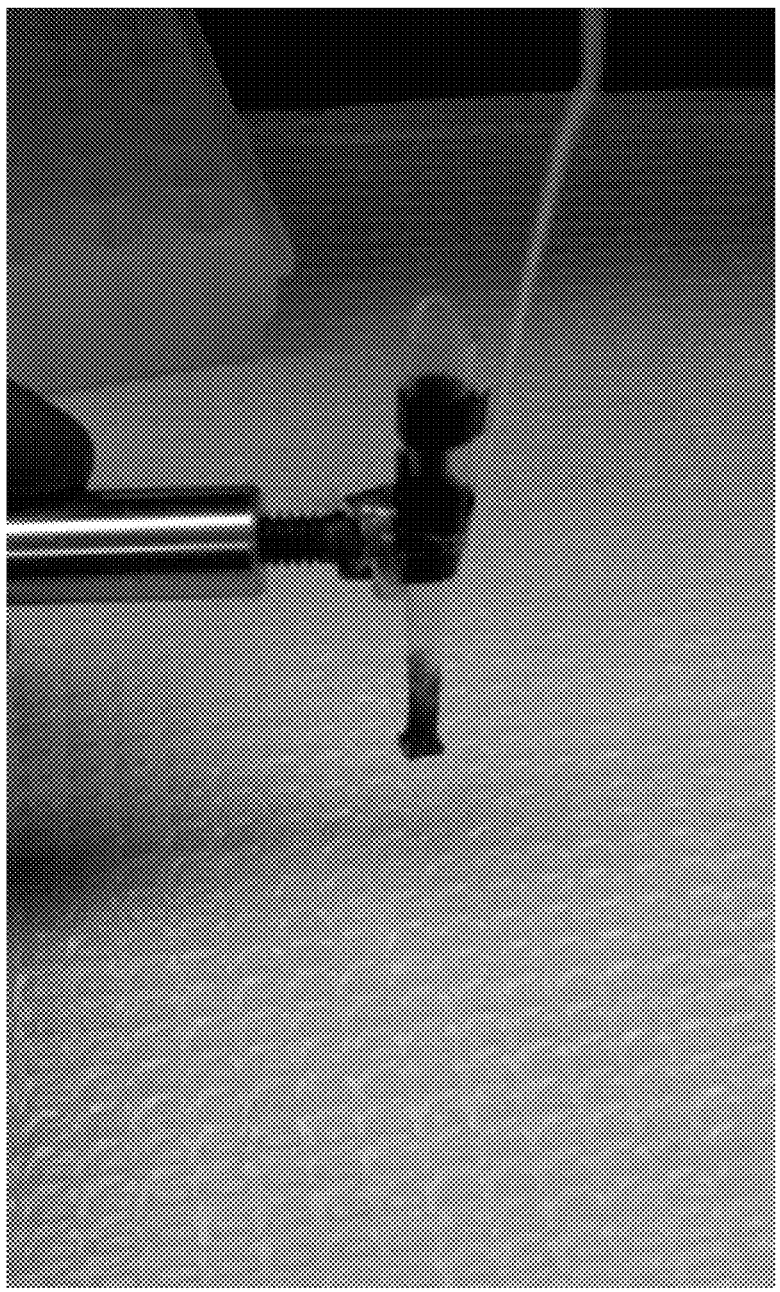
Figure 24:
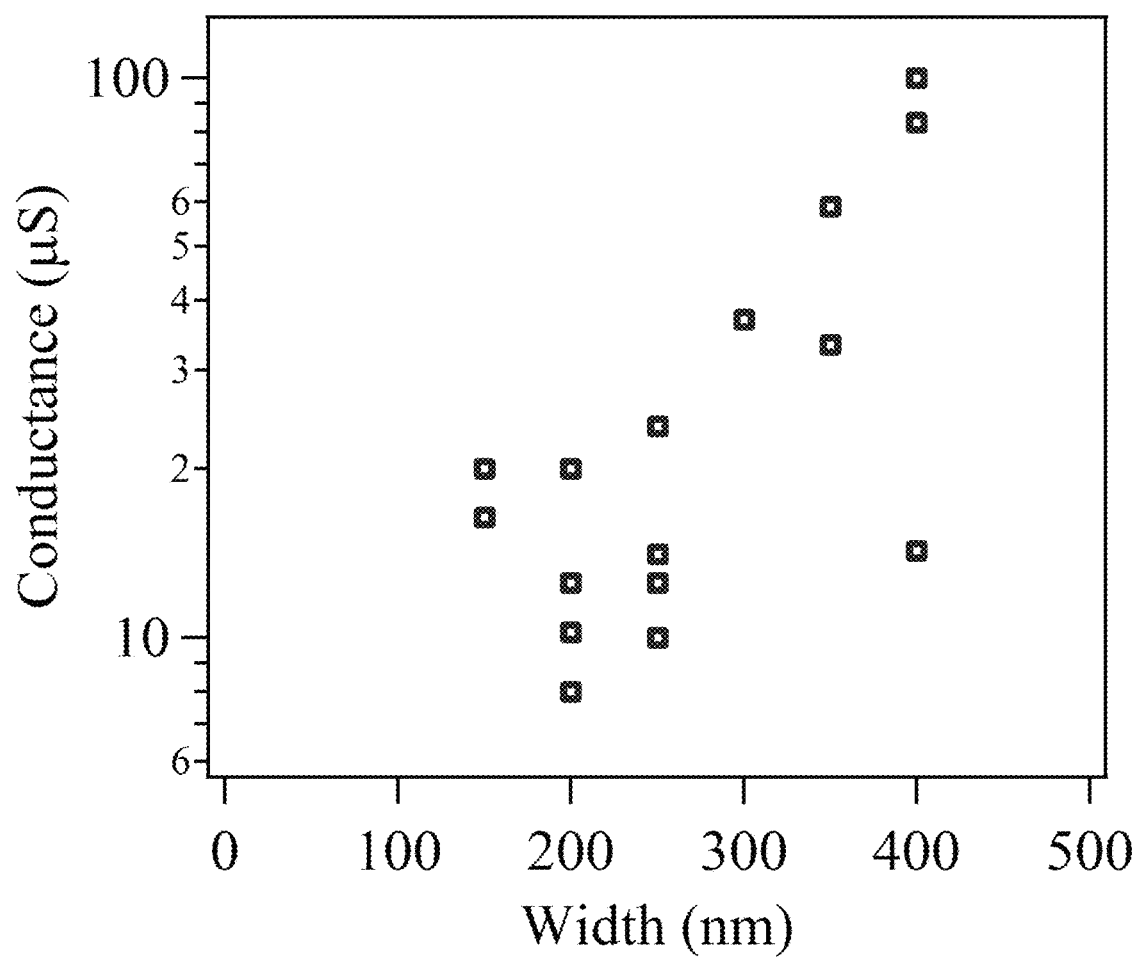
Figure 25:
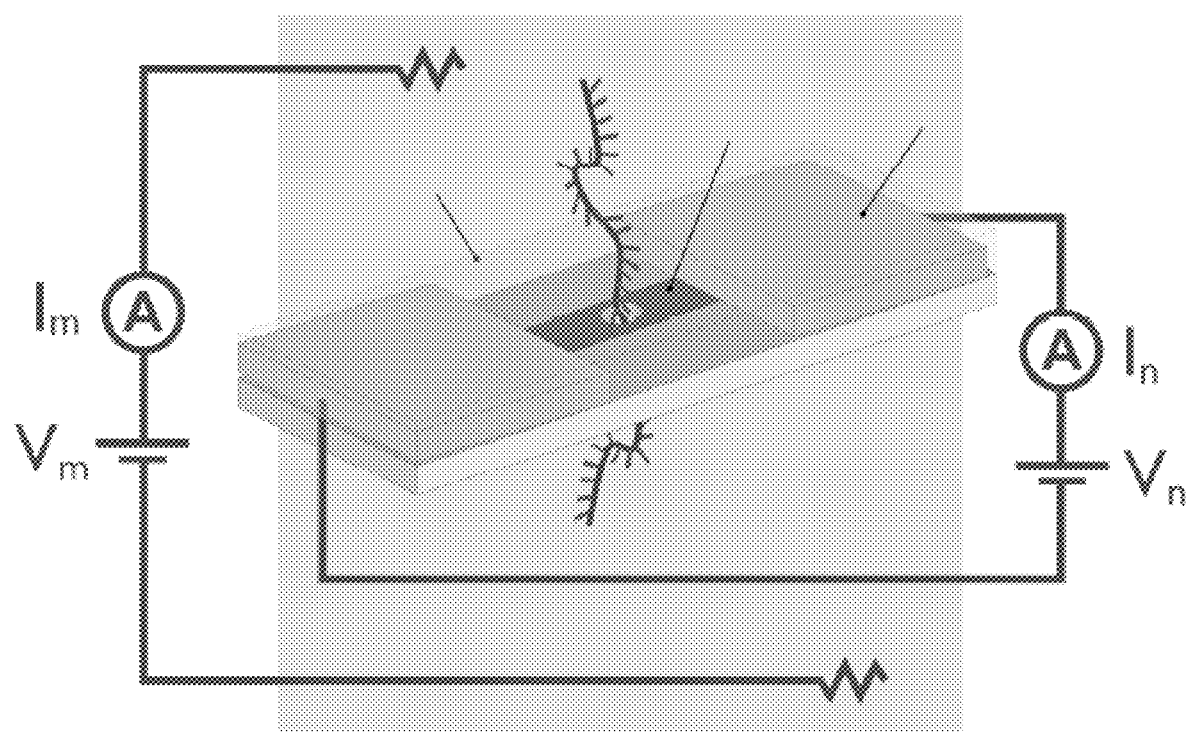
Figure 26:
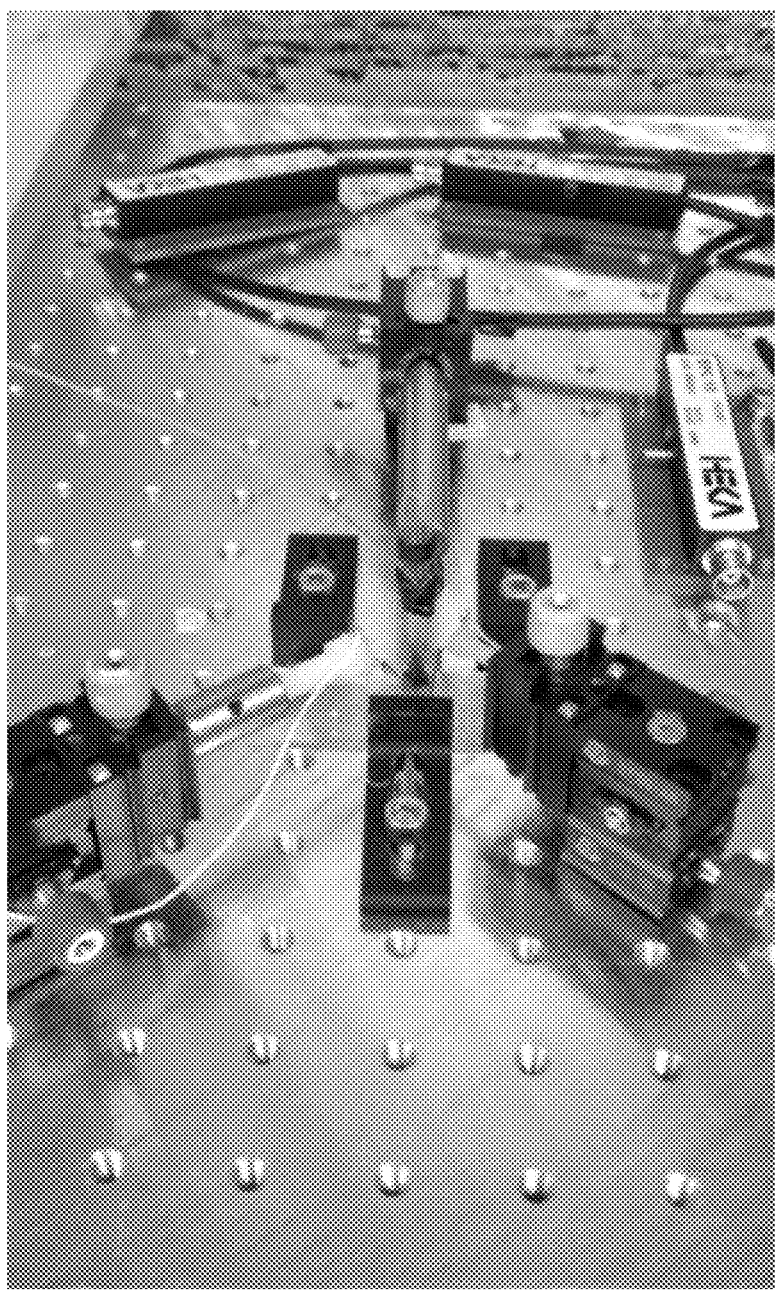
Figure 27:
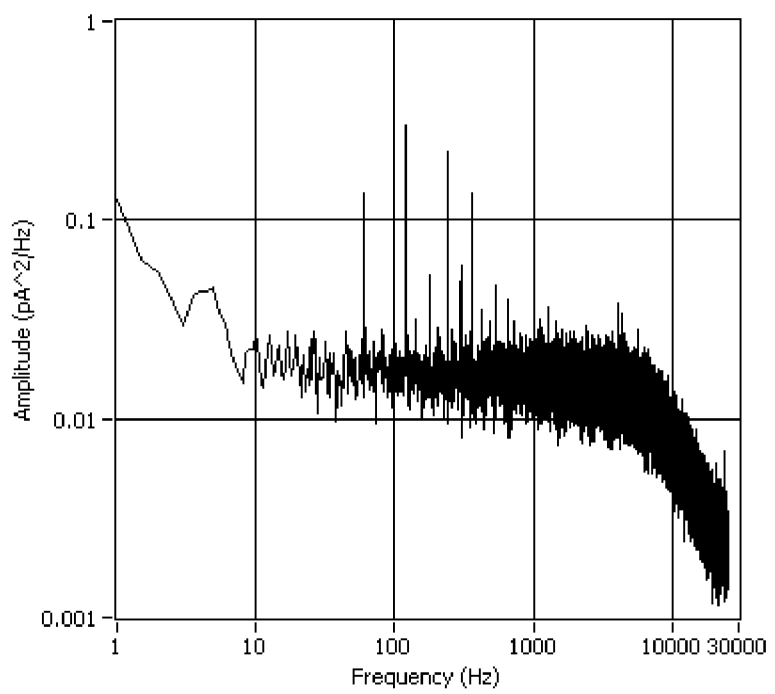
Figure 28:
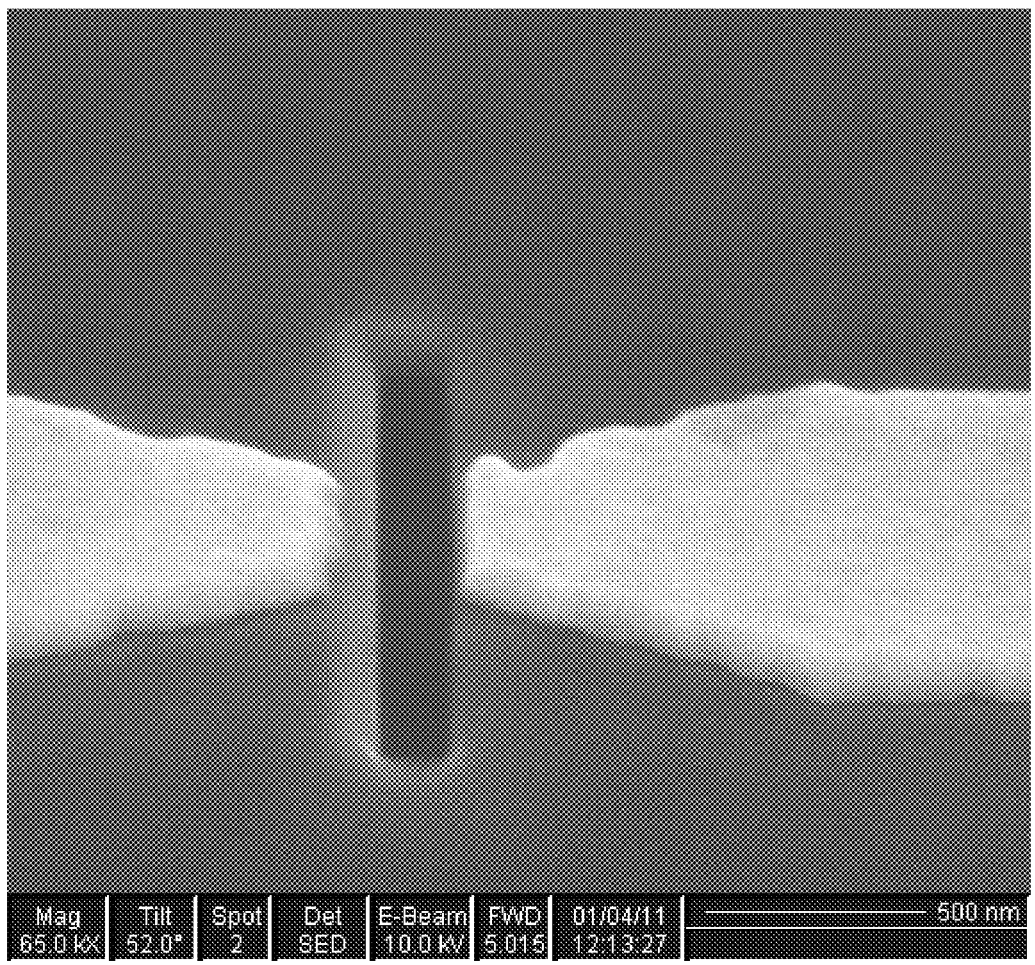
Figure 29:
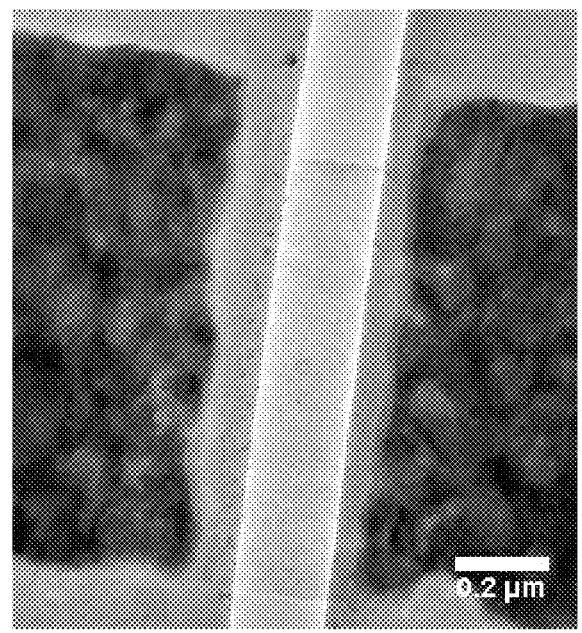
Figure 30:
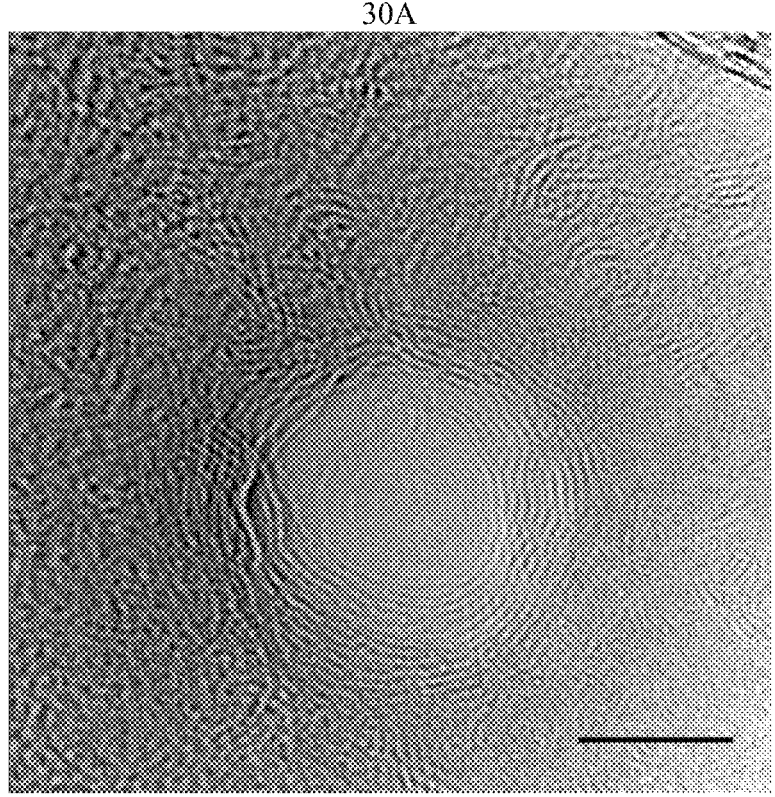
Figure 30:
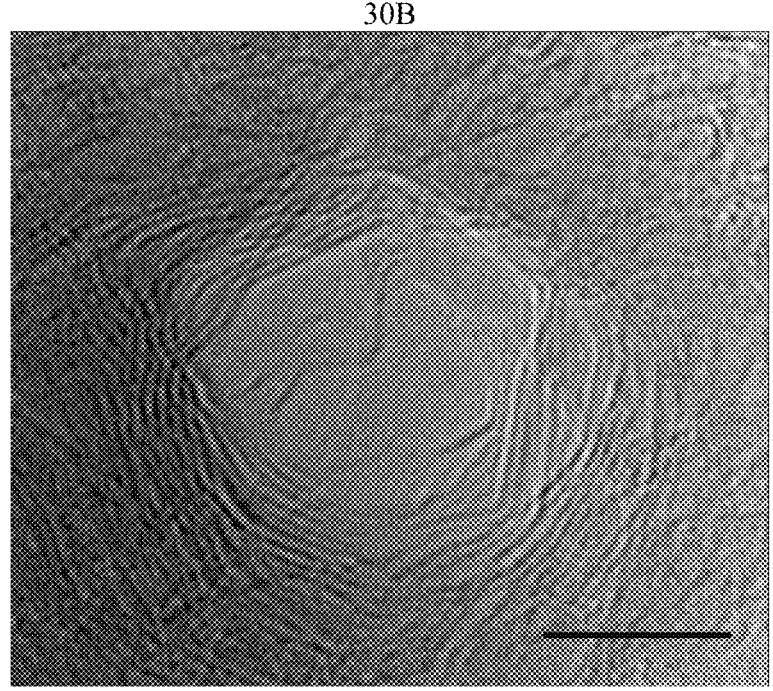
Figure 31:
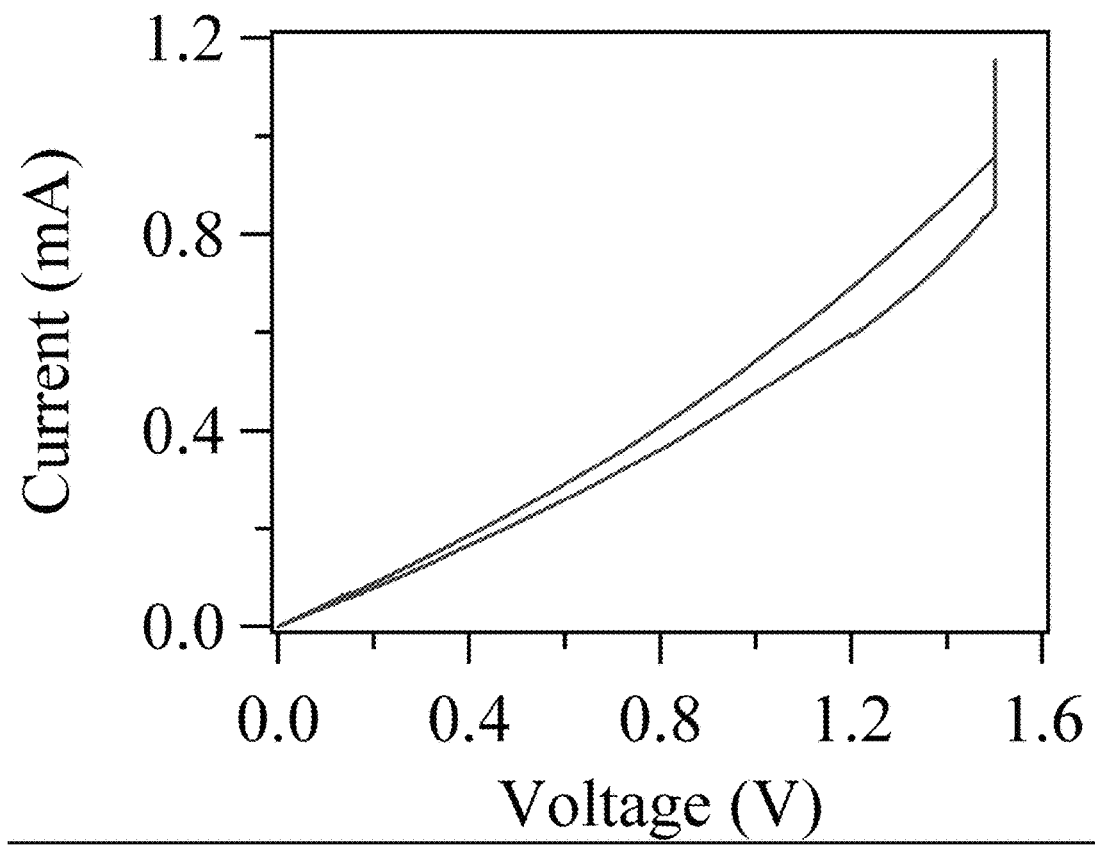
Figure 32:
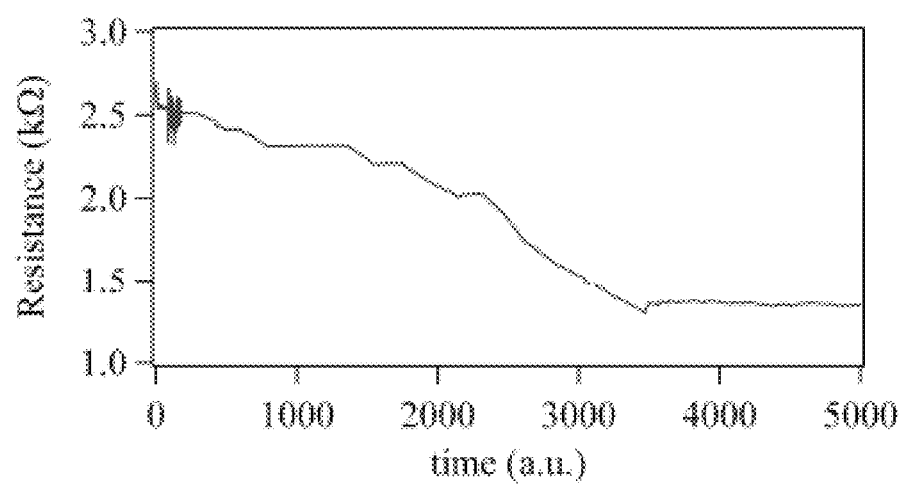
Figure 33:
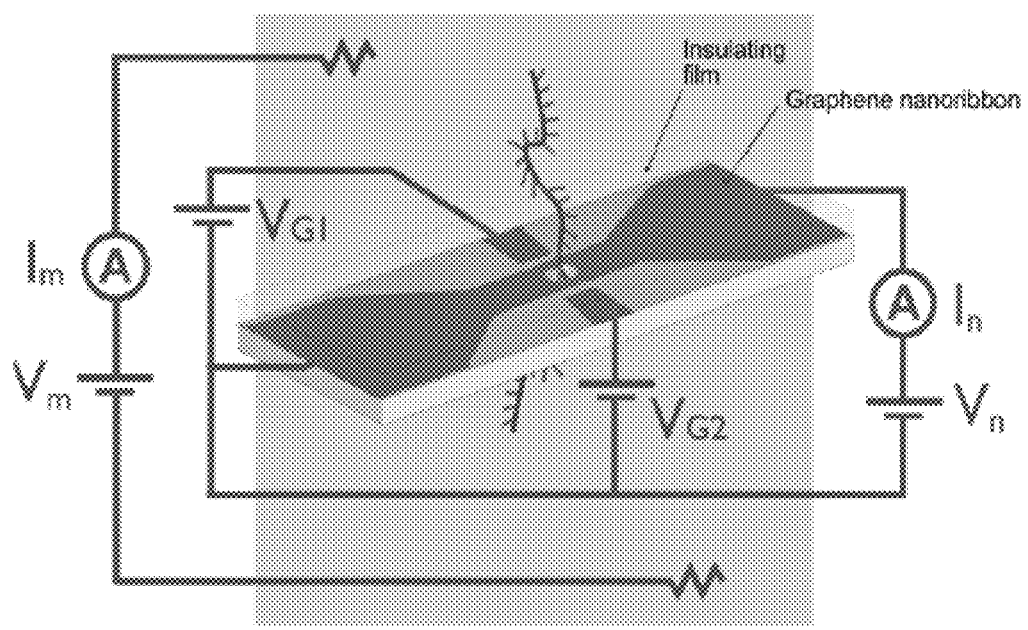
Figure 34:
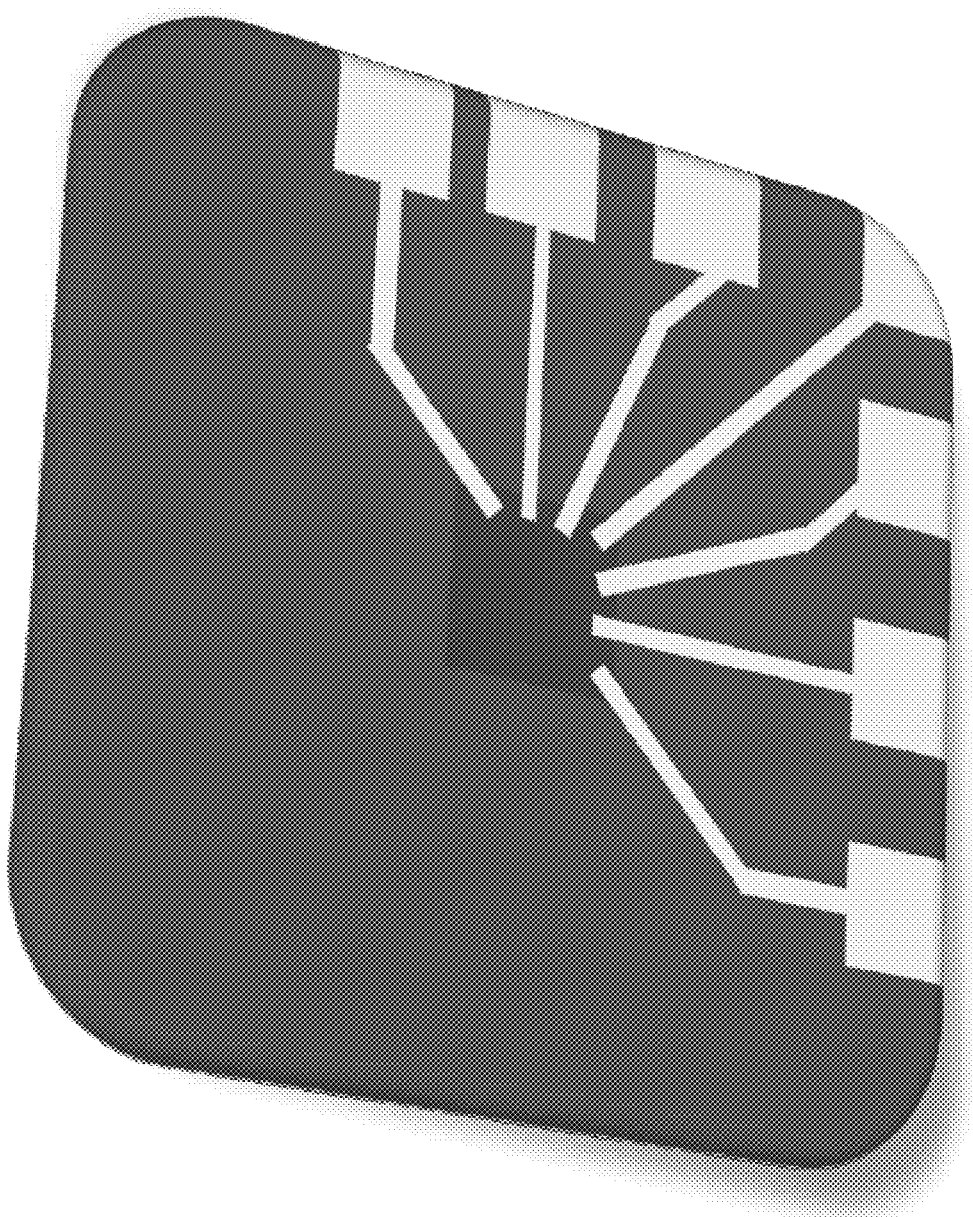

FIG. 19 depicts an example device containing a graphene sheet shaped in form of a nanoribbon with a nanopore drilled in the nanoribbon. Ionic current, $I_m$, is measured with macroelectrodes. The current through the graphene sheet/nanoribbon is $I_n$;

FIG. 20 illustrates examples of fabricated graphene nanoribbons with nanopores in the middle or sides of the nanoribbon. The nanoribbon can be also cut to form graphene nanoelectrodes (as in FIG. 20d). The nanopore pore drilled at the nanoribbon edge, can be surrounded partially by graphene and partially by silicon nitride (as in FIG. 20b). Additional graphene gates near the nanoribbon are also fabricated. These graphene gates are used to modulate the nanoribbon conductance by applying a gate voltage to the gates and therefore, control the nanoribbon conductance;

FIG. 21 illustrates a TEM image of the graphene nanoribbon with a nanopore drilled in it fabricated between two gold electrodes (black regions in the image), on top of a silicon nitride substrate;

FIG. 22 illustrates an example of a fluidic cell made to accommodate the graphene nanopore/nanoribbon/nanosheet device between metal electrodes;

FIG. 23 illustrates an exemplary optical image of an exemplary system;

FIG. 24 depicts exemplary measured graphene nanoribbon conductance as a function of nanoribbon width;

FIG. 25 depicts a cartoon view of a graphene nanoribbon device with a nanopore, through which a single stranded DNA molecule is translocated. The amp-meters shown measure two current signals: one is the ionic current passing through the pore ($I_m$ in the image) and measured using macroelectrodes, and two is the current passing through the graphene ribbon ($I_n$ the image) and measured with nanoelectrodes;

FIG. 26 illustrates a photograph of the micromanipulator setup to electrically contact the graphene nanopore sheet and measure the ionic current and the current through the graphene is included;

FIG. 27 illustrates a measurement of the electrical noise (power spectral density vs. frequency) of the ionic current through the graphene nanopore measured in the above setup;

FIG. 28 depicts a scanning electron microscope (SEM) image of a hole in the silicon nitride membrane between metal electrodes;

FIG. 29 illustrates a graphene sheet suspended on top of this hole and shaped in form of a ribbon (see TEM image below; black is the metal, darker grey is silicon nitride, light grey is graphene);

FIGS. 30A and 30B illustrate a nanopore in graphene before (A) and after (B) annealing;

FIG. 31 shows current v. voltage for an exemplary graphene nanopore device. This current is measured through the graphene sheet;

FIG. 32 illustrates the reduction in resistance of the graphene vs. time during an exemplary annealing process;

FIG. 33 illustrates a possible graphene nanopore device geometry involves adding additional side gates near the current-annealed nanopore and nanoribbon. VG1 and VG2 are gate voltages applied to the gates to control the graphene ribbon conductance;

FIG. 34 illustrates an image of a silicon nitride chip used with fabricated metal electrodes. The graphene sheet is deposited on top of, or below of the metal pattern. The window in the middle has a hole on top of which graphene is suspended and nanopores are drilled into the graphene sheet with a TEM beam.

Figure 35:
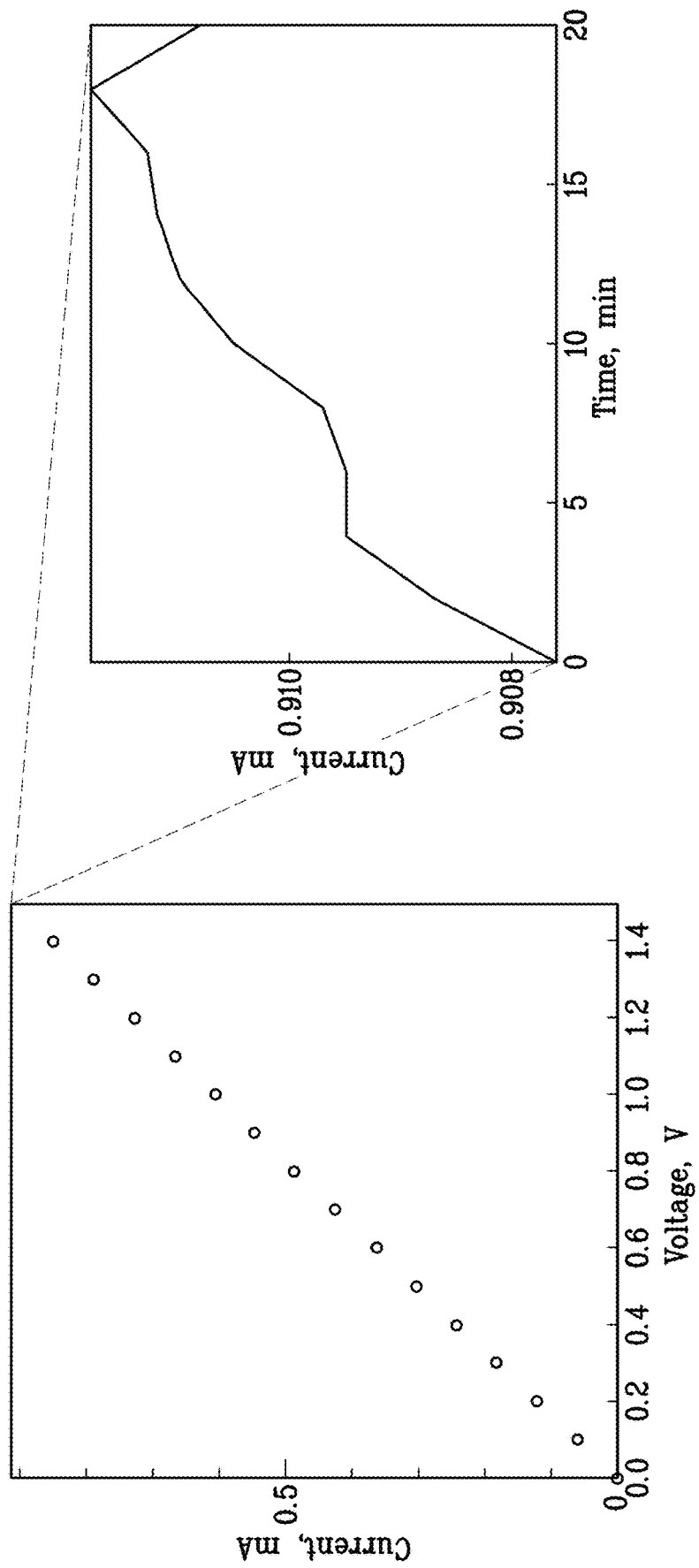
Figure 36A:
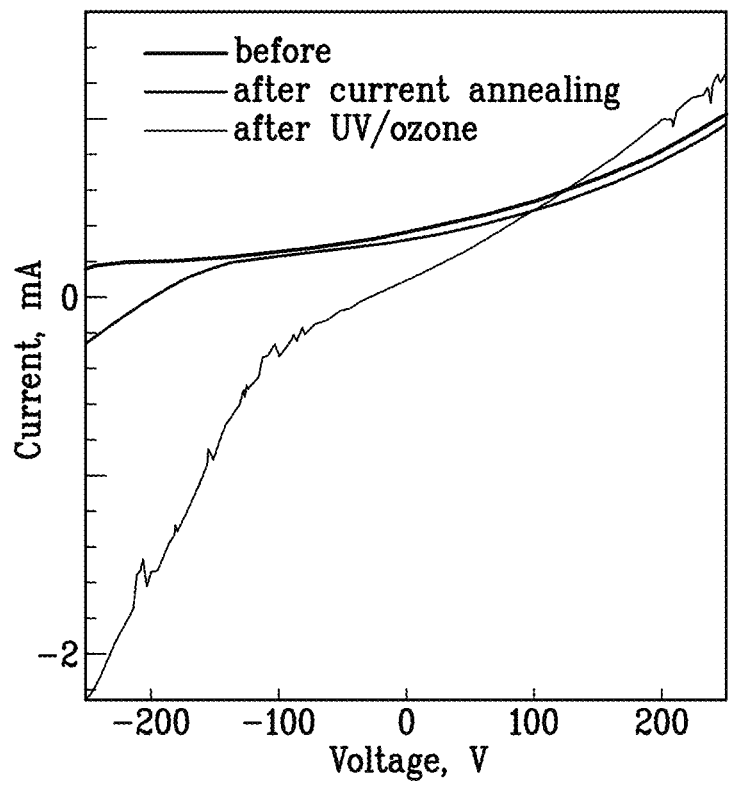
Figure 36B:
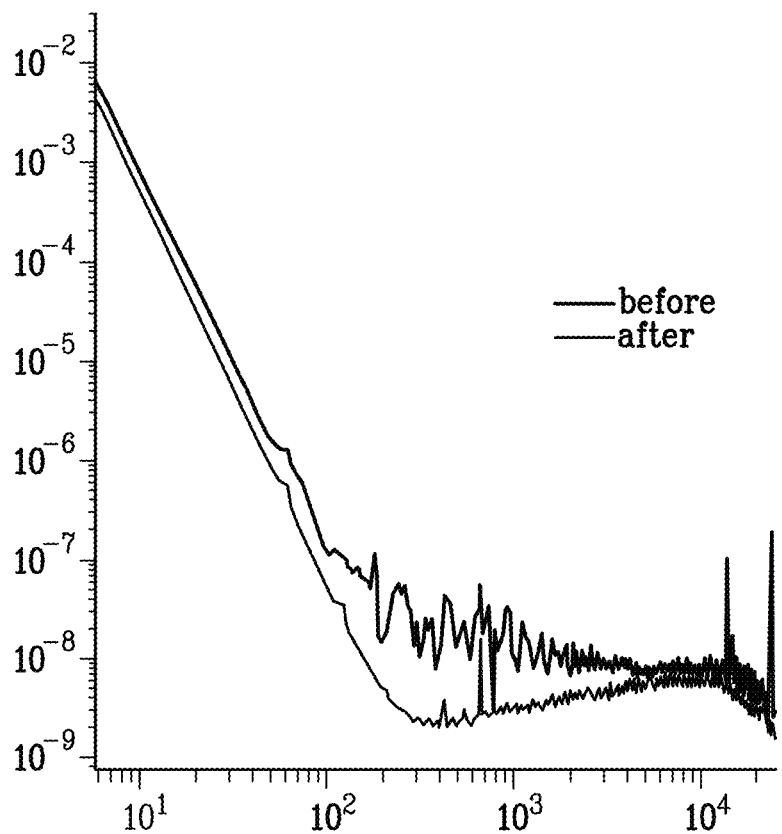

FIG. 35 illustrates current vs. voltage through the suspended graphene nanopore sheet. When the voltage is held constant for some time (for example at 1.6 V), the current through the graphene nanopore sheet further increases in time (meaning that the resistance decreases, as a consequence of current-annealing). This process leads to the cleaning and improvement of the graphene nanopore surface; and FIGS. 36A and 36B illustrate ionic current vs. voltage (36A) when the device is assembled into the fluid cell and one is measuring the ionic current passing through the pore. The ionic current noise (36B) (lower curve) after current-annealing is lower than before current-annealing (upper curve on the right). This means that current-annealed nanopores, i.e. nanopores that were exposed to elevated temperatures, are less electrically noisy and more sensitive for the detection and analysis/sequencing of biomolecules. This is particularly useful for their use in DNA sequencing applications. In addition, the current through graphene nanoribbons that are current annealed is less noisy and current-annealed graphene nanoribbons are more sensitive for the detection and analysis/sequencing of biomolecules.

Figure 37:
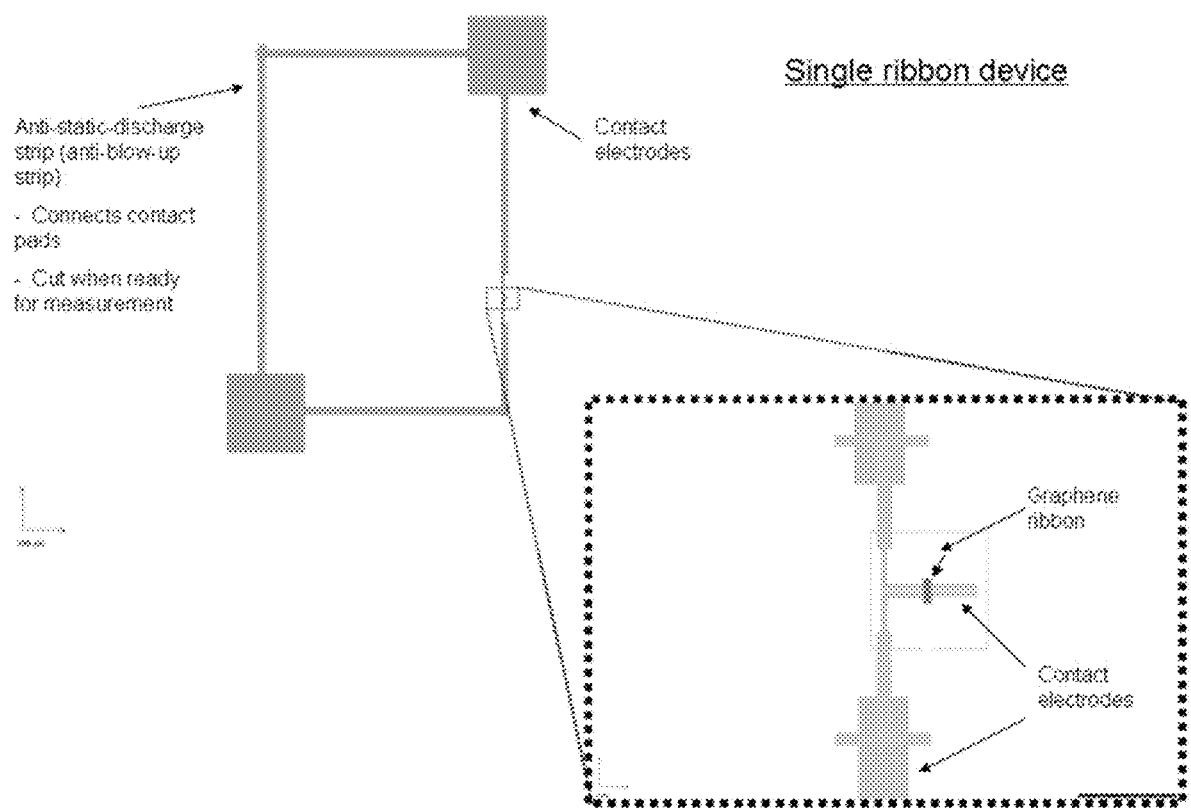
Figure 38:
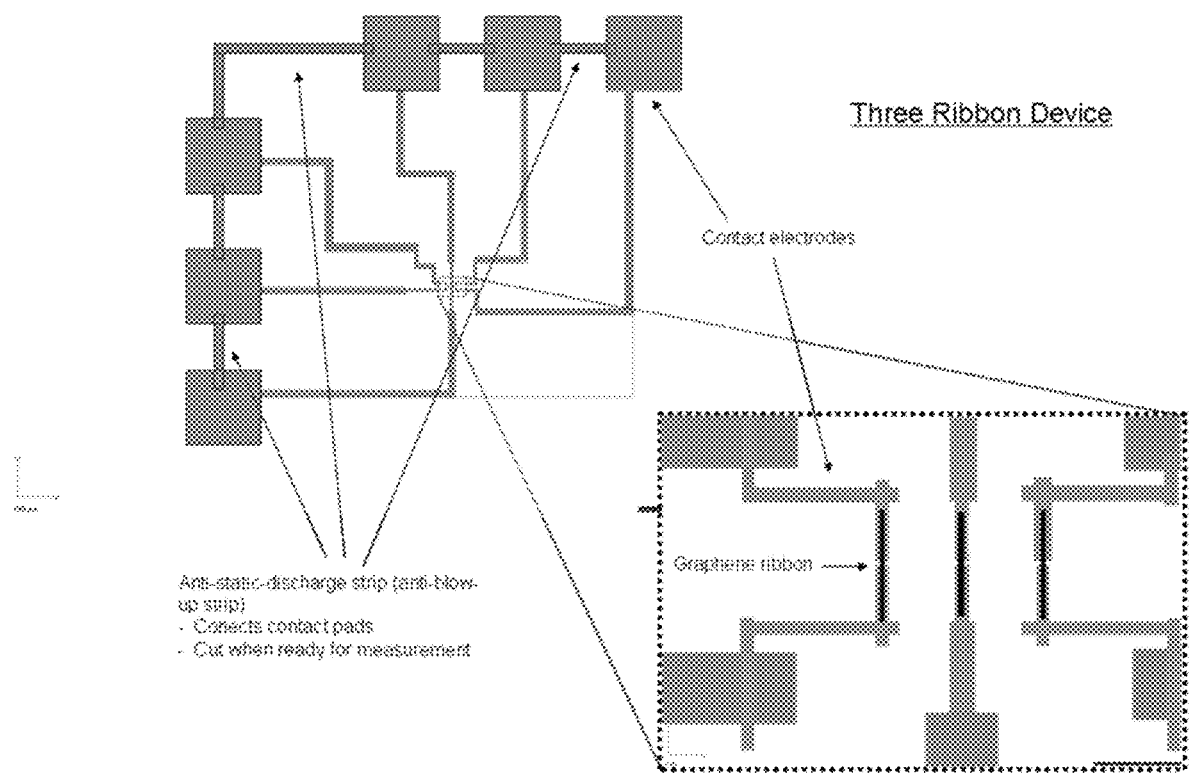
Figure 39:
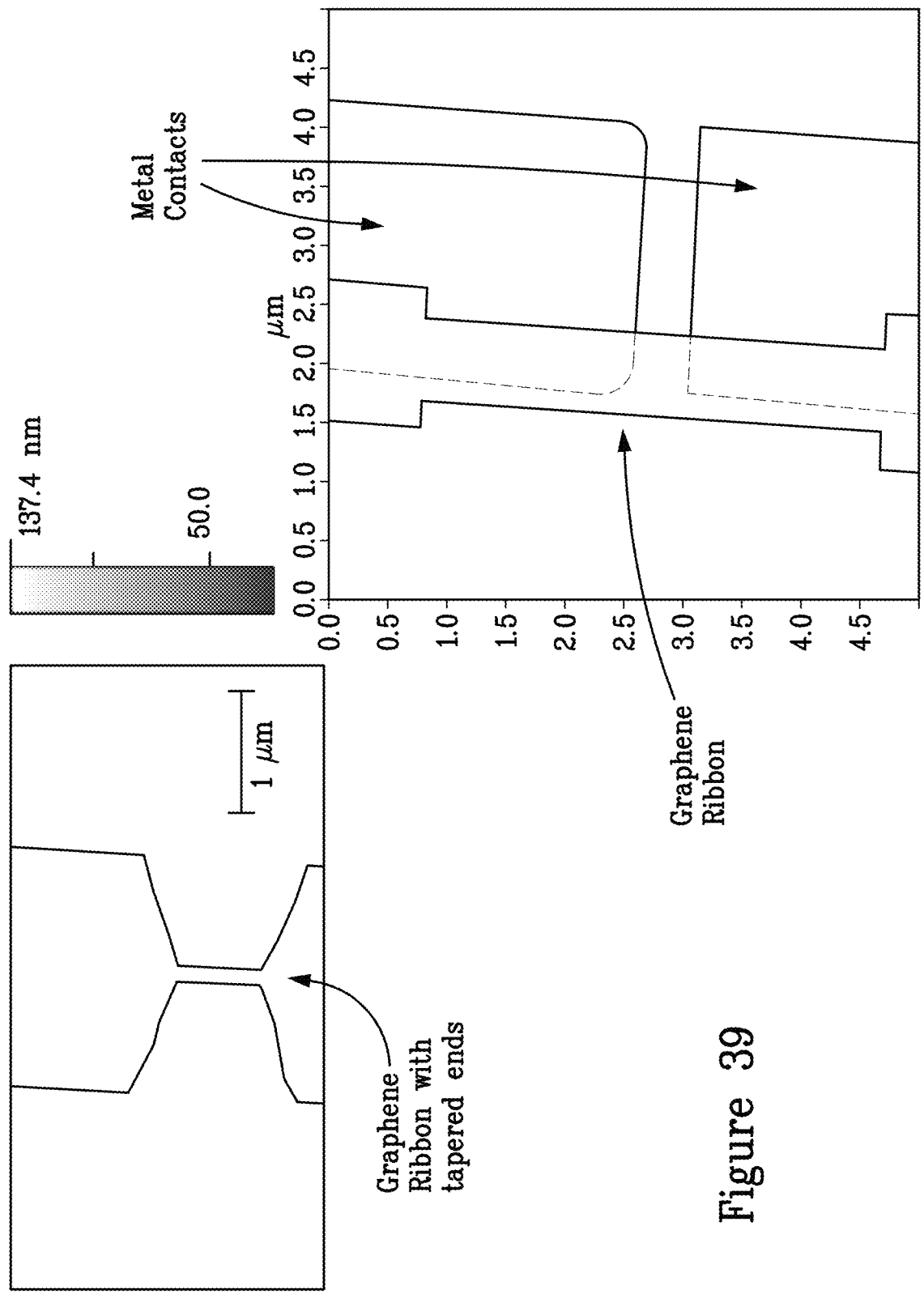
Figure 40:
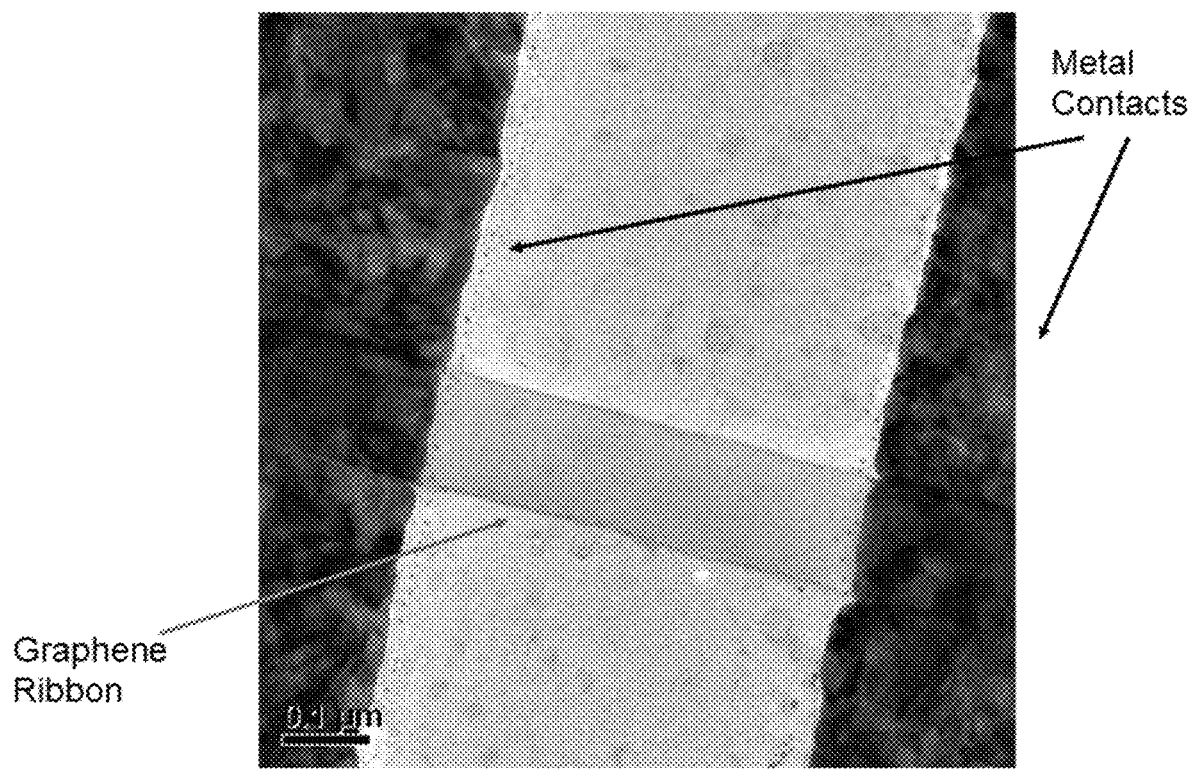
Figure 41:
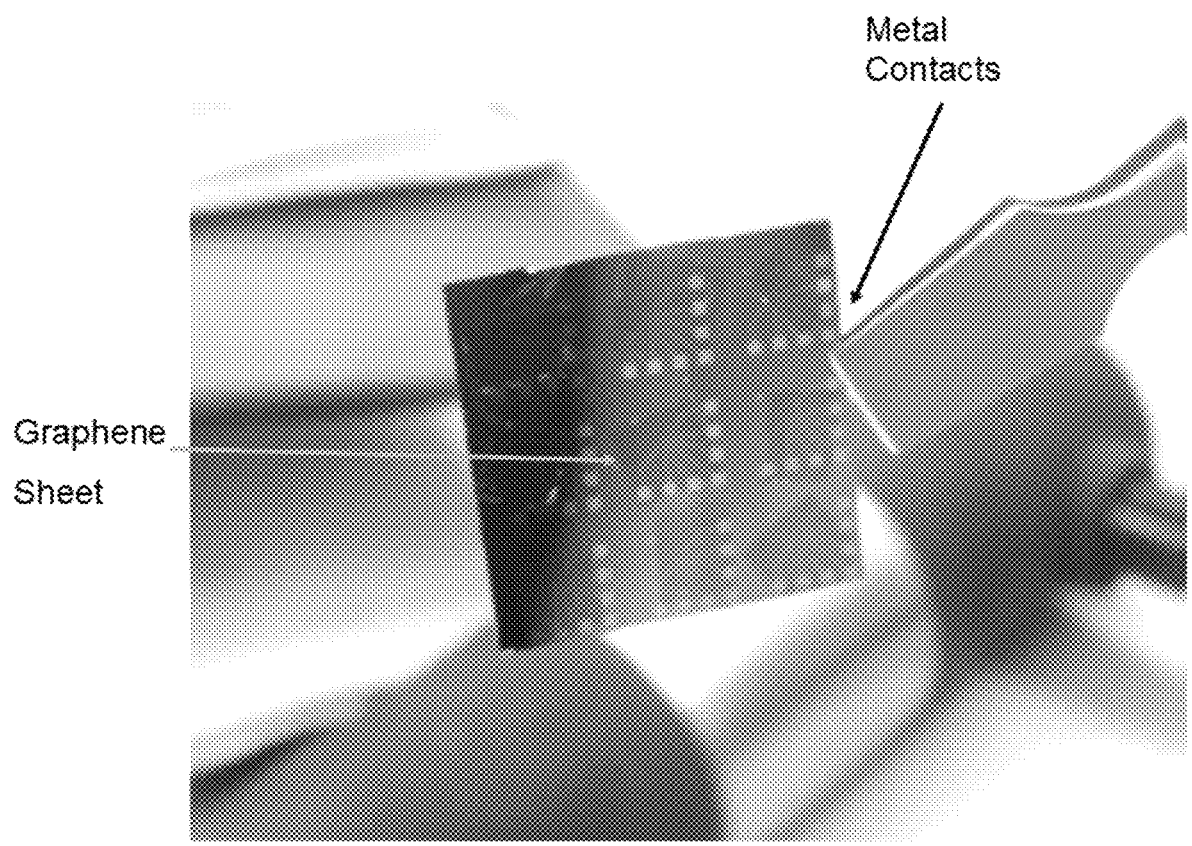
Figure 42:
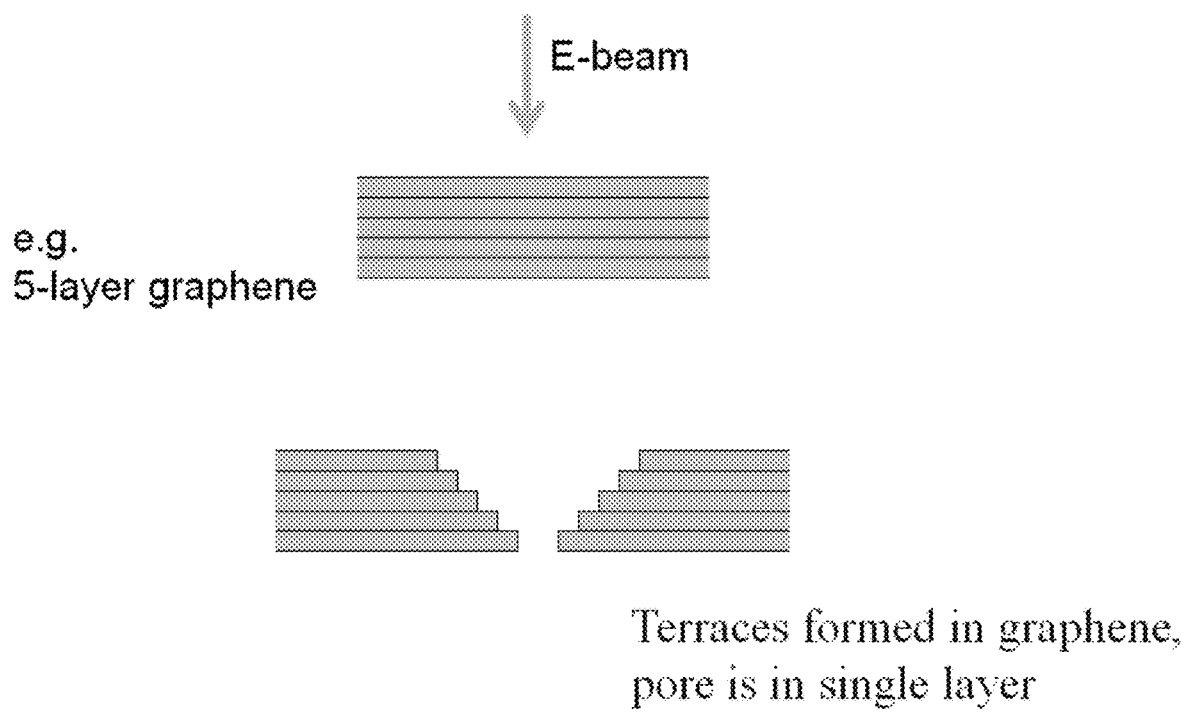
Figure 43:
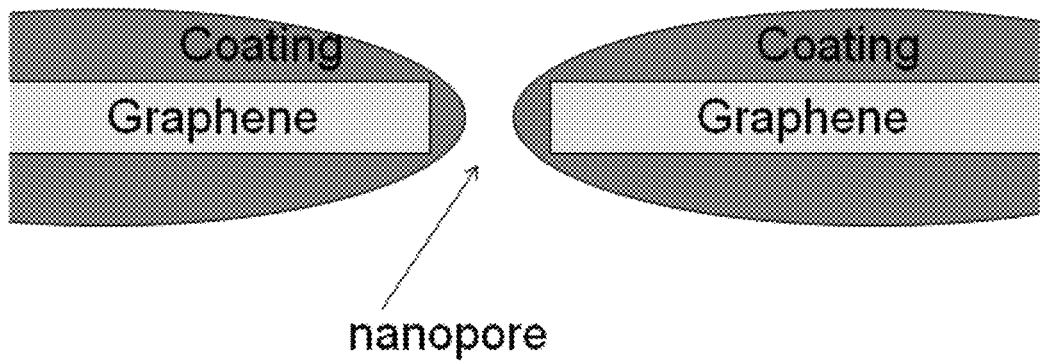
Figure 44:
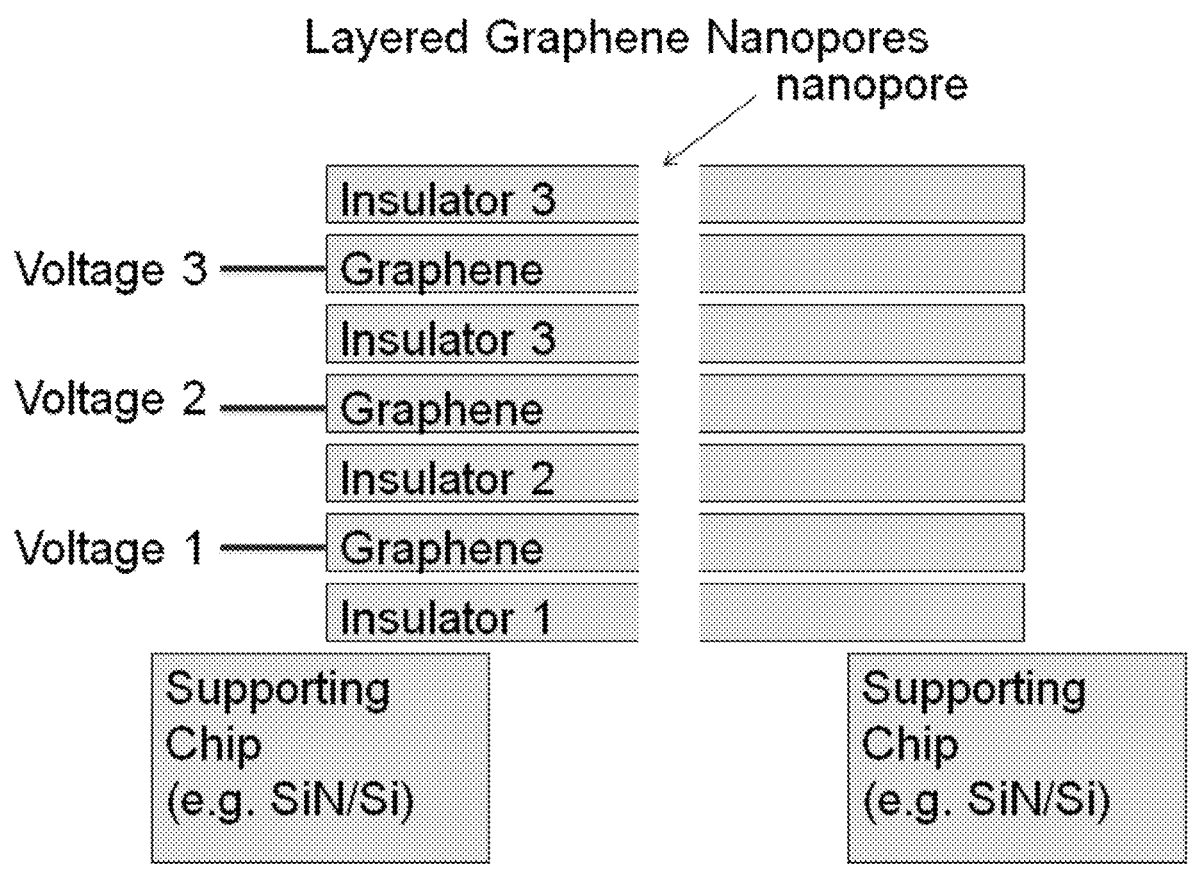
Figure 45:
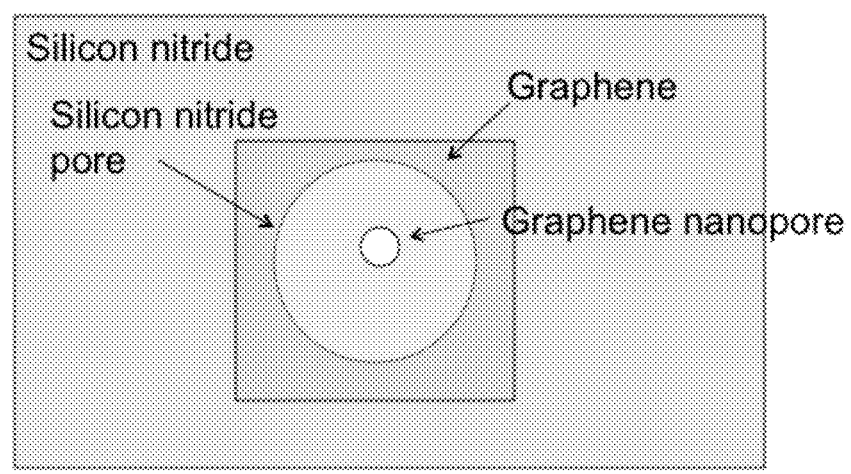
Figure 46:
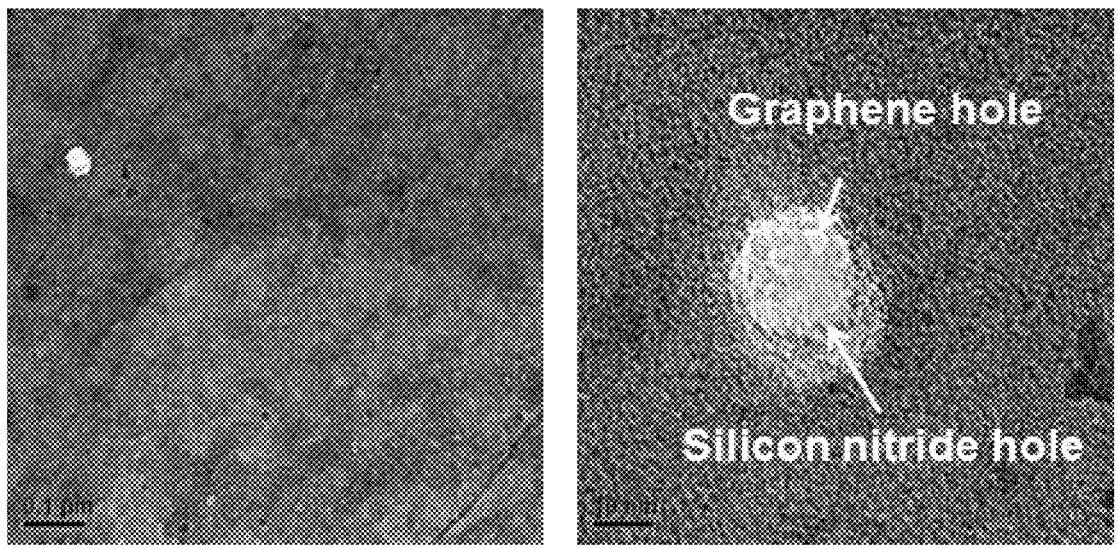
Figure 47:
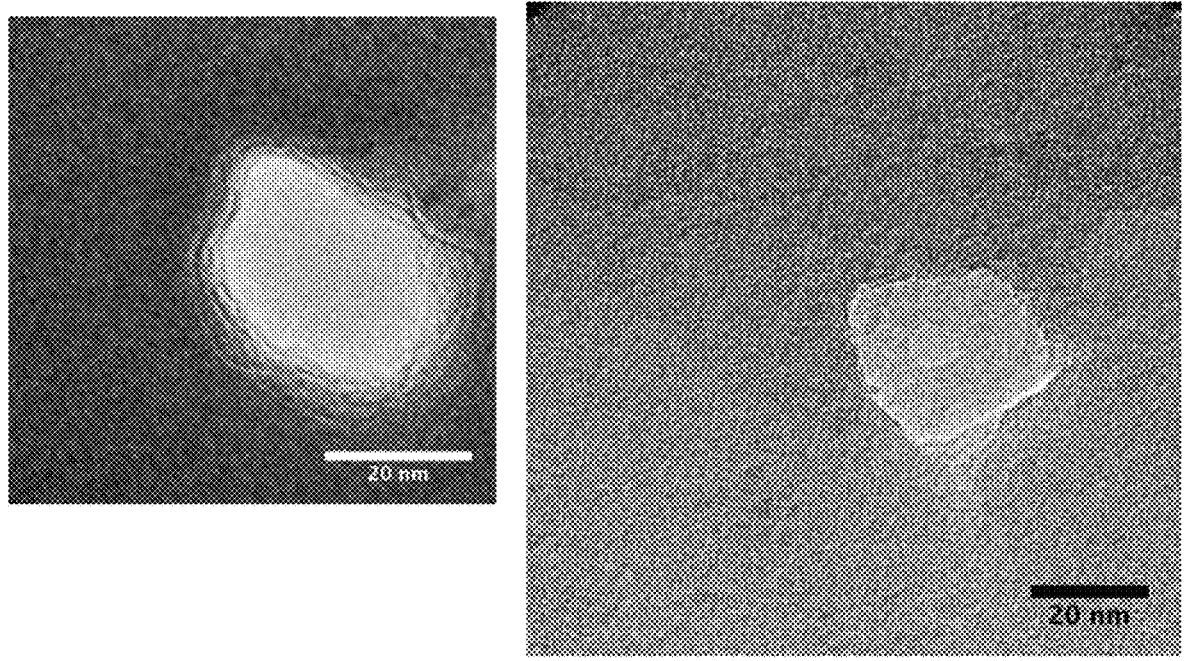
Figure 48:
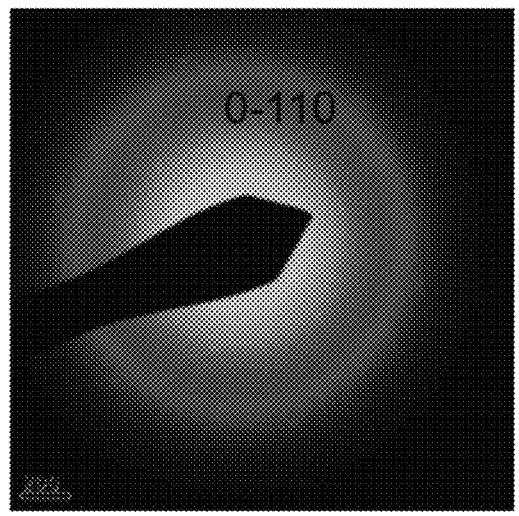
Figure 49:
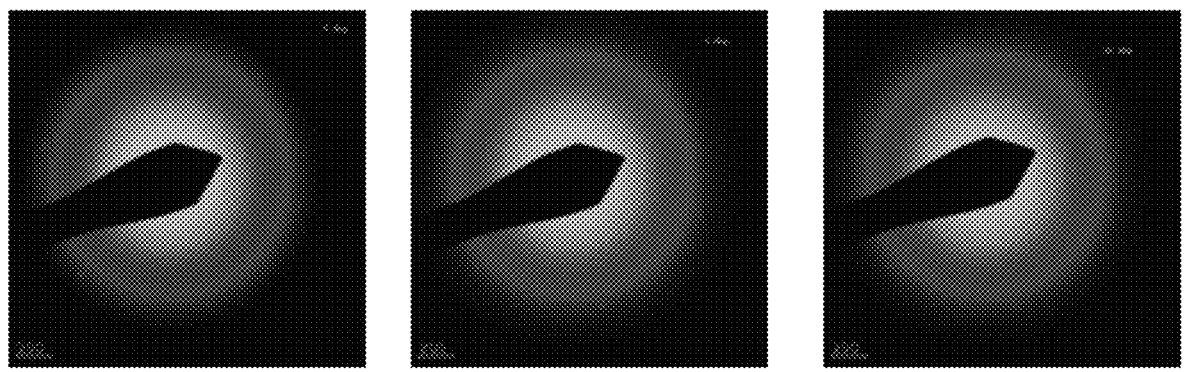
Figure 50:
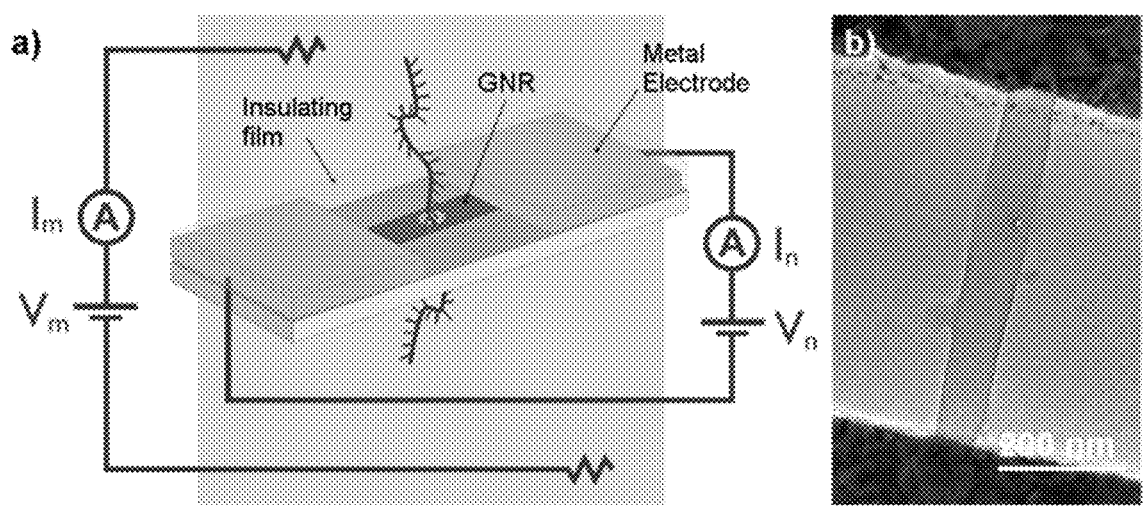
Figure 51:
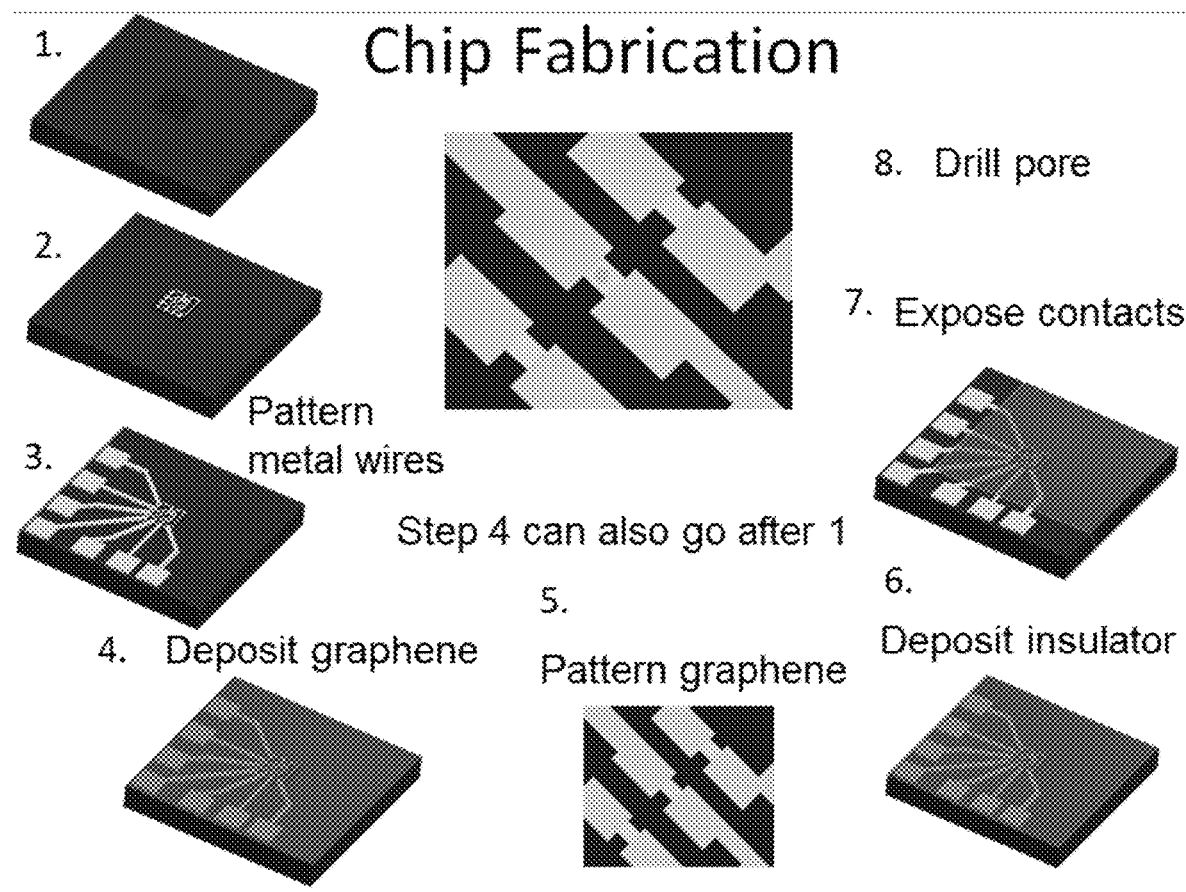
Figure 52:
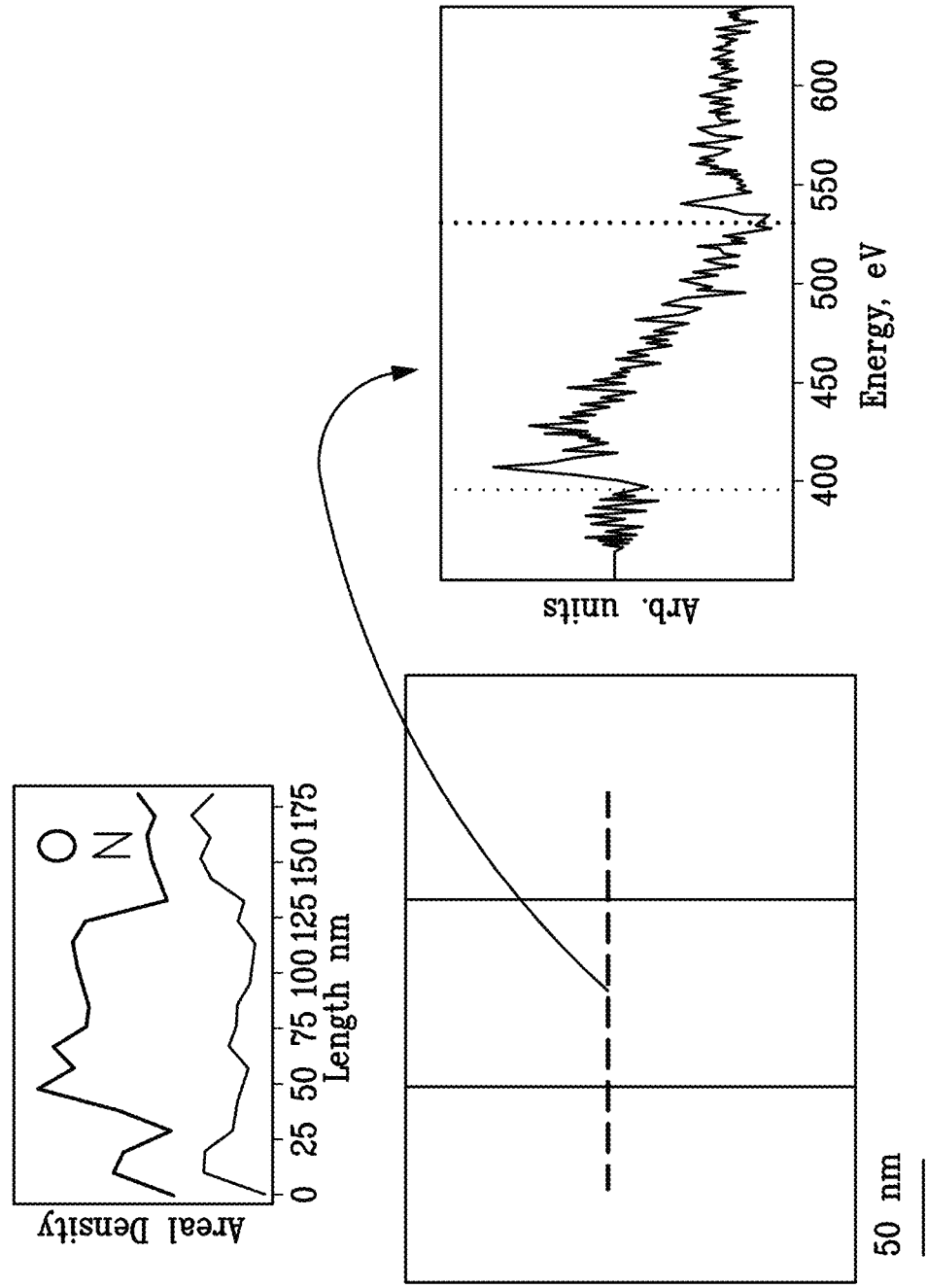
Figure 53:
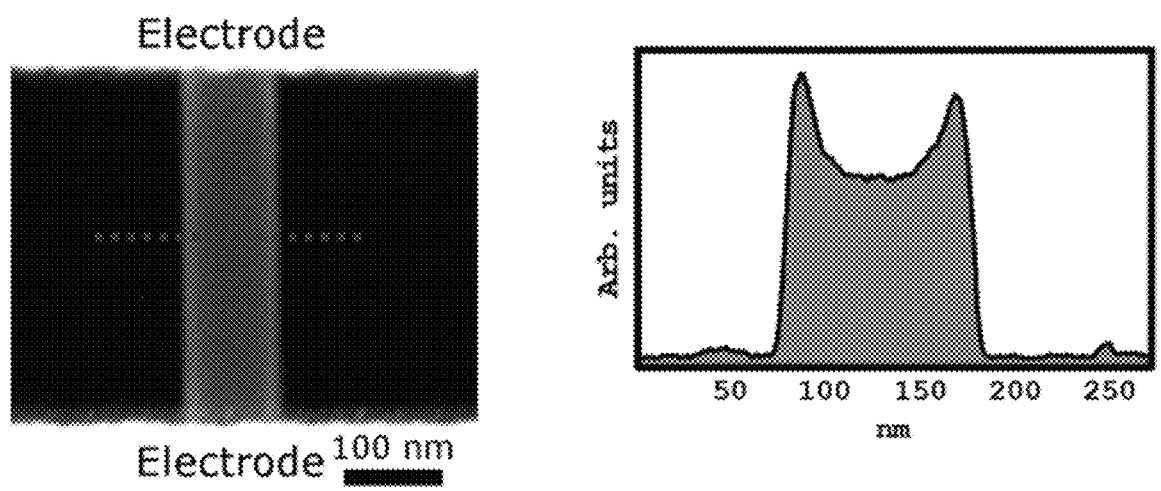
Figure 54:
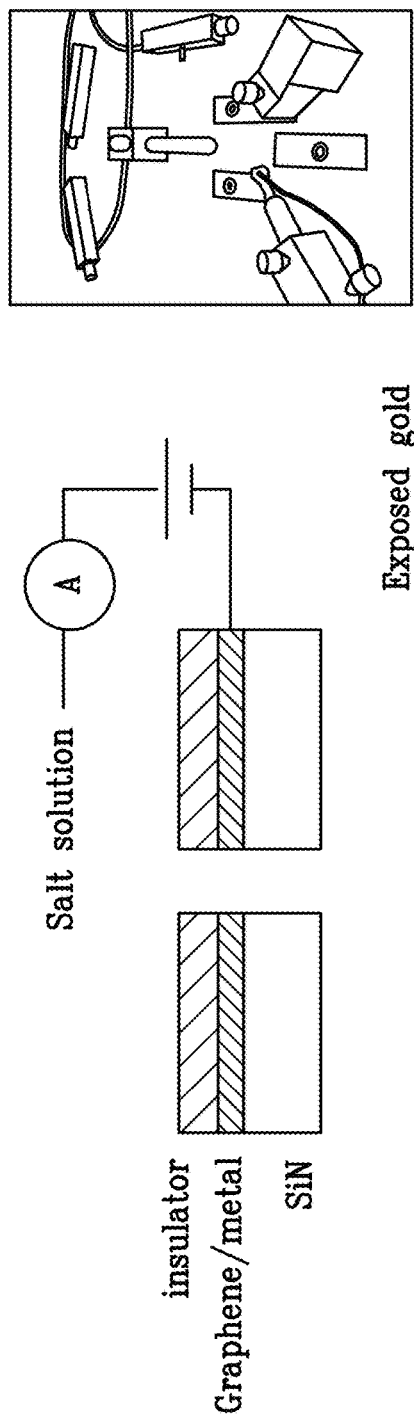
Figure 54:
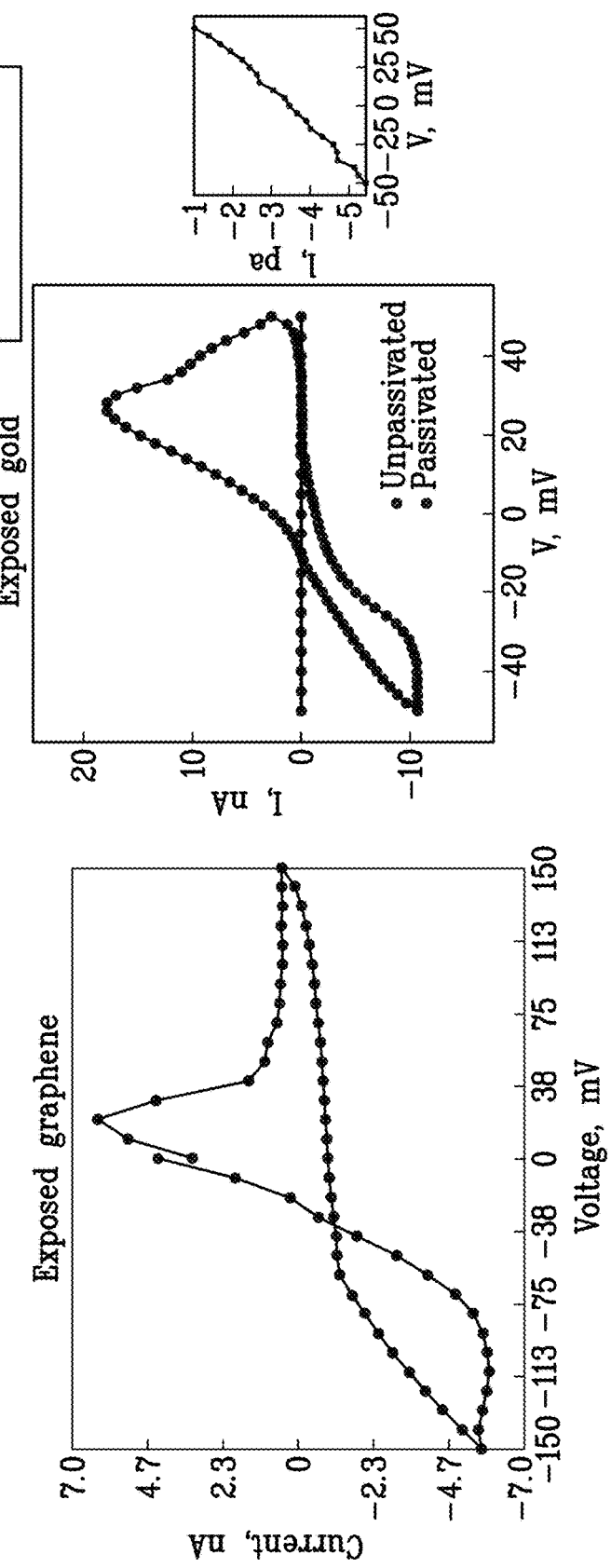
Figure 55:
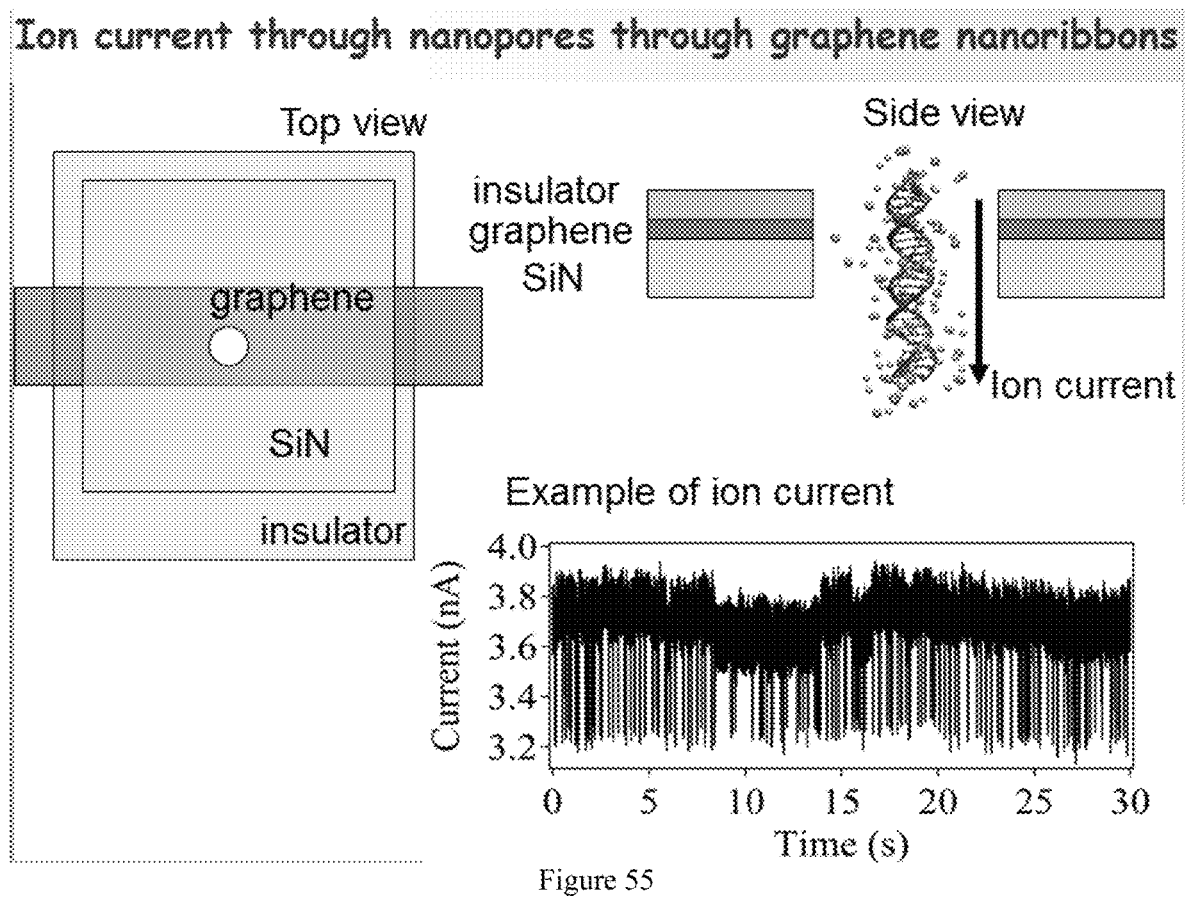
Figure 56:
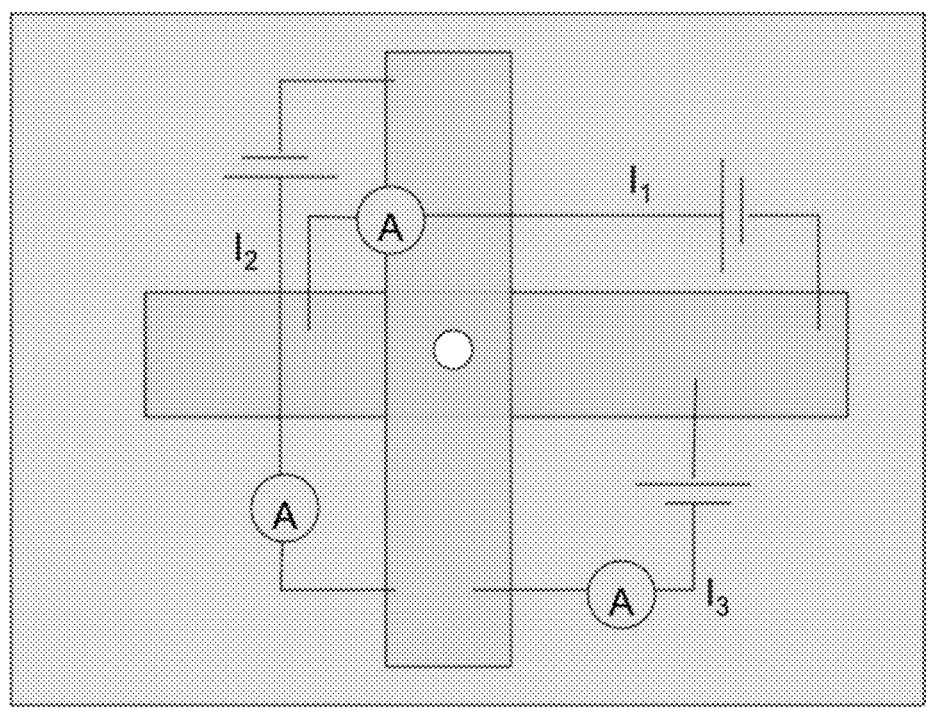
Figure 57:
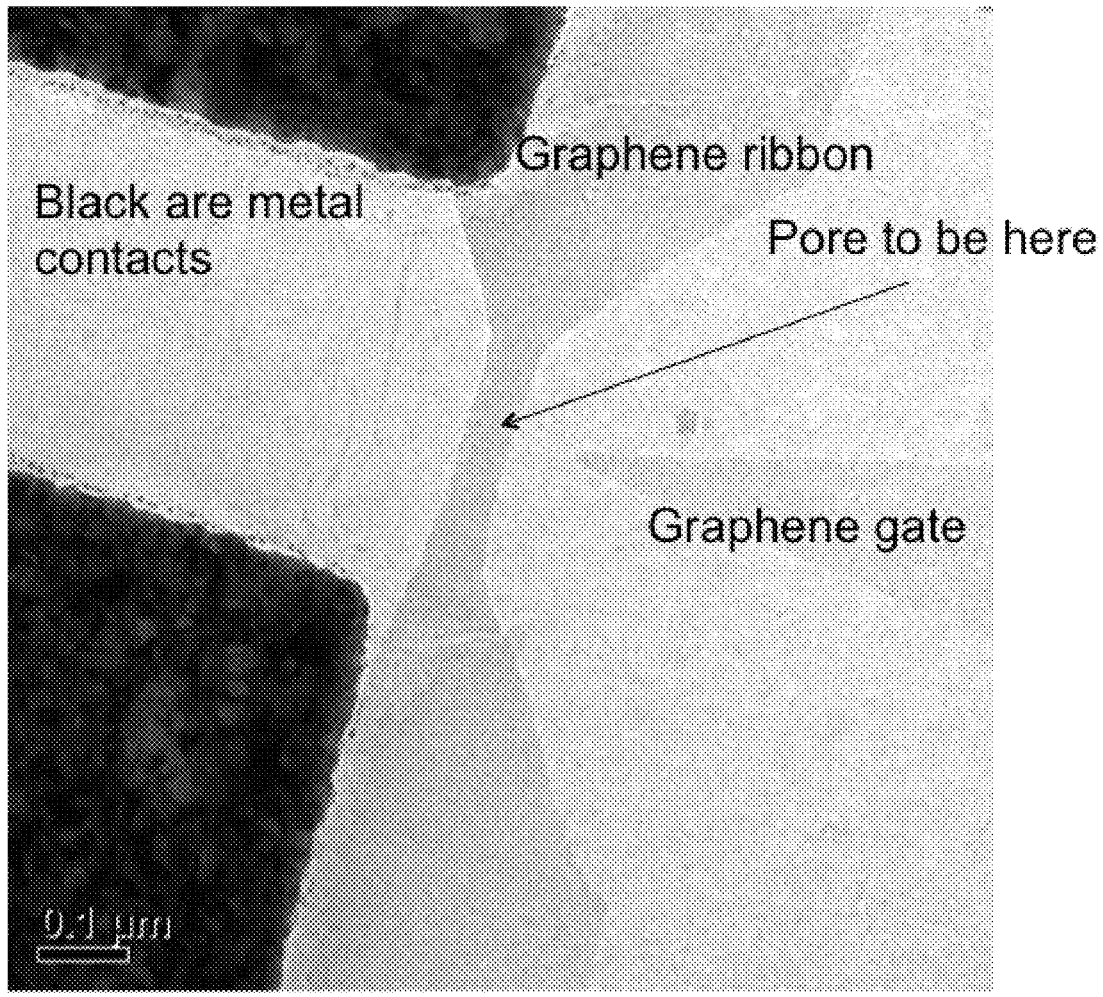
Figure 58:
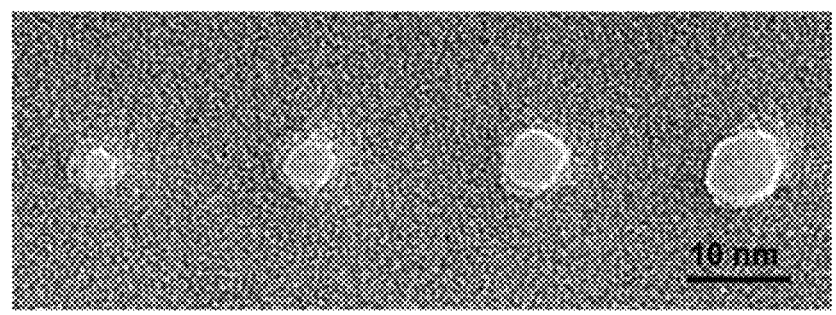
Figure 59:
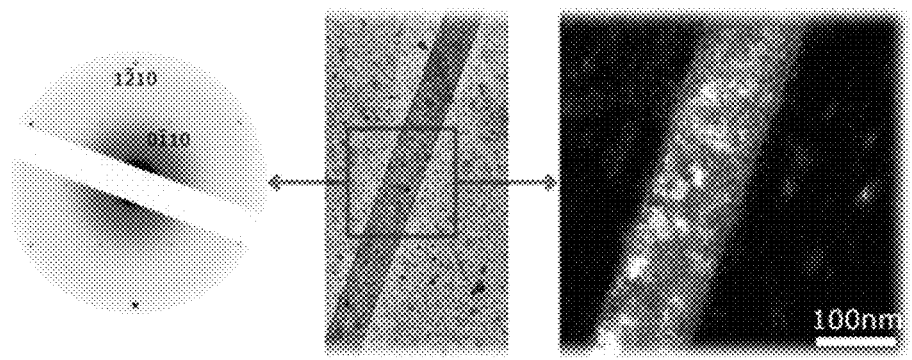
Figure 60:
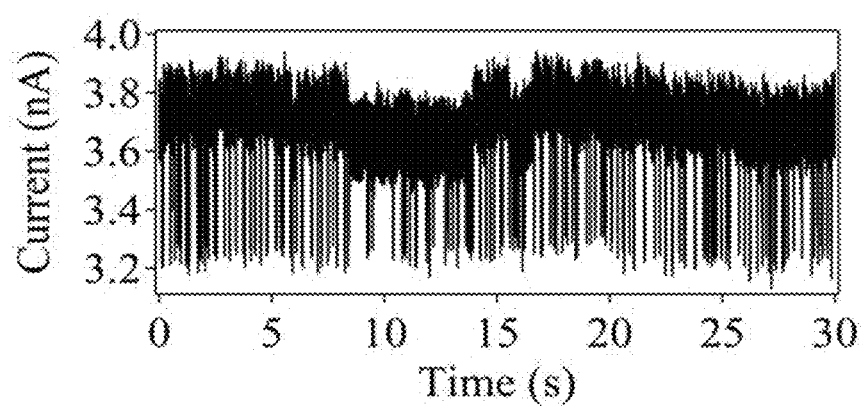
Figure 61:
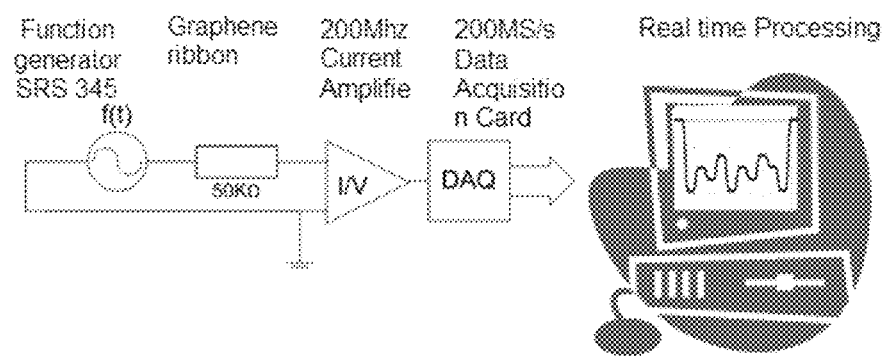
Figure 62:
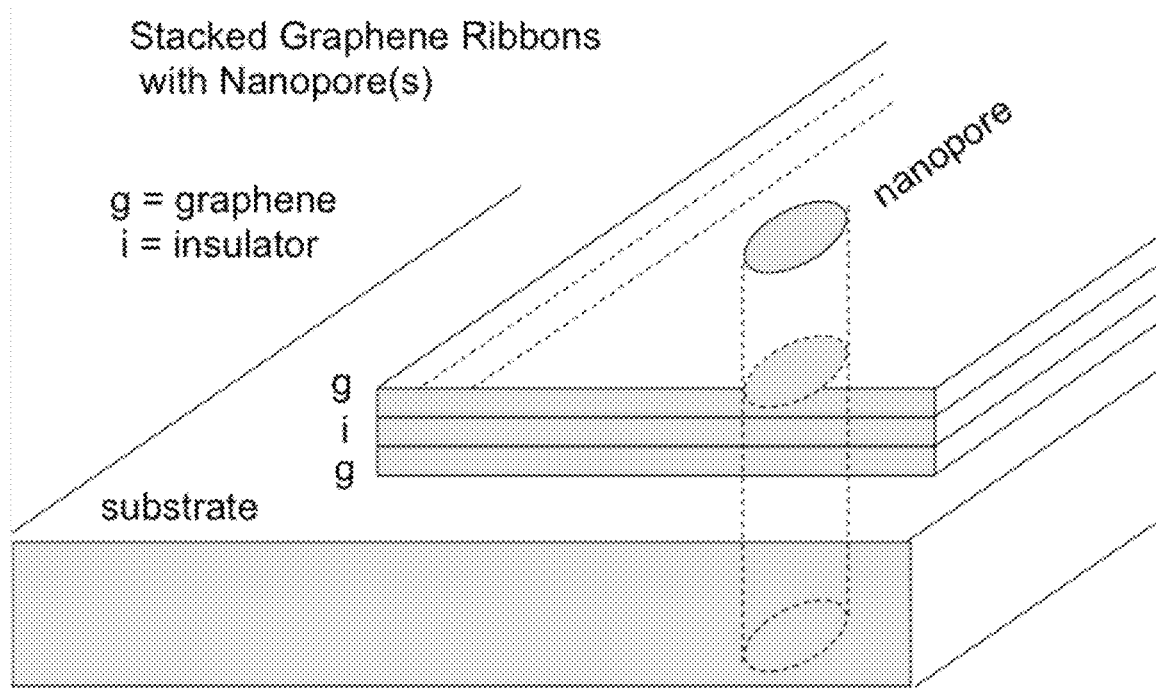
Figure 63:
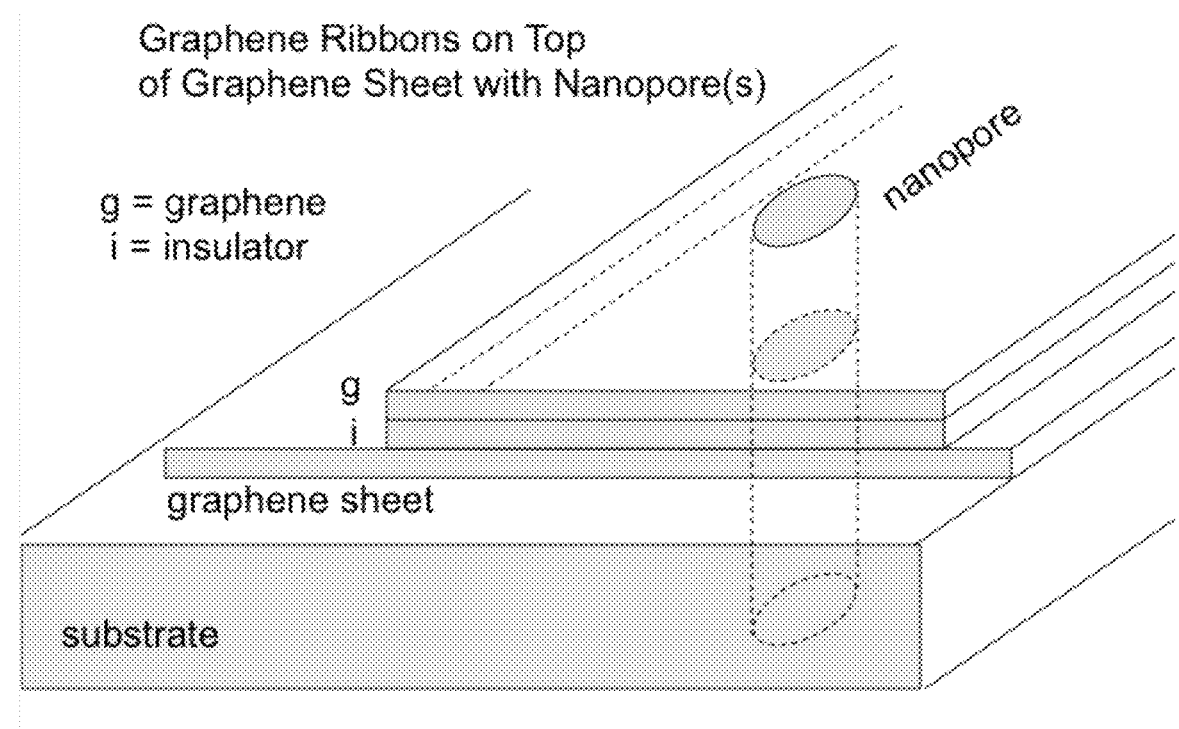
Figure 64:
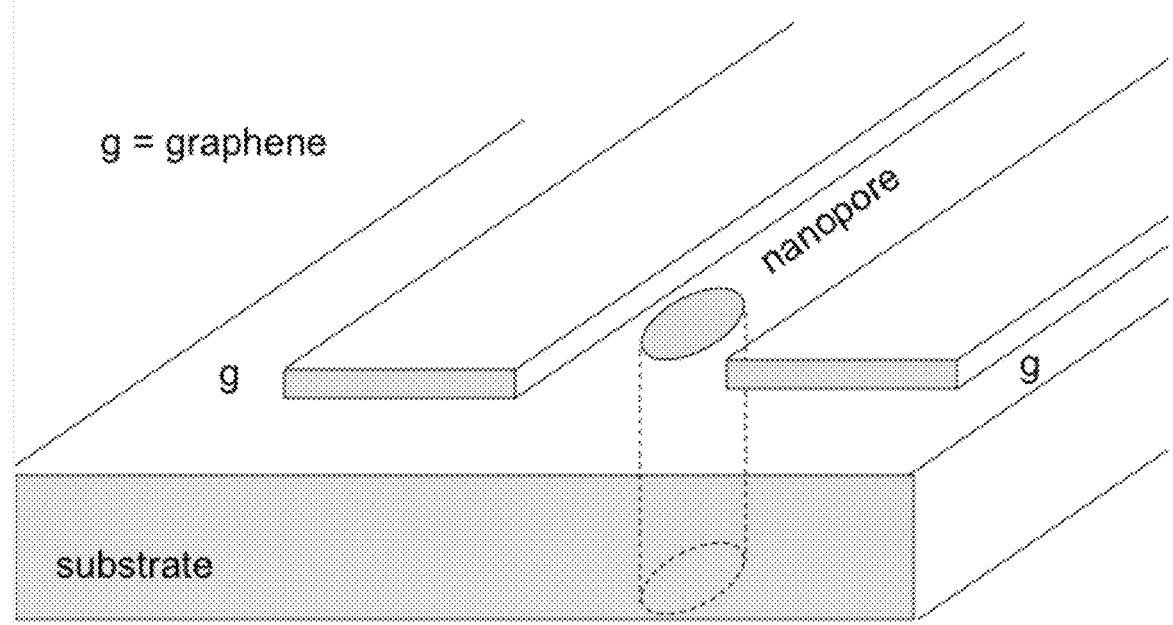
Figure 65:
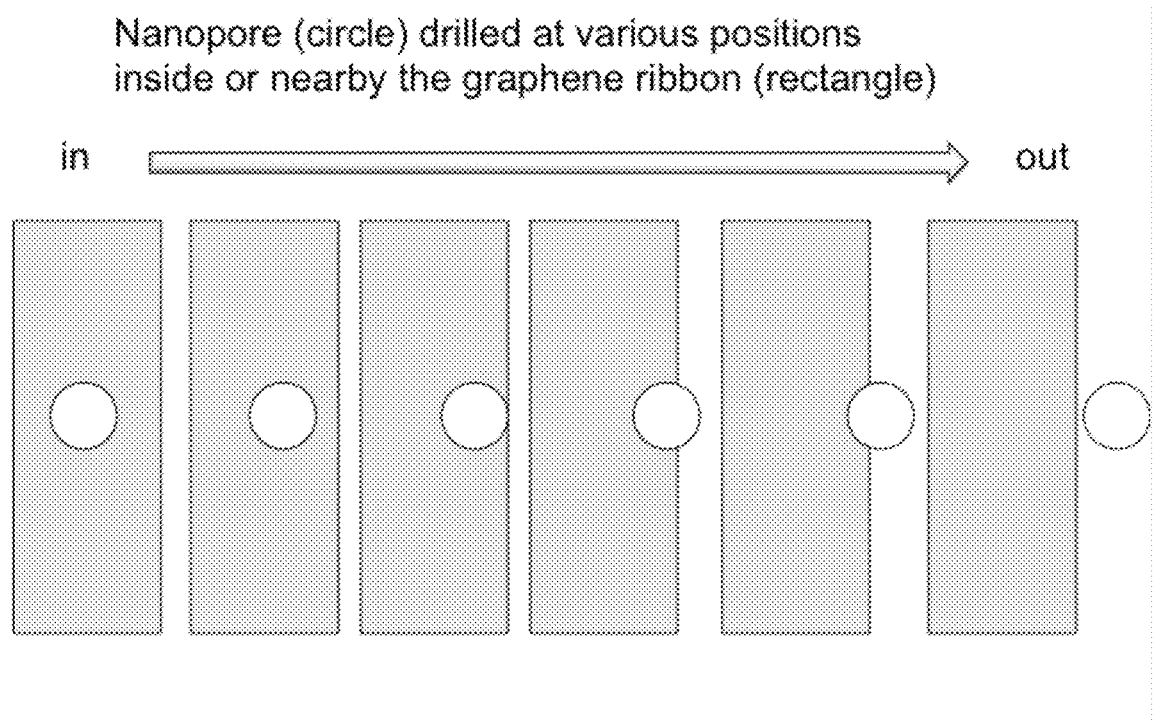
Figure 66:
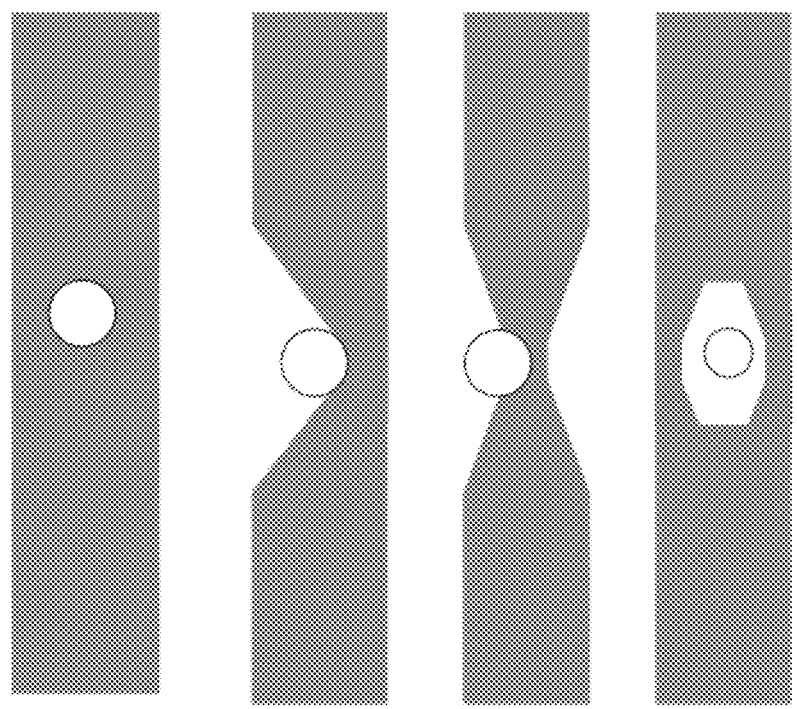

FIG. 37 illustrates an exemplary embodiment of a graphene-based device featuring anti-static discharge strips;

FIG. 38 illustrates an exemplary embodiment of a device featuring anti-static discharge strips;

FIG. 39 illustrates magnified views of graphene ribbons in electronic contact with metal contacts;

FIG. 40 illustrates a magnified view of a graphene ribbons in electronic contact with metal contacts. A small white region in the image is a nanopore drilled next to the nanoribbon;

FIG. 41 illustrates devices according to the present disclosure, featuring anti-static discharge strips. The wafer shown consists of 9 regions containing metal electrodes and deposited graphene. These 9 regions are next cleaved into 9 separate chips;

FIG. 42 illustrates a pore formed in multilayered, terraced graphene;

FIG. 43 illustrates a schematic of a coated pore formed in graphene;

FIG. 44 illustrates a schematic of a device formed from alternating graphene and insulator layers. Each graphene layer can be independently electrically contacted to apply independent voltage signals, or measure electrical current through each layer, or across layers;

FIG. 45 illustrates a device that includes a relatively small area of suspended graphene over a hole formed in a SiN layer to minimize electrical noise;

FIG. 46 illustrates a device comprising pores formed in suspended graphene and SiN layers. The hole in SiN is only slightly larger than the hole in graphene;

FIG. 47 illustrates (left image in the) a hole formed in a SiN membrane (formed by TEM) and (right image in the figure) a graphene pore in single layer graphene suspended on top of a ~20 nm large silicon nitride pore;

FIG. 48 illustrates an exemplary TEM characterization showing a hexagonal diffraction pattern of a single layer graphene forming a single-layer graphene pore;

FIG. 49 illustrates diffraction patterns for graphene samples tilted 0, 5 and 10 degrees. For samples with single layer graphene, the diffraction pattern does not change as the sample is rotated. If the diffraction pattern does change, this is an indicated that the graphene is composed of several layers;

FIG. 50 illustrates a graphene nanoribbon (GNR) contacting an insulating film and two electrodes, with a macromolecule being driven through the pore by application of a voltage. Electrical current measured includes the ion current ($I_m$) using macroelectrodes and the current through graphene ($I_n$) using nanoelectrodes shown in yellow;

FIG. 51 illustrates an exemplary fabrication method;

FIG. 52 illustrates an exemplary graphene nanoribbon device electron energy loss (EEL) spectrum (with nm spatial resolution). The sample is composed of a graphene nanoribbon on silicon nitride and the nanoribbon is covered by HSQ resist;

FIG. 53 illustrates exemplary dark field TEM imaging obtained from a graphene ribbon. This allows a determination of the mass distribution across the nanoribbon (see right panel);

FIG. 54 presents exemplary, non-limiting data concerning leakage currents after insulation. Current is measured between the macroelectrode and graphene (left panel) before putting insulation, and between macroelectrode and gold nanoelectrode (right panel). After insulation of both gold and graphene, the leakage current drops within the noise values (red line in right panel);

FIG. 55 illustrates an exemplary ion current through nanopores formed in graphene ribbons. The nanopore is made of insulator-graphene-silicon nitride;

FIG. 56 illustrates two overlapping (here, crossing) nanoribbons with a nanopore drilled in the cross section. Electrical current is monitored through each ribbon ($I_1$ and $I_2$) and across the two ribbons, $I_3$, from one ribbon to the other;

FIG. 57 illustrates an alternative embodiment with a graphene ribbon formed from single layer graphene (having a tapered region) formed thereon, and also having a side gate (triangular region on the right of the image);

FIG. 58 illustrates a TEM image of an array of nanopores drilled in order of increasing diameter;

FIG. 59 illustrates an electron diffraction pattern collected from the graphene nanoribbon;

FIG. 60 illustrates an example of ionic current vs. time measured during DNA molecule translocations through a nanoribbon-nanopore device;

FIG. 61 illustrates an exemplary data acquisition setup;

FIG. 62 illustrates an exemplary device according to the present disclosure, the device featuring stacked graphene ribbons and insulator;

FIG. 63 illustrates an exemplary device according to the present disclosure, the device featuring stacked graphene ribbon, insulator, and graphene sheet;

FIG. 64 illustrates an exemplary device according to the present disclosure, the device featuring graphene ribbons situated nearby to one another;

FIG. 65 illustrates an exemplary device according to the present disclosure, the device featuring nanopores drilled in various positions relative to a graphene ribbon; and FIG. 66 illustrates an exemplary device according to the present disclosure, the device featuring nanopores drilled in various positions relative to graphene ribbons of various conformations.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range. Any and all documents cited in this application are incorporated herein by reference in their entireties for any and all purposes.

In a first embodiment, the present disclosure provides devices. These devices include a first graphene sheet having at least one pore extending therethrough (or, in some embodiments, nearby to the graphene sheet), a membrane contacting the first graphene sheet, the membrane having an aperture in register with the pore of the first graphene sheet, and the pore having a characteristic cross-sectional dimension in the range of from about 0.1 nm to about 10 nm, about 100 nm, about 1000 nm, or even about 10,000 nm. The devices may be constructed such that although there may be a pore formed in a membrane that does not also extend through a graphene sheet or ribbon (e.g., FIG. 20c, FIG. 64) or extends only partially through the graphene (e.g., FIG. 65, FIG. 66), the device may be configured such that a signal (e.g., voltage, current) related to the passage of a macromolecule though the pore may be detected by the graphene.

The graphene sheet may be circular or square. Alternatively, the sheet may have the form of a strip, ribbon, bow-tie, constriction, or any combination thereof. Various graphene form are shown in figures A first graphene sheet may have a thickness in the range of from about 0.1 nm to about 30 nm. Alternatively, the first graphene sheet may have from 1 to about 50 layers of graphene.

A membrane may be made from silicon nitride, silicon oxide, boron nitride, aluminum oxide, hafnium oxide, titanium oxide, borosilicate glass, quartz, and the like. Combinations of materials may also be used to make suitable membranes. One exemplary device is shown in FIG. 50, which figure illustrates a graphene nanoribbon (GNR) contacting an insulating film and two electrodes, with a macromolecule being driven through the pore by application of a voltage to macroelectrodes located above and below the pore.

The device may suitably include first support material that contacts the membrane, the first support material comprising an aperture in register with the pore of the first graphene sheet. A first support material suitably has a thickness in the range of from about 0.1 nm to about 5 mm. Silicon nitride, silicon oxide, boron nitride, aluminum oxide, hafnium oxide, formvar, titanium oxide and the like are all suitable support materials.

The device may also include a base material that contacts the first support material, the base material comprising an aperture at least partially in register with the pore of the first graphene sheet. The base material may have a thickness in the range of from about 0.1 nm to about 5 mm. Silicon, silicon oxide, fused silica, quartz, borosilicate glass, and the like are all suitable base materials, as are other materials known to those of skill in the art.

Devices may include a reservoir in fluid communication with the pore of the first graphene sheet. The reservoir may contain an electrolyte fluid. The devices may also include a voltage source capable of applying a voltage across the pore of the first graphene sheet, and may also include a current amplifier capable of measuring the ionic current flowing through the pore in the first graphene sheet. As described elsewhere herein, the graphene sheet may be circular, square, a ribbon, a strip, a trapezoid, or virtually any other profile. The graphene sheet may have a cross-sectional dimension (e.g., width) in the range of a few Angstroms (1 Angstrom=0.1 nanometers), few nanometers, tens of nanometers, hundreds of nanometers, micrometers, tens of micrometers, hundreds of micrometers, or even in the range of millimeters or even centimeters, depending on the needs of the user.

Suitable devices also include a voltage sensor capable of measuring the voltage on the first graphene sheet. A device may also include a voltage source capable of applying a voltage to the first graphene sheet, a current amplifier capable of measuring the current flowing through the first graphene sheet, and also a meter capable of measuring the voltage flowing through the first graphene sheet.

Devices may also include a first amount of an insulating material (which may be organic or inorganic) surrounding at least a portion of the first graphene sheet, through which insulating material the pore of the first graphene sheet extends. The insulating material may include silicon oxide, silicon nitride, aluminum oxide, titanium oxide or even combination thereof. It should be understood that the graphene may contact an insulating material on one or both sides (which may be the same or different insulating materials). For example, graphene may contact a SiN membrane with the pore drilled through both materials. Alternatively, graphene may be surmounted by HSQ (hydrogen silsesquioxane) on one side. In other words, at least a portion of a first side of the first graphene sheet may be surmounted by the first insulating material, and at least a portion of a second side of the first graphene sheet is surmounted by a second material.

An insulating material may have a thickness in the range of from about 0.1 nm to about 1000 nm, or from 10 nm to about 50 nm. The insulating material may have a thickness of from 1 to about 20 atomic layers.

In some embodiments, at least a portion of an interior wall of the pore of the graphene sheet is surmounted by the insulating material.

Insulating material may be disposed between the first graphene sheet and a second graphene sheet, the second graphene sheet comprising a pore at least partially in register with the pore of the first graphene sheet. A user may construct devices that feature "sandwich" or other layered construction, where a graphene sheet or ribbon is disposed between two insulating layers. An insulating layer may, alternatively, be disposed between two graphene structures (ribbons, sheets, flakes, and the like). Pores in the insulating materials may be in at least partial register with pores formed in the graphene. In this way, a user may construct a multi-layered device that includes alternating layers of graphene and insulating material, if desired. Boron nitride is considered an especially suitable material for use as an insulating material, particularly between graphene sheets. In some embodiments (e.g., FIG. 42), the devices may comprise multiple layers of graphene in contact with one another. For example, a user may construct a device having 2, 3, 4, 5, 10, or even more layers of graphene. As shown in FIG. 42, layers of graphene need not each contain the same size pore, as a set of graphene may contain a terraced configuration.

FIG. 44 illustrates an exemplary, layered graphene nanopore structure. As shown in the figure, the device may include several graphene layers separated by insulators. Any of the graphene and insulator layers may be patterned; for example, the bottom-most graphene can be a sheet (voltage 1), while graphene above that can be patterned as a ribbon—in this case, the bottom graphene sheet may be used a global gate to affect the conductance of the ribbon above. Different voltages may be applied to different layers in the structure.

As described elsewhere herein, boron nitride is considered an especially suitable insulator material. Boron nitride is an excellent insulator, and is also formed into flat configurations, and can be grown by chemical vapor deposition (CVD) similarly like graphene; because it can be formed into flat configurations and easily manufactured, boron nitride may be considered an ideal insulator in between graphene layers to make sure that the graphene layers are flat (no wrinkles). Boron nitride can be grown like graphene, and may in fact be made atomically thin like graphene. Pores may be formed in boron nitride that are as thin as graphene and, in some embodiments, may be used for DNA sequencing like graphene. The use of boron nitride nanopores is particularly useful in applications where it is desired that the nanopore material is insulating.

Devices may also include a second amount of insulating material in contact with the second graphene sheet. Devices may further include a third graphene sheet in contact with the second amount of insulating material.

In some embodiments, at least a portion of the graphene sheet includes graphene annealed by application of an electric current or by thermal annealing. A graphene sheet in the disclosed devices may have a resistivity in the range of from about 1 k-ohms to about 2 M-ohms, or even in the range of from 0.00000005 ohm-cm to about 0.36 ohm-cm. In certain embodiments using annealed graphite, an ionic current noise passing through the graphene sheet pore is reduced relative to the ionic current noise passing through a graphene sheet pore free of annealing.

Also provided are methods of analyzing a sample. These methods suitably include translocating at least a portion of a macromolecule through a pore extending through a graphene sheet; collecting a signal related to the translocation; and correlating the signal to a structural characteristic of the macromolecule.

In some embodiments, the graphene sheet is at least partially surmounted by an amount of insulating material through which amount of insulating material the pore extends. Translocating may be affected by applying a gradient across the pore so as to translocate the macromolecule. Such gradients include an electrical gradient, a pressure gradient, a chemical gradient, or any combination thereof. Electrical signals are considered especially suitable for monitoring. The monitored electrical signals include: ionic current through the nanopore, current through a graphene layer, or current across two nearby graphene layers.

The methods may further include application of a voltage to the graphene sheet so as to effect movement of at least a portion of the macromolecule. The user may also apply a voltage so as to restrain movement of at least a portion of the macromolecule. The graphene sheet may be at least partially surmounted by an insulating material. The amount of voltage applied to the graphene to affect the motion of the DNA depends on salt concentration. For higher salt concentrations (for example, 1 Molar or 3 Molar), the ions can efficiently screen the electric field generated by the graphene and therefore one may apply higher voltages to the graphene in order to affect DNA motion. Inversely, for low salt concentrations (e.g. 1 mMolar, 10 mMolar), the motion of DNA can be affected by applying lower voltages to graphene;

Also provided are methods of fabricating devices. These methods suitably include disposing a graphene sheet atop a membrane having an aperture formed therethrough such that a pore extending through or nearby the graphene sheet is in register with the aperture of the membrane. It should be understood that a nanopore may be formed nearby—but not necessarily entirely within—a graphene sheet or ribbon. The pore may in fact be at a distance from an edge of the graphene sheet, e.g., about 0.1, 1, 5, 10, 15, 20, 50, or even 100 or 200 or more nanometers.

The devices and methods may, as described elsewhere herein, be constructed such that a user detects one or more signals (e.g., an electrical signal, an ion current, and the like) related to the passage of a macromolecule through a nanopore. The signal may be detected in a graphene body (e.g., sheet, ribbon, and the like). The nanopore may be formed in the graphene body, but need not necessarily be so formed. For example, the user may detect a signal in the graphene that is related to macromolecule translocation through a pore in the graphene. Alternatively, the user may detect a signal in the graphene that is related to macromolecule translocation through a pore in a membrane or other support material (which may contact the graphene), where the pore does not extend through the graphene, as shown in, e.g., FIG. 64. The devices may include multiple graphene bodies (e.g., sheets, ribbons), as shown in FIG. 64.

The methods may further include forming the pore in the graphene sheet. The user of skill in the art will be familiar with suitable such methods. A pore may be formed by transmission electron beam ablation lithography (TEBAL). Exemplary techniques are describe in U.S. Pat. No. 8,173,335, "Beam Ablation Lithography," issued May 8, 2012, the entirety of which is incorporated herein by reference for all purposes.

The method may further include application of a voltage to the graphene sheet. The voltage is suitable in the range of from about 10 mV to about 10 V. Voltage may be applied for from about 0.1 seconds up to about 12 hours. The user may also dispose an insulating material along the graphene sheet. The insulating material is suitably disposed on at least a portion of both sides of the graphene sheet, and may be disposed using atomic layer deposition.

A pore is suitably formed in the graphene sheet after disposition of the insulating material, although the pore can be formed before disposition of the insulating material. The user also suitably forms an aperture through the membrane, which aperture is suitably in register with a pore of the graphene sheet. Forming the aperture is suitably effected by electron beam lithography, ion beam lithography, plasma etching, or any combination thereof. The user may also form an aperture through a first support material contacting the membrane, and may also form an aperture through a base material contacting the first support material. Apertures are suitably formed by electron beam lithography, ion beam lithography, plasma etching, or any combination thereof. The user may also irradiate the graphene sheet with ultraviolet light, contact the graphene sheet with ozone, contact the graphene sheet with oxygen plasma, or any combination thereof.

Additional methods for constructing a device are also provided. These methods include applying a voltage to a graphene sheet having a pore formed therethrough or nearby, the voltage being in the range of from about 1 mV to about 10 V. The voltage may be applied for from about 0.1 seconds to about 12 hours. The graphene sheet may be, as described elsewhere herein, from 1 to about 50 atomic layers in thickness.

In an alternative embodiment, a user may thermally anneal a graphene sheet having a nanopore extending therethrough or nearby. This annealing may be application of from 30 deg C. to 2000 deg. C., for from 5 seconds to 12 hours.

In this disclosure is provided the first experimental realization of DNA translocation through graphene nanopores, which is the first step towards exploring the potential applications of this new membrane material. This disclosure shows that the ionic blocked current signatures from DNA translocations through sub 10-nm graphene nanopores compare favorably with similar diameter SiN nanopores. It is also observed that the current signal from bare graphene nanopores where graphene sheets are relatively large (millimeters in size) is consistently noisier than for SiN nanopores, and the DNA translocation signals reveal non-uniform current amplitudes. The large noise is attributed to the presence of pinholes in the graphene membranes as well as incomplete wetting, and higher capacitance due to the larger graphene sheet area. Atomic layer deposition (ALD) of several nanometers of oxide over the devices consistently reduces the nanopore noise level and improves the mechanical robustness of the device. This process preserves electrical addressability of the nanopore, which may be useful for realizing both multilayer graphene-insulator nanopores and graphene nanogap devices.

Figure 1:
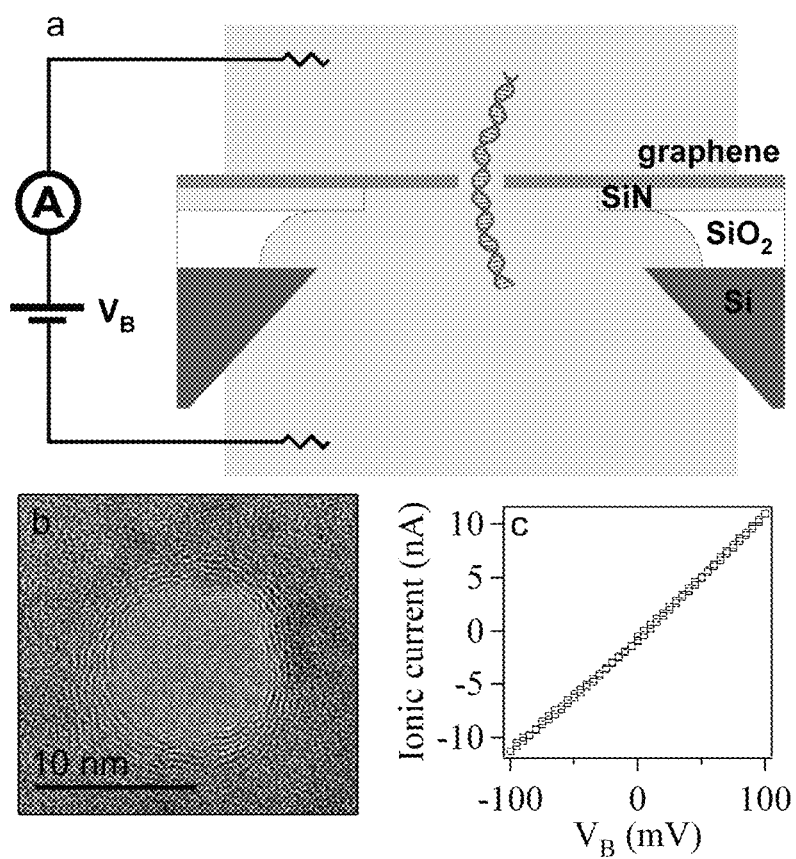
FIG. 1. Graphene nanopore devices. (a) Device schematic. Few-layer graphene (1-5 nm thick) is suspended over a 1 μm hole in a 40 nm thick silicon nitride (SiN) membrane. In such embodiments, the aperture formed in the SiN (or other) membrane is larger in cross-sectional dimension than the pore formed in the graphene. In some embodiments (e.g., FIG. 63), a graphene sheet or ribbon may sit directly atop a SiN substrate, in which case the pore formed in the graphene and the pore in the SiN has the same cross-sectional dimension. Graphene sheets (and ribbons) may have an area of about 31400 $nm^2$, 314 $nm^2$, or smaller, depending on the user's needs. The SiN membrane is suspended over an approx. 50×50 $\mu m^2$ aperture in a silicon chip coated with a 5 μm $SiO_2$ layer. Apertures may have a cross sectional dimension (not shown) in the range of from 1 nm to about 100 micrometers, or from about 50 nm to about 100 micrometers, or from about 100 nm to about 10 micrometers, or from about 500 nm to about 1000 nm. An exemplary embodiment is shown in FIG. 45, which figure shows a graphene sheet atop a SiN membrane. The SiN material has a pore (or aperture) formed therein, and at least a portion of the graphene is suspended above the SiN aperture. The graphene material in turn has its own pore formed therein, the graphene's pore being in register with the aperture of the SiN. The cross-sectional dimension of an aperture may differs from the cross-sectional dimension of the pore by less than about 5 nm. In some embodiments, a graphene body (e.g., sheet or ribbon) has a cross-sectional dimension that is larger than a cross-sectional dimension of the aperture by less than about 20 nm. A graphene sheet may have a cross-sectional dimension that is larger than a cross-sectional dimension of the aperture by less than about 10 nm.

A schematic of a typical graphene nanopore device is given in FIG. 1*a*. Silicon chips covered with 5-micrometer SiO$_2$ and 40 nm silicon nitride are etched so that freestanding nitride membranes of approximately 50 micrometer square remain. Electron beam lithography (EBL) followed by an SF$_6$ plasma etch is used to pattern a ~1-micrometer hole through the nitride membrane. Ion beam processes may also be used.

Graphene is grown by the chemical vapor deposition (CVD) of methane over polished copper foils, as detailed in FIG. 6. The copper foils are etched in solution so that bare graphene sheets, approximately 0.3-5 nm thick (1-15 monolayers), shown in FIG. 7, float on the surface of the liquid. Suitably-sized graphene sheets, larger than 2 mm×2 mm, are then scooped onto the pre-patterned silicon nitride membranes, as shown in FIG. 8. In this way the graphene is structurally supported by the nitride membrane, with only a limited area freely suspended over the 1-micrometer hole. Nanopores are then drilled through the suspended graphene membranes by transmission electron beam ablation lithography (TEBAL). Here was used CVD graphene, rather than exfoliated, because the cm-scale sheets are easy to manipulate and the process is scalable for future applications. It has been observed that graphene is very hydrophobic, and one finds that a rapid UV/ozone treatment improves the wetting properties of graphene nanopores, allowing ion transport through the nanopore. All devices underwent at least five minutes of UV/ozone treatment immediately prior to assembly in a PDMS measurement cell and exposure to electrolyte. One measurement cell features microfluidic channels that form reservoirs in contact with either side of the chip. Using a pair of Ag/AgCl electrodes, a bias voltage, $V_B$, is applied between the two reservoirs to drive ionic current through the nanopore.

A TEM image of a representative nanopore drilled into a suspended graphene membrane is given in FIG. 1b. The visible rings around the pore are from graphene edges, and their number provides an estimate of the graphene membrane thickness. FIG. 1c shows a typical measurement of the ionic current through a graphene nanopore as a function of the applied voltage, $V_B$. One finds that graphene nanopores with diameters ranging from 5 to 15 nm exhibit a wide range of conductance values between ~20 and 1000 nS (see FIG. 9). This wide conductance range does not correlate with nanopore size, and cannot be explained by membrane thickness variations, which suggests that ions are able to flow through pinholes in the graphene membranes. UV/ozone treatment of graphitic material, such as carbon nanotubes (CNTs), has been shown to induce defects by an oxidative reaction. Electron beam irradiation has also been shown to affect the properties of carbon-based materials and induce defects. Without being bound to any single theory, it is possible that UV/ozone treatment and/or electron beam irradiation forms occasional pinholes membranes, though they are not readily visible under TEM observation. The measurements highlighted in FIG. 10, indicate that UV/ozone treatments create defects in graphene, which increase the electrical resistance of these sheets over time. These pinholes do not hinder the ability of the devices to measure DNA translocation through the fabricated nanopores. The pinholes are too small for the DNA to pass through, so that the ion current through the pinholes simply adds in parallel with the primary nanopore current, as illustrated in FIG. 11. FIG. 55 also shows an exemplary ion current through nanopores formed in graphene ribbons, with a layer structure of nitride, graphene, HSQ (silicon oxide), ALD (TiO2 or Aluminum Oxide).

It should be understood that the disclosed devices may be constructed with layered graphene and with crossed graphene pieces (e.g., crossed ribbons). One embodiment consists of two or more parallel ribbons one of top of the other, similar to what is shown in FIG. 44, where a nanopore is drilled through all the layers. This embodiment allows measurements of electrical currents through each ribbon. As DNA bases pass through the nanopore, each ribbon can give a signal verifying the passage of a particular base at a particular time. The ribbon on the top will detect a particular DNA base first, while the ribbon on the bottom of the pile will detect that same DNA base some time later. If there are N ribbons that are electrically operated, there will be N signals corresponding to the sequence of the DNA translocating through the nanopore. The comparison of these N signals allows for additional error correction in DNA sequencing, because there will be N identifications of each base and the confidence level of correctly calling the DNA bases increases. Another embodiment of layered graphene devices is a device with crossed ribbons which is illustrated in FIG. 56 with two crossing nanoribbons with a nanopore drilled in the cross section. The device may have insulation between ribbons. Alternatively, there may not be insulation between ribbons to allow for smaller spacing between them, and therefore a smaller sensing region, comparable in size to the DNA base passing through. The relative orientation of the hexagonal lattice in the two graphene layers can be completely overlapping (the two lattices are then in register), or the lattices can have random orientations relative to each other. The electrical coupling between the two ribbons depends on the relative orientation of the lattices in the bottom and top layers, and so will the magnitude of the electrical current measured between them. Thus, graphene ribbons may have hexagonal lattices that are in the same orientations (i.e., in register with one another), or may have lattices oriented at some angle with respect to each other. The lattice orientation may be modulated so as to control coupling between the ribbons. Three electrical current signals can be measured in this embodiment: the first two signals are currents through each ribbon, and the third signal is the current from one ribbon to the other, i.e. the current flowing through the cross-sectional area from bottom ribbon to top ribbon. This current flowing from bottom ribbon to top ribbon is in nature a tunneling current. All three current signals will be sensitive to single DNA nucleotides (A,C,G, T) and allow simultaneous measurement of three currents for independent verifications of the DNA base present in the nanopore at a single point in time. This means that single DNA base calling may be more accurate in this case, where each base is sampled several times. As discussed herein, two parallel (or nearly parallel) ribbons may be used, wherein one may measure the current through each ribbon. This allows a user to obtain two independent confirmations of the structure (e.g., DNA base) of the macromolecule under study. The ribbons may lie next to one another (e.g., FIG. 64) or may be stacked above one another. Thus, the disclosed devices and methods may include translocating the at least a portion of a macromolecule through a pore formed in a second graphene sheet characterized as a ribbon, and collecting a signal related to the translocation of the macromolecule through the pore formed in the second graphene sheet. Graphene bodies (e.g., ribbons) need not be parallel to one another, as shown in FIG. 64, and may be disposed at an angle (0-90 degrees) to one another.

Nanopores are suitably drilled by a TEM device. Pores may be drilled at room temperature, but may alternatively be drilled at elevated temperatures of several hundred (>300 C)

or thousand (1000-2000 C) degrees. Drilling at higher temperatures produces cleaner nanopores with fewer contaminants and defects.

A TEM image of an 8-nm diameter graphene nanopore, along with a current vs. time trace showing DNA translocation through the nanopore device, is given in FIGS. 2a and 2b. The electrolyte solution used for these measurements was 1 M KCl, 10 mM Tris, 1 mM EDTA, pH 9. One may add 15 kbp double-stranded DNA (Fermentas NoLimits®, Glen Burnie, Md.) at a concentration of 1 nM to the analyte reservoir, and applied a bias voltage of $V_B$=+100 mV to the other reservoir in order to drive DNA through the pore. The ionic current signal was filtered with a 10 kHz 3-pole Bessel filter and then sampled at 50 kHz. It is seen that the 28 nA open pore current sharply decreases by between ~500 pA and 1 nA as DNA molecules pass through the graphene nanopore. Translocation events are not observed before the addition of DNA molecules, as demonstrated in FIG. 12. The overall noise level is higher for this device than for measured silicon nitride nanopore devices (see FIG. 13), but the DNA capture rate is comparable for both nanopores (~1 event/s for 1 nM and $V_B$=100 mV). The graphene nanopore noise is dominated by a 1/f noise component, which will be discussed later. This component can be lowered by reducing the surface area of the graphene.

A histogram of the measured blocked current signal, $I_{BL}$, is shown in FIG. 2c for the device shown in FIG. 2a. Here, $I_{BL}$ is defined as $I_{BL}=<I>-<I_{open}>$, where $<I>$ is the mean pore current during DNA translocation and $<I_{open}>$ is the mean pore current 0.1 ms before DNA entry. The data in FIG. 2c has been fit with a double Gaussian with mean $I_{BL}$ values of 0.45 and 0.9. These mean values correspond to peaks in the histogram of the current data, and indicate two event populations. Examples of both populations are represented in the inset by several representative events. From these events it is seen that both folded and unfolded events comprise the two populations. The blocked current fraction (i.e., $<I_{BL}>/<I_{open}>$) is ~5 times smaller than expected based on the relative areas of the DNA molecule ($A_{DNA}$) and the nanopore ($A_p$). One may calculate an expected value of $A_{DNA}/A_p$~$(2.2\ nm)^2/(8\ nm)^2$=7.6%, compared with a measured blocked current fraction of 1.6%. Increased baseline open pore current due to pinholes is ultimately responsible for the decreased blocked current fraction. However, the magnitude of the $I_{BL}$ values are 3 times larger than measured with similarly-sized pores in 40-nm thick SiN membranes at these voltage levels. This increase in $I_{BL}$ is attributed to the thinner graphene membrane, which is ~2 nm thick in FIG. 2a. The thinner membrane decreases the overall pore resistance, therefore increasing the magnitude of the current blocked by the translocating DNA molecule.

A scatter plot of event depth as a function of event length for ~600 events measured with the same device is given in FIG. 2d. Two clear groupings of events are visible, one centered around $I_{BL}$=5 nA (unfolded) and a second centered around 1 nA (folded). A histogram of the measured event lengths for these events is given in FIG. 2e. There is a large variation in the measured event lengths with no clear average value, indicating that the peak value is likely just below the measurement threshold. Two clear populations of events are observed and have been fit with exponential functions using time constants of $\tau_1$=0.07 ms and $\tau_2$=0.5 ms. These timescales correspond to an average DNA velocity of between ~5 and 30 ns/basepair, comparable to DNA velocities through other nanopore materials.

One may note that while the results in FIG. 2 are representative measurements of DNA translocation through suspended graphene membranes, the fraction of functional bare graphene nanopores that exhibit detectable DNA translocation is small. Of the 50 bare graphene nanopore devices tested, only ~10% showed DNA translocation. From the remaining pores, 20% had hole defects visible under low-magnification TEM observation, 30% developed tears during the measurement, and 30% did not wet properly, indicated either by a conductance below ~1 nS and/or a highly non-linear and hysteretic open pore current-voltage measurement. Therefore, despite a large interest in graphene nanopores as electrically addressable ultrathin membrane materials, the low functional yield of pores limits the usability of bare graphene nanopore devices, unless methods of improving membrane stability and wettability are realized.

To address the low yield, one may deposit a few-nm on insulation, $TiO_2$ layer in this case, on both sides of the graphene membrane using atomic-layer deposition. $TiO_2$ was chosen because of its excellent wettability with aqueous solutions and superior bonding to graphitic material. ALD has been previously shown to reduce the overall nanopore noise level (particularly the low-frequency, 1/f component), presumably by generating a cleaner, more easily wettable surface. An ionic current-voltage measurement of a 10-nm diameter nanopore in graphene coated with 5-nm $TiO_2$ is shown in FIG. 3a, along with a TEM image of the nanopore inset. Following the formation of nanopores, one may observe crystallization of the $TiO_2$ proximal to the nanopore, as previously observed with nanopores in ALD alumina membranes. The coverage of the graphene membranes with $TiO_2$ appears conformal based on TEM observation, as shown in FIG. 14. The addition of $TiO_2$ does not systematically change the magnitude of the open pore current relative to uncoated devices because $TiO_2$ is not a good barrier to pinhole formation from either electron-beam irradiation or UV/ozone treatment.

Representative power spectral densities (PSD) of open pore current traces are shown in FIG. 3b for several devices: a 7.5 nm diameter graphene pore, an 8-nm diameter graphene-$TiO_2$ pore, and a 6-nm diameter SiN pore. The overall noise level is typically higher for graphene devices (in this case the graphene sheet area is very large) than for SiN nanopores tested in the same measurement cell. Particularly, the 1/f noise component is especially large for bare graphene devices, extending to the ~10 kHz frequency range with an exponent of ~1, as compared with 10-100 Hz for silicon nitride pores. Oxide-covered devices have a reduced noise level relative to bare graphene devices, especially in the low-frequency regime. This is attributed to the improved hydrophilicity of the $TiO_2$ surface. It is observed that the current noise for both bare and $TiO_2$ coated nanopore devices increases with the open pore current (see FIG. 9). Noise due to a large capacitance in the device (from the large graphene sheet) converts the measurement amplifier's voltage noise into current noise, which typically dominates at higher frequencies. Of all the devices measured, the graphene-based devices had a higher capacitance than the SiN devices. The capacitance is higher for graphene because the conductive graphene sheet is capacitively-coupled to the electrolyte solution. As a result, the entire 5 to 10 mm$^2$ graphene area forms a capacitor across the SiN and $SiO_2$ layers to the underlying silicon and electrolyte. Reducing this area, reduces the noise accordingly as well. Although the 50×50 μm$^2$ SiN membrane is far thinner than the rest of the chip, it does not dominate the capacitance because its area is ~1000 times smaller than a typical graphene sheet. In FIGS. 46 and 47 are shown graphene sheets that are several orders of magnitude smaller in area, where this noise has been minimized. Thus, the present disclosure provides methods for constructing a device having improved signal-to-noise characteristics. These methods may include applying a voltage to a graphene sheet having a pore formed therethrough (or nearby to the graphene sheet). The voltage may be in the range of from about 10 mV to about 10 V. The graphene sheet may be from 1 to about 50 atomic layers in thickness. The graphene sheet may, in some embodiments, have an area of less than about 31400 nm$^2$.

Example time traces for DNA translocation through three $TiO_2$-coated graphene nanopore devices are given in FIGS. 4a-c. TEM images of the nanopores that range in diameter from 5.5 to 8 nm, and concatenated sets of translocation events for each nanopore, are inset. The open pore currents for graphene-$TiO_2$ nanopores do not scale with pore size, ranging from ~2 to 100 nA at 100 mV. As with bare graphene devices, one may attribute this variation in open pore currents to a randomly varying pinhole density between samples. The same process was consistently used to fabricate all devices, so process variations are unlikely to explain the differences in pinhole density. The variations are likely a consequence of quality differences between graphene membranes, which can be improved by controlling the submicron structure of the copper foils on which the CVD graphene is grown. The nanoscale differences in graphene grain structure likely influence the rate of formation of pinholes during the TEBAL and/or UV/ozone steps of the device fabrication process. High quality graphene is shown to have improved uniformity of open pore currents.

The data in FIGS. 4a and 4b show translocation of 15 kbp dsDNA through (a) a 7.5-nm and (b) a 6-nm graphene-$TiO_2$ nanopore. A similar capture rate was observed when compared with bare graphene and SiN nanopores. $I_{BL}$ values between 200 and 400 pA were observed at $V_B$=100 mV for these two devices. Also measured was the translocation of much shorter 400 by dsDNA (Fermentas NoLimits®, Glen Burnie, Md.), as shown in FIG. 4c. Here, mean $I_{BL}$ values of over 1 nA are measured for $V_B$=150 mV. Translocation events for two different DNA lengths, 400 bp and 3000 bp, are additionally shown in FIG. 15. The amplitude of folded entry (~1.6 nA) is approximately double the amplitude of unfolded entry (~0.8 nA), and the appearance of a large fraction of folded and unfolded translocations is in line with previous measurements in solid-state membranes. Despite the baseline nanopore current level increasing from FIGS. 4a to 4c due to pinholes in the membrane, the functionality of the devices does not appear to be adversely affected. This is suggested by the similar range of $I_{BL}$ depths for the devices shown in FIG. 4, from ~500 pA to 1.5 nA, even for devices with two orders of magnitude difference in open pore current, from ~2 nA to 100 nA.

In FIG. 5, two-dimensional histograms of event length as a function of $I_{BL}$ are given for 15 kbp dsDNA through a 6-nm graphene nanopore device at $V_B$=(a) 100 mV and (b) 400 mV. The device was coated with 5 nm $TiO_2$, and 1,100 and 1,800 events were collected and analyzed for (a) and (b), respectively. There are two clear regimes visible in FIG. 5a. Unfolded events are clustered around 200 pA and folded events are clustered around 400 pA, with a mean unfolded event length of ~200 microseconds. This corresponds to a translocation speed of 70 bases/microseconds. The events depicted in FIG. 5b are faster and deeper as expected due to the increase in $V_B$. One measures an average $I_{BL}$ of 1.3 nA at $V_B$=400 mV and a decreased mean translocation time of ~100 microseconds. This is the minimum pulse duration measured with the 10 kHz filter in the experimental setup, so the actual translocation time may be shorter.

From the histogram in FIG. 5a, there is a clear peak in the blocked current at 200 pA for an applied bias voltage of 100 mV. Though the magnitude of $I_{BL}$ is large, based on this device's open pore current of 10 nA, one may calculate that the blocked current accounts for only 2% of the open pore current. This is one order of magnitude lower than the expected $I_{BL}$ of 13% for SiN nanopores based on pore diameter, further supporting the existence of pinholes in the membrane which increase the baseline open pore current signal. FIG. 5c shows the mean $I_{BL}$ as a function of the applied bias voltage for the same device. The magnitude of the blocked current increases linearly with $V_B$, as previously observed in SiN pores for DNA in the voltage regime tested.

Mean translocation velocity, $v_{DNA}$, is plotted in FIG. 5d as a function of $V_B$. One may observe that the translocation velocity increases linearly with increasing applied bias voltage, as has been observed in SiN nanopores. Mean velocities, $v_{DNA}$, are calculated by fitting histograms of the measured event lengths at a given $V_B$, and calculating velocity as the length of the molecule (in bases) divided by the mean event length (in seconds). The event length histograms used to compute $v_{DNA}$ are given in FIG. 16. A histogram of the wait time between consecutive events is given in FIG. 5e for $V_B$=100 and 400 mV. In both cases the wait time follows a Poissonian distribution, indicative of the uncorrelated nature of the translocations. Wait time decreases with increasing voltage because the distance from the pore at which DNA molecules are captured by the electric field increases with voltage In summary, presented are electronic measurements of DNA translocation through graphene nanopores. The ionic current blocked by DNA translocation through graphene nanopores is larger than what has been observed for SiN nanopores of the same diameter, due to the thinness of the graphene membrane.

Device improvement may also be realized through forming smaller holes in the supporting membrane (e.g., SiN) to minimize the area of the graphene that is suspended above the hole. As one example, a user may form a hole in a SiN or other support membrane having a diameter in the range of from about 5 nm to about 50 nm, or even in the range of from about 10 nm to about 20 nm. Reducing the size of the hole in the support membrane in turn acts to reduce the amount of graphene membrane suspended over that hole. In one embodiment, a SiN membrane may have a hole formed therein in the range of from about 18 nm to about 22 nm, which hole in turn supports a graphene membrane that has a pore with a diameter in the range of about 1.1 nm to about 5 nm, the graphene pore being in register with the hole in the SiN membrane. For sequencing of single stranded DNA molecules nanopores in the range of 1.1 to 1.5 nm in diameters may be suitable. For sequencing double stranded DNA, a suitable nanopore size is about 2.2 nm. The optimal diameters of the graphene nanopores are those that are only slightly larger than the cross sectional dimension of the biomolecule. In this case, the ratio of the blocked current due to biomolecule translocation to the open pore current is maximized. Graphene membranes may also feature pores in the range of from about 0.1 nm to about 100 nm.

One exemplary of such a configuration is shown in FIG. 45, which figure illustrates a hole in graphene on top of a hole in silicon nitride (Minimization of noise by having small areas of graphene). The noise can be reduced by lowering the capacitance of the device because the capacitance couples to the voltage noise of the power supply to produce electrical current noise, and therefore lower capacitance means lower current noise. This may be accomplished by (1) making the silicon nitride opening (pore) of relatively small such that the suspended graphene area is small and (2) by making the graphene sheet or flake relatively small, which may be accomplished by using a graphene piece that is only slightly larger than the pore formed in the silicon nitride. To produce a small graphene piece, a larger graphene sheet can be pre-patterned with lithography into a smaller area. An image of this is shown in FIG. 46, which figure shows a pore formed in a graphene-SiN assembly (left image), and a magnification of the pore formed in the graphene and SiN support.

FIG. 47 illustrates additional images. The left image in the figure illustrates a hole formed in a SiN membrane (hole formed by TEM); the right image in the figure illustrates a graphene pore in single layer graphene suspended on top of a ~20 nm large silicon nitride pore.

Coating graphene membranes with a thin insulating layer (in this case, $TiO_2$ layer) reduced current noise and provided a more hydrophilic surface, enabling a study of the dynamics of DNA translocation through these pores. Trends of the translocation velocity, current blockage and capture rate, as a function of applied bias voltage, agree with previous studies carried out with SiN nanopores. In addition to measuring ionic current through nanopores, below is described the use of graphene sheet conductivity to create devices for probing DNA molecules. Described are graphene-based nanopore devices that sense and control the electric potential locally at the nanopore and are capable of measuring transverse current across the pore aperture.

Suspended, TEM-compatible graphene layers can be controllably nanosculpted with nanometer precision by ablation via focused electron-beam irradiation in a TEM at room temperature. Presented is a transmission beam ablation lithography (TEBAL) method and have demonstrated graphene nanopores, nanobridges, and nanogaps, and other nanometer-scale patterns of arbitrary design that may prove useful in graphene-based electronic and mechanical applications. For instance, fabricating narrow constrictions in graphene layers is of interest for electronic property engineering. As one such example, graphene sheets and ribbons (longer than they are wide) may include a bow-tie, notch, triangle, carve-out, or other narrowed region or constriction (e.g., FIG. 66). Graphene nanostructures are mechanically robust and stable over time. The ability to introduce features into suspended graphene sheets by electron-beam-induced cutting and reshaping with high spatial resolution offers a route to fabricating graphitic structures for potential use in electrical, mechanical, and molecular translocation studies. Although some embodiments disclose graphene bodies (sheets, ribbons) separated from one another, graphene bodies may contact one another.

Graphene flakes are grown by chemical vapour deposition (CVD) of methane over polished copper foils. The copper foils are etched in solution so that bare graphene sheets, from single layers up to approximately 15 monolayers (~5 nm thick), float on the surface of the liquid. Suitably sized graphene sheets, larger than 2 mm×2 mm, are then scooped onto the prepatterned silicon nitride membranes. In this way the graphene is structurally supported by the nitride membrane, with only a limited area freely suspended over the ~10 nm to ~1 µm SiN hole. Graphene characterization is performed using optical, Raman, atomic-force and transmission electron microscopy. An exemplary TEM characterization of a single layer graphene pore is shown in FIG. 48. That figure shows that in a single layer graphene (SLG) diffraction pattern (DP) and the peak intensities are independent of tilt angle. Examples of DPs taken from graphene supported on a SiNx membrane. The DPs were taken from circular areas of ~1 micron in diameter. Further patterns are shown in FIG. 49, which figure shows a sample tilted 0, 5 and 10 degrees. The diffraction patterns (DPs) were taken from a circular area of roughly 1 micron in diameter, and the peak intensities did not change significantly with tilting, indicating a single layer graphene sample.

One may also perform measurements with nanopores made in exfoliated graphene in order to compare with the results obtained from CVD grown graphene. In this case, graphene flakes are exfoliated from graphite and transferred with micro-manipulators onto the substrate and above the hole in silicon nitride. Although nanopores drilled in exfoliated and CVD grown graphene seem structurally identical, CVD grown graphene may occasionally have lower electron mobilities and more impurities than exfoliated.

Electrical Measurements of Ion and Biomolecule Transport in a Fluid Cell

Electrical transport measurements are performed fluid cell setups. These setups feature multi-channel I-V measurements capability at high frequencies, with Heka and Axopatch 200B amplifiers, and variable temperature control in a fluid cell from 0° C. to room temperature using a thermoelectric device.

The measurement cell has microfluidic channels that form reservoirs in contact with either side of the chip. Using a pair of Ag/AgCl electrodes, a bias voltage, $V_B$, is applied between the two reservoirs to drive ionic current through the nanopore (see FIG. 2). The graphene nanopore chip may be connected to a PC-board so that it can be electrically contacted by external wiring, to control the potential on the graphene sheet. Alternatively, sharp microprobes with micromanipulators are used to contact the graphene sheet. This method does not require wire bonding to the PC board.

Scaling of the Ion Current ("Open Pore Current") with Nanopore Diameter and Thickness One question related to the ion flow through graphene pores is the scaling of the ion current with nanopore diameter, d. For truly 2d systems, the ion conductivity of a pore, G, of diameter d in an infinitely thin insulating membrane is G~d. On the other hand, if the pore is treated as a thin cylinder, $G\sim d^2$. Both dependencies have been reported recently for single-layer graphene nanopores. For example, nanopore drilling at room temperature in the TEM can create contamination at the nanopore edges, thus creating effectively thicker nanopores. One may realize both single-layer and multi-layer graphene nanopores and systematically vary d to determine G (d) for all these cases, and study the dependence of G on the number of graphene layers, N. One may also use TEM to precisely fabricate and measure the nanopore diameter and correlate it with the measured ion conductance, G. For these measurements, one may use 1M KCl solution and apply bias voltages up to 500 mV, a voltage regime where ion current scales linearly with voltage (FIG. 6). One may compute conductances using a model based on nanopore resistance (where nanopore is modeled as a cylinder) and access resistance (resistance of the electrolyte regions above and below the pore) that was found to give excellent fits for measurements in sub-10 nm thin silicon nitride nanopores.

Some have suggested that bare graphene nanopores do not wet completely but only partially (due to the hydrophobic nature of graphene) and that ions effectively flow through a pore of a smaller diameter. To explain the wetting properties and how ions flow through the pores, one may pretreat the graphene surface systematically with various physical or chemical treatments in order to tailor the composition of surface atoms and dangling bonds near the pore in the attempt to "regulate" the ion flow through them.

To quantitatively model this system, one may to consider the whole circuit diagram. In particular, in the regime of thin pores, nanopore resistance is minimized and the contributions from the access resistance, i.e. the resistance from the electrolyte to the nanopore, has to be taken into account in order to quantitatively explain the measured currents. In this case, the current is $I_{measured}=V/(2R_{access}+R_{pore})$, where $R_{access}$ is the access resistance and $R_{pore}$ is the resistance in the nanopore (FIG. 9). For very thin pores with thickness less than ~10 nm, the access resistance dominates and the maximum measured current may be limited by it.

Depending on the quality and size of the exposed area of the graphene sheet, it may also be possible to observe leakage currents through the graphene sheet that are larger than expected from the nanopore size. Extra leakage paths are possible through pinholes in the thin graphene sheet, especially when the suspended area is large. To investigate the presence and effects of potential pinholes on the ion current levels, one may measure the current for intact graphene sheets of varying area (before drilling a nanopore). If the pinhole density is constant across the sheet, one may observe that the leakage currents through an intact membrane scale with area. Also, to ultimately minimize any leakage current through pinholes, one may minimize the area of the suspended graphene sheet—this can be achieved by drilling the holes in the underlying SiN using focused ion beams, TEM or other means, in order to produce small SiN holes ~10-50 nm in diameter. FIG. 54 presents exemplary, non-limiting data concerning leakage currents after insulation.

Ion Current Stability and Noise Through Graphene Nanopores

The 1/f noise component for bare graphene devices extends to the 10 kHz frequency range with an exponent of 1, as compared with 10-100 Hz for silicon nitride pores. The low-frequency noise power, A, has been calculated for these traces using $S_I/<I>^2=A/f$, where $S_I$ is the current noise up to 5 kHz, <I> is the mean open pore current, and f is the frequency. In some cases, $A=7\times10^{-6}$ for bare graphene.

One may also control and lower the ion current noise, for example, by making the graphene surface more hydrophilic. Coating the graphene surface with a few-nm thin layer of $TiO_2$, one may observe lower noise, attributed to improved hydrophilicity of the $TiO_2$ surface. A non-limiting depiction of a coating pore is shown in FIG. 43, which figure illustrates coating graphene having coating present on the surface of the sheet as well as within the pore.

"Atomic engineering" of the graphene nanopore surface and geometry may also be used. The shape of the pore has previously been found to affect ion and DNA transport. For silicon nitride pores, for example, electron tomography showed that these pores have an hourglass shape with the narrow neck being ~⅓ of the total membrane height. To fit the measured open pore and blocked current values, these nanopores may be modeled as effective cylinders of the same diameter as the actual pore and a height that is equal to ⅓ of the membrane thickness. To obtain accurate fits of the measured currents, in the thin pore regime, the access resistance has to be included and one may assume that a negatively charged DNA polymer additionally expels a certain fraction of $Cl^-$ ions because of electrostatic repulsion in the pore. FIG. 17 is illustrative, as that figure shows TEM images of a nanopore formed in multilayer graphene.

Interactions of Graphene Nanopores and Biopolymers

Voltage Sensing on Graphene

Graphene is an excellent conductor and as such it permits sensing and control of the electric potential directly at the nanopore. Also, stacking graphene with insulator layers around the pore may allow control of the molecule's motion. One such exemplary embodiment is shown in FIG. 62. That figure shows a device featuring stacked graphene ribbons and an insulator. In that figure, a nanopore extends through a graphene-insulator-graphene stack, into and through a substrate. In this embodiment (non-limiting), the two graphene ribbons and the intermediate insulator are or approximately the same size such that there is little to no overhang between adjacent layers. Pores formed in stacked-layer devices are suitably of the same cross-sectional dimension through all layers of the device, although the cross-sectional dimension of the pore may be greater in one layer of a device than in others.

An alternative embodiment is shown in FIG. 63. Similar to FIG. 62, this embodiment shows a graphene-insulator-graphene stack. In FIG. 63, however, the bottommost graphene portion is a sheet having (in at least some parts) a cross-sectional dimension that is greater than the corresponding cross-sectional dimension of the graphene ribbon and the insulator. The nanopore extends through the stack and into and through the substrate. It should be noted that although nanopores are shown as being circular for purposes of illustration, nanopores need not actually be circular, and may instead be elliptical, triangular, slit-shaped, or otherwise irregular in shape. The nanopore suitably has at least one cross-section that is within 0.1, 1, 5, 10, or about 20 nm of a cross-sectional dimension of a macromolecule being analyzed.

One may employ a method to detect molecules based on measurements of the graphene voltage. This method consists of a nanopore that has been drilled directly through a graphene on top of a SiN sheet, permitting local voltage sensing and actuation at the nanopore. A TEM image of the proposed graphene nanoribbon/nanopore device is given in FIG. 18. A graphene sheet is positioned on top of a supporting SiN membrane and a nanopore is drilled directly through the sheet. DNA molecules are driven through the nanopore by applying a bias across the fluidic chambers. Electrical connections to the graphene sheet allow sheet voltage to be either measured or altered during DNA translocation. Due to the large in-plane conductivity of graphene, measurement or application of electronic signals at the nanopore site should be possible. Electrostatic perturbations induced by individual bases passing through a nanopore in the conductive sheet should alter the electric potential on the surface. With these devices one may slow translocating DNA molecules by locally gating ion flow through the nanopore. This will reduce measurement bandwidth and improve the signal to noise ratio, permitting faster measurement on individual molecules.

It should be understood that the devices and methods of the present disclosure do not require that the pore formed in the device extend exactly through both the graphene and the insulating material, as is shown in FIG. 21 (entire width of pore extending through graphene and through insulating material). FIG. 18 shows, as a non-limiting example, a pore that extends through the insulating material but does not extend through the graphene ribbon located atop the insulating material; i.e., the pore does not overlap the graphene. In this device, the pore is nearby to the graphene, but does not actually extend through the graphene.

FIG. 20 shows one alternative embodiment of the disclosed devices. That figure shows (panel c) a pore that extends through the insulating material nearby to the graphene. In other embodiments (not shown), a pore can be formed so as to straddle the graphene and the insulating layer; that is, some of the pore's diameter overlaps the graphene and some of the pore's diameter does not. As one such example, half of the pore's area may lie on the graphene, and the remainder of the pore's area may lie on the insulating material. Without being bound to any particular theory, having a pore that presents only some of its area to graphene may result in improved signal/noise performance for the devices. Embodiments where the pore is formed in the insulating layer nearby to the graphene may also exhibit useful performance, as the user may still monitor electrical readings from the graphene as a macromolecule translocates through the pore that is close to graphene.

Surface Treatments and Hydrophilicity of Graphene Nanopores

The edges of graphene ribbons are thought to significantly influence their chemical properties and reactivity and chemical functionalization approaches have been proposed. There is also a possibility for dangling bonds that may be considered. Chemical modification of various forms of graphene, including reduced graphene oxide and epitaxial graphene has been demonstrated. Coating of graphene nanopores with atomic-layer deposition oxide, leads to hydrophilic surfaces that increase the functional yield of graphene nanopore devices. One may also use UV/ozone exposure of the bare graphene membrane to make it more hydrophilic.

Further Disclosure

The present disclosure describes the improvement of the quality and performance of graphene nanopores for the detection, analysis and sequencing of biomolecules including DNA, proteins, microRNAs etc. The graphene sheet that contains one or more nanopores is current-annealed by running an electrical current through the conducting graphene-nanopore sheet.

By wiring the graphene-nanopore sheet with 2 or more terminals and by running electrical current though it, local heat is generated around the nanopores. This local heat causes several effects that all lead to the improvement of the quality and the ultimate performance of graphene nanopores for the detection and sequencing of biomolecules.

The current annealing may be used to 1) remove any adsorbates and other unwanted material from the surface of the graphene nanopore(s); 2) improve the quality of the graphene lattice in the vicinity of the nanopore and the nanopore edges; this includes the removal of any local defects in the graphene lattice and removal of any imperfections. This makes the nanopore walls and sides more atomically-perfect; 3) reduce the electrical noise in the measured ionic current that passes through the graphene nanopore when the device is assembled into a fluidic cell; 4) reduce the electrical noise in the measured electrical current measured through the graphene layer(s); the graphene layer(s) can be patterned to contain a nanopore and can be shaped as a nanoribbon, nanoconstriction or other shapes. The electrical noise measured through this nanoribbon containing a nanopore is reduced after current-annealing; 5) Increase of the signal-to-noise ratio measured in the ionic current as the biomolecule passes through the nanopore; 6) Increase of the signal-to-noise ratio measured in the current through the graphene sheet or nanoribbon, measured as the biomolecule passes through the nanopore; 7) More easily detect and analyze biomolecules with graphene nanopores that have been current-annealed, as opposed to those nanopores that have not been current-annealed; and 8) More easily sequence biomolecules, including obtaining the DNA sequence, with current-annealed nanopores, as opposed to those nanopores that have not been current-annealed.

FIG. 19 illustrates an example device containing a graphene sheet shaped in form of a nanoribbon with a nanopore drilled in the nanoribbon. Ionic current, $I_m$, is measured with macroelectrodes. The current through the graphene sheet/nanoribbon is $I_n$. Measurements of both currents, $I_m$ and $I_n$, as a function of time, as the biomolecules (DNA) traverse the pore can be used to detect and analyze (sequence) the molecule. Current-annealed nanopores in sheets/nanoribbons are considered especially sensitive for the detection of biomolecules than nanopore that have not been current-annealed, and such current-annealed nanopores lead to improved signal-to-noise ratio for biomolecule detection.

FIG. 20 illustrates examples of fabricated graphene nanoribbons with nanopores in the middle or sides of the nanoribbon. Additional graphene gates near the nanoribbon are also fabricated.

FIG. 21 presents another TEM image of the graphene nanoribbon with a nanopore drilled in it, fabricated between two gold electrodes, on top of a silicon nitride substrate. FIG. 22 illustrates an exemplary fluidic cell made to accommodate the graphene nanopore/nanoribbon/nanosheet device between metal electrodes. The metal electrodes are used to connect to the graphene sheet/nanoribbon and to run electrical current through it. This electrical current can heat the graphene nanopore locally and this process can result in an improved nanopore and hence, improved device performance for the purpose of detecting and analyzing/sequencing biomolecules, in particular, DNA and proteins. An optical image of this system is present in FIG. 23.

FIG. 24 illustrates measured graphene nanoribbon conductance as a function of nanoribbon width. A cartoon of the graphene nanoribbon device with a nanopore is included as FIG. 25. Although this graph shows nanoribbons with relatively large width (~100 nm), graphene ribbons were made and down to ~1 nm width. The resistances of these narrow ribbons are in the kOhm range and these ribbons can sustain extremely large current densities (which is important for increasing the electrical signal for DNA sequencing). Ribbon resistance may be in the range of from about 10 Ohms to about 25 kOhms.

FIG. 26 is a photograph of a micromanipulator setup to electrically contact the graphene nanopore sheet and measure the ionic current and the current through the graphene is included.

FIG. 27 presents a measurement of the electrical noise (power spectral density vs. frequency) of the ionic current through the graphene nanopore measured in the exemplary setup described above. FIG. 28 presents a SEM image of a hole in the silicon nitride membrane between metal electrodes.

A graphene sheet is suspended on top of this hole and shaped in form of a ribbon. (see TEM image in FIG. 29); black is the metal, darker grey is silicon nitride, light grey is graphene). A nanopore can be drilled in such a nanoribbon. Such suspended graphene ribbons can be studied inside of a transmission electron microscope to observe the effects of current-annealing on the nanopores. The current-annealing is performed by applying voltage between the metal electrodes while measuring the current through the graphene-nanopore sheet. The measured resistance of the sheet decreases during this current-annealing process.

The structure of the nanopores changes and the graphene lattice around the nanopore becomes cleaner and more pronounced. Instead of observing only circular terraces around the nanopore, these terraces morph into more hexagonal shapes and one observes more atomic arrangements at 60 and 120 degree angles that reflect a more perfect lattice. In addition, defects, impurities and junk on top of the graphene nanopore surface are being removed. This current-annealing process is performed in vacuum or some inert/non-interacting atmosphere (e.g. forming gas, nitrogen gas, etc.).

FIGS. 30A and 30B, respectively, present the same graphene nanopore imaged with TEM before and after current-annealing.

FIG. 31 presents current vs. voltage through the graphene nanopore nanoribbon showing how (FIG. 32) resistance decreases during current-annealing. Without being bound to any single theory, the reduced resistance remains permanent when the sample is kept in inert conditions.

FIG. 33 presents a possible graphene nanopore device geometry involves adding additional side gates near the current-annealed nanopore and nanoribbon. FIG. 34 presents an image of a silicon nitride chip used with fabricated metal electrodes. The graphene sheet is deposited on top of the metal pattern. The window in the middle has a hole on top of which graphene is suspended and nanopores are drilled into the graphene sheet with TEM beam.

FIG. 35 presents current vs. voltage through the suspended graphene nanopore sheet. When the voltage is held constant for some time (for example at 1.6 V), the current through the graphene nanopore sheet further increases in time (meaning that the resistance decreases, as a consequence of current-annealing). This process leads to the cleaning and improvement of the graphene nanopore surface. The same effect can be achieved by thermal heating.

FIGS. 36A and 36B present Ionic current vs. voltage (36A) when the device is assembled into the fluid cell and one is measuring the ionic current passing through the pore. The ionic current noise (36B) (lower curve) after current-annealing is lower than before current-annealing (blue curve on the right). This means that current-annealed nanopores may be less electrically noise and more sensitive for the detection and analysis/sequencing of biomolecules. This is particularly useful for their use in DNA sequencing applications. In addition, the current through graphene nanoribbons that are current annealed is less noisy and current-annealed graphene nanoribbons may be more sensitive for the detection and analysis/sequencing of biomolecules.

Further information concerning current-annealing may be found in Lu, et al., "In Situ Electronic Characterization of Graphene Nanoconstrictions Fabricated in a Transmission Electron Microscope," *Nano Lett.*, 2011, 11 (12), pp 5184-5188, incorporated herein by reference for any and all purposes. Again, without being bound to any particular theory, heating of a graphene sample to ~300-400° C. may remove (e.g., via vaporization) residue from the lithography processes and result in an associated increase in carrier mobility. This temperature range is consistent with an applied voltage of 2.3V. Images of few-layer graphene (FLG) nanoribbons taken before and after annealing indicate contamination removal as impurities evaporate from the surface. High-temperature annealing (described elsewhere herein) reduces the contact resistance between metal electrodes and carbon nanomaterials, such as graphene. High-temperature current annealing also induces structural reconfiguration and recrystallization of the FLG ribbon. Current annealing thus improves the structural and electronic properties of the CVD graphene.

It should be understood that current-annealing is not the sole process by which one may effect annealing on graphene, and other processes may be applied. As one example, a user may apply heat-annealing to graphene. Without being bound to any particular theory, annealing decreases adhesion between macromolecules (e.g., DNA) and the various components (metal contacts, insulators and other layers) that may be present in a device, thus allowing molecules to more easily translocate through the nanopores.

A user may heat graphene, treat the graphene with a plasma (e.g., $O_2$ plasma), and even UV radiation. These techniques act to remove organic materials, carbon, and other contaminants from around the nanopore region. Without being bound to any particular theory, treating the pore with plasma acts to clean the pore and also render the pore at least partially hydrophilic.

Heating may be at a temperature of 200, 250, 300, 350, 400, 450, or even 500 degrees C. The heating may be performed in an inert atmosphere, but may also be performed in forming gas, nitrogen gas, air or other ambient atmospheres. The heating may be performed for 1-60 seconds, or even for 1, 5, 10, 20, 25, 45, 50, or more than 60 minutes. The heating can also be performed over many ours, for example, overnight. The heating may be performed at a single temperature or at two or more temperatures.

One exemplary routine is described as follows. First, graphene deposited on a SiN membrane is heated; the graphene may be grown by CVD, epitaxial methods, or by other methods. After graphene nanoribbons are patterned by electron beam lithography or other methods, the nanoribbons may be cleaned with an $O_2$ plasma, at, e.g., 5 minute exposure at 50 W. The user may also perform a thermal annealing (at, e.g., 350 degrees C. for about 20 minutes) step. The user may then also apply a UV-ozone treatment. This may be performed for a time (e.g., 5, 10, 15, 20, 25, 30, 45 minutes) on each side of the graphene material.

After deposition of an insulating layer (e.g., appx. 20 nm thick), a user may apply further thermal annealing (e.g., at 350 degrees C.) to improve the crystallinity of dielectric layer and the graphene, and also to re-clean the graphene. After the user forms one or more pores in the graphene, the user may apply further thermal annealing (e.g., at from about 150 deg C. to about 500 deg C. or even about 2000 deg. C.). The user may also apply a UV-ozone treatment, e.g., for 20 minutes each side, at around 150 degrees C. Annealing may be performed on graphene or even devices that do not have pores formed therein.

It is not necessary that all of the foregoing steps be performed. For example, it may be sufficient to heat the sample only once at this elevated temperature to produce the desired effect. However, heating/cleaning several times may result in improved sample conditions and sample yield, as well as removing dirt that has been accumulated by exposing the sample to the environment. Heating and cleaning a sample several times (between processing steps) may enhance device yield and device performance. The foregoing steps may be performed in a vacuum.

The present disclosure also provides methods of protecting graphene nanoribbon devices from electrical events, such as short-outs. In some of the disclosed devices, graphene nanoribbons are fabricated near a nanopore to serve as electrical sensors for single-DNA basis. To electrically contact graphene nanoribbons, the user connects the nanoribbon to external wiring. This is achieved by fabricating larger metal pads that are then connected to macro-wires. But because of their small size (e.g., less than 100 nm in width), the graphene nanoribbons are electrically very sensitive, and if charged by external conditions, they can in some cases be damaged and may even damage the membrane that underlies the graphene.

To increase device yield and guard against electrical damage, the present disclosure also presents methods to protect graphene ribbon by connecting it to another piece of metal that forms a closed circuit and that can withstand the discharge and short the circuit to prevent the graphene ribbon damage.

This metal protection is cut and removed prior to the DNA translocation measurement (for example, by scratching it off the chip). However, it protects the graphene ribbon during the course of fabrication up until the time that the ribbon is inserted into a fluidic cell for a measurement.

The present disclosure thus provides methods for constructing a device having improved durability and signal-to-noise characteristics. These methods suitably include applying, to a graphene sheet that places two or more electrical leads into electronic contact with one another one or more of thermal annealing, current annealing, a plasma, ozone, or any combination thereof. The graphene sheet may, as described elsewhere herein, comprise a nanopore extending therethrough or nearby. The graphene sheet may have an area of less than about 31400 $nm^2$.

One exemplary embodiment is shown in FIG. 37, which figure illustrates a chip containing a single graphene nanoribbon that is in electronic communication with anti-static discharge strips. FIG. 38 presents an alternative embodiment in which three graphene ribbons are in electronic communication with multiple anti-static discharge strips that connect contact pads but are themselves cut or otherwise removed before the device is used in measurement. The connections between the graphene and the pads are suitably of a metal, e.g., copper, gold, and the like. The connections are, as described elsewhere herein, removed or cut before the device is operated. When in place, the connections act to combat the buildup of static charge.

FIG. 39 presents two views of a graphene ribbon device according to the present disclosure. In one view (upper left portion of figure) is shown a graphene ribbon with tapered ends (scale bar=1 micrometer). In a second view (lower right) is shown a graphene ribbon in electronic contact with two metal contacts. FIG. 40 presents another alternative view of devices according to the present disclosure, with the figure showing a graphene ribbon positioned between two metal contacts. FIG. 57 shows another, alternative embodiment with a graphene ribbon (having a tapered region) formed thereon. A pore (not shown) may be formed in a narrowed region of the graphene. The side gate can be made of graphene, used to modulate the conductance of the graphene ribbon to maximize its sensitivity to biomolecules.

FIG. 57 also illustrates an embodiment of the disclosed devices that features a side gate embodiment. The grey triangle on the right of the image ("graphene gate") is formed from of patterned graphene. The gate may be used to apply voltage so as to affect the conductance of the ribbon (e.g., to place the ribbon at a conductance level that is sensitive to the passage of DNA bases). Another related figure is FIG. 33. That figure illustrates—using VG1 and VG2—are voltages applied to side gates on opposite sides of a graphene ribbon. The gates shown in FIG. 33 are rectangular in conformation, and the gate in FIG. 57 presents a more triangular profile.

FIG. 41 shows a device according to the present disclosure, held by a pair of tweezers. As shown in the figure, the device includes several graphene sheets that are in turn in contact with metal contacts. A graphene gate may be present at the side of the device (as shown in the figure), but may also be formed in a plane below the ribbon, or even separated by the ribbon with an insulator.

The graphene ribbon is contacted electrically with metal contact pads. To prevent electrostatic discharge, which can destroy the device, one may connect the metal contact pads that contact each side of the ribbon with a metal strip. This connector ensures that each side of the ribbon is held at the same potential, thereby reducing charging of one side of the ribbon which would create an unequal potential and can lead in electrostatic discharge. This anti-blow-up strip is incorporated into the contact pad design so that one may can prevent electrostatic discharge from the very start of device fabrication. When one performs a measurement using the graphene ribbon, one may cut the anti-blow-up strip so that one may apply the desired potential to either side of the ribbon.

An exemplary fabrication method is shown in FIG. 51. As shown in that figure, a device may be fabricated by patterning metal wires or other structures on a substrate, such as an insulating material. A graphene piece may be deposited and patterned so as to place graphene in the desired locations, followed by deposition of an insulator, exposing contacts, and forming the pore. The foregoing steps need not necessarily be performed in the foregoing order. In another embodiment, device fabrication proceeds in the following steps: 1) graphene deposition on silicon nitride chips, 2) patterning of nanoscale metal contacts with e-beam lithography, 3) patterning of larger metal contacts with optical lithography, 4) patterning of graphene with electron beam lithography followed by etching to define nanoribbons, 5) deposition of an insulating layer on top of the whole chip to prevent electrochemistry between graphene and metal surfaces and solution, and 6) removal of certain areas of the insulator in order to expose larger metal contacts used to connect the ribbon to external circuitry.

Additional Disclosure

Graphene Fabrication

Graphene may be grown in a CVD furnace on copper foils. The copper foil is then etched away, leaving the suspended graphene that is transferred on silicon nitride chips. Graphene can be exfoliated from graphite, or graphene can be grown. One may use CVD (chemical vapor deposition) growth methods for growing single-layer and more-than-one-layer graphene samples.

Controlling the temperature and time used during graphene production can be used to control the number of atomic layers in the graphene. For multilayer graphene, one may grow from between about 2 and about 15 layers. Once the graphene is grown (single or multilayer), the copper foil is then etched away, leaving the suspended graphene that is transferred on silicon nitride chips.

Device performance may be affected by a number of layers. For example, bilayer graphene under electric fields has a bandgap that may be especially sensitive to DNA translocation. The structure of graphene nanopores may depend on the number of layers. For graphene nanopores in single graphene layers, atomic bonds at the graphene nanopore edge will be dangling and may be passivated. Passivation may be accomplished by atomic species like H, N, OH etc. For graphene nanopores in 2, 3 or more layers, there may be interlayer bonding so that the two nearby graphene layers may attach and form a closed edge, leaving no dangling bonds.

Surface Treatment of Devices

Because carbon reacts with DNA, one may desire to use cleaning and coating methods. Graphene nanopores may be coated with inorganic or organic materials to render them hydrophilic and prevent undesired sticking of DNA to the pores. Coatings can include insulators that are deposited with standard cleanroom procedures, or could include chemistry methods to deposit molecules on the graphene surface. These molecules include organic molecules (such as proteins, DNA etc.) or inorganic molecules (self-assembled monolayers, and the like). A user may fabricate nanopores inside the nanoribbons, but a user may also fabricate nanopores at the edges of the nanoribbons. Nanopores may range in size from ~1.1 to 4 nm. The small diameter pores pores (~1.1 to 2 nm) be suitable for single stranded DNA sequencing, while larger diameter pores (~2.2 to 3) will be suitable for double strand DNA sequencing. An exemplary row of nanopores is shown in FIG. 58, which figure presents a TEM image of an array of nanopores drilled in order of increasing diameter from ~2 nm to ~8 nm.

Graphene nanoribbon (GNR) width may be in the range of 1 nm-100 nm. The nanoribbon width down to ~10-15 nm can be produced by using electron beam lithography methods. The nanoribbon width can be further decreased below ~10 nm by electron beam sculpting inside the TEM. Material characterization of the fabricated nanoribbon devices was performed using Raman spectroscopy, Electron energy loss spectroscopy (EELS), and dark field TEM imaging and electron diffraction. Dark field TEM imaging and electron diffraction pattern obtained from the ribbon are shown in FIG. 53. In that example, a GNR (100 nm width) made on top of a SiNx window (50 nm thick) is covered by 20 nm of amorphous SiOx and 20 nm of Al2O3. The line scan taken from the line highlighted with dashed line shows that the ribbon has an excess mass of roughly 30% at the edges. This unexpected result, a consequence of the nanofabrication process, may assist in identifying a suitable region for nanopore drilling.

Graphene ribbons may have a cross-sectional dimension (e.g., width) in the range of from about 1 nm to about 500 nm, or from about 49 nm to about 251 nm, or from about 97 nm to about 187 nm, and any and all ranges therebetween. Ribbons having a cross-sectional dimension in the range of from about 1 nm up to about 25 nm are considered particularly suitable. 25 nm to 1 nm and one may go below 10 nm in single nm to achieve the desired sensitivity (for example ribbon that is 4 nm wide and pore that is 1.2 nm in diameter inside of it). A ribbon may have a cross-sectional dimension (e.g., length) in the range of from about 0.1 micrometer to about 10, 20, 50, 100, 500, or even 1000 micrometers; ribbons having a length of from about 100 nm to about 500 micrometers are considered especially suitable.

FIG. 59 presents an exemplary electron diffraction pattern collected from the graphene nanoribbon showing a characteristic hexagonal pattern for graphene (left image). When a dark field TEM image is constructed from electrons in the 1210 spot that have diffracted from graphene, one may see that the graphene is present only in the ribbon geometry and not anywhere else, validating the graphene etching and ribbon fabrication procedure.

The relative presence of different chemical elements can be determined by performing Electron Energy Loss spectra (with nanometer spatial resolution) in STEM mode. In this example, EEL spectra were acquired for 20 points along the dashed line. Peaks for N and O (401 and 532 eV, respectably) are observed in the spectrum (right). In this way, the mass concentration (atoms/$nm^2$) of the different elements is estimated along the line. This example (top) shows that O content increases with respect to N at the GNR, as expected, since silica and aluminum oxide were deposited on top of the graphene. EELS characterization with nm-resolution confirmed the presence of expected elements (O, N, Si, C) and their relative ratio is different when imaging the surface above the nanoribbon and above the nearby substrate, as expected. An exemplary EEL spectrum (with nm spatial resolution) is shown in FIG. 52.

Samples featuring a pore drilled directly through the ribbon and samples featuring a pore located outside of the ribbon but close to it may be fabricated. In both cases, DNA will interact electrostatically with the graphene nanoribbon and perturbs the nanoribbon conductance. The nanopore may be drilled at a position in the ribbon such that the nanoribbon conductance modulation will be the biggest when the DNA bases pass near the ribbon.

Depending on the nanoribbon atomic and edge structure, different positions of the nanopore may be useful. For example, if a nanopore is drilled in the middle of the ribbon, the sensitivity to DNA may be maximized. However, the nanopore can be drilled at any position in the ribbon. For example, nanopores can be drilled inside or just next to the ribbon. It is possible that in some instances it is optimal to drill the nanopore near the edge of the ribbon, within the ribbon, or just outside of the ribbon. The nanopore can also be drilled at the very edge of the ribbon, such that the nanopore structure has graphene on one side of it and no graphene on the other side of it. If the graphene nanoribbon carries electrical current through the edges, then ribbons may be sensitive if the nanopore is just at the edge of the ribbon. One exemplary embodiment is shown in FIG. 64, which figure illustrates a pore formed at a distance from the edge of a graphene nanoribbon. The distance between the edge of the graphene ribbon or sheet and the edge of the pore may be in the range of from about 0.1 nm to about 500 or even about 1000 nm, and all intermediate values. FIG. 65 illustrates various embodiments of the disclosed devices, which embodiments illustrate that the pore may reside entirely within a graphene sheet or ribbon, entirely outside the graphene sheet or nanoribbon, or partially within the graphene sheet or nanoribbon. Embodiments where 0.1, 1, 5, 10, 20, 50, or even about 75% of the area of a pore resides within the graphene ribbon or sheet are all considered suitable.

FIG. 66 presents further alternative embodiments of the disclosed devices. As shown in that figure, pores may be formed in or nearby to graphene ribbons of various shapes, including ribbons having a notch or other feature formed therein. The image at the far right of the figure shows a graphene ribbon having an aperture formed therein, with a nanopore residing within the aperture and extending into the substrate beneath the graphene ribbon.

Ion current is used to detect DNA passage through the pore. An example of ionic translocations through a nanoribbon-nanopore device are shown in FIG. 60. In this case, the nanopore is drilled through the insulated graphene nanoribbon on top of the silicon nitride chip, and therefore the nanopore itself consists of the following layers: insulator-graphene-silicon nitride.

Nanopore chip cleaning was useful, and such cleaning was performed—as explained elsewhere herein—using a combination of heating, plasma cleaning and UV/ozone cleaning. Heating of the ribbon is important because it cleans the surface from residues, it improves the electrical quality of the graphene by improving its structure, and it also lowers the contact resistance.

To examine conducting nanoribbons, TEM measurements of nanoribbon conductance while measuring the nanoribbon width were performed by making a 100 nm-wide ribbon and measuring its conductance inside the TEM. While running electrical current through the nanoribbon to heat the ribbon (current annealing), the nanoribbon resistance decreased. This was due to a combination of three factors: removal of resist residue and contamination, improved electrical contacts to the ribbon and graphene lattice recrystallization. Ribbon width was trimmed by cutting it from the side with a highly focused electron beam from the TEM. Nanoribbons down to 1 nm in width were made using this procedure. Ribbon conductance scaled as $w^{0.75}$, where w is the ribbon width.

A DNA base traverses the nanopore over about 100 ns. This means that the frequency of the electronics used to detect the electrical signal from each base may be about $\frac{1}{100}$ ns=10 MHz. In order to detect DNA bases translocating through the pore, the electronics are suitably of about 10 MHz or faster. An alternative approach is to slow down the DNA itself. This approach, however, is somewhat contrary to the goal of rapid DNA sequencing.

Because the electrical signal from the nanoribbons is large enough (they can easily withstand microAmps up to miliAmps of current), nanoribbons allow detection at fast frequencies, and allow DNA base sequencing without slowing down the DNA molecules. One may set up a high-bandwidth current measurement setup and the fast data acquisition setup. The amplifier and data acquisition card may operate up to 200 MHz bandwidth, above the 10 MHz bandwidth detection limit. As part of this fast measurement setup, one may include a fast computer for data acquisition and analysis as streams of data may contain a large number of points. One exemplary setup is shown in FIG. 61.

The present disclosure also provides devices. These devices suitably include a first graphene sheet contacting an insulating membrane, a pore extending through the insulating membrane, the pore having a characteristic cross-sectional dimension in the range of from about 0.1 nm to about 100 nm. At least a portion of the pore may extend through the graphene sheet. An edge of the pore may be within 50 nm of an edge of the graphene sheet. The area of the graphene sheet that overlies the pore may, in some embodiments, be less than about 31400 $nm^2$. The area of the graphene sheet that overlies the pore is suitably less than about 314 $nm^2$. The area of the graphene sheet itself may be less than about 31400 $nm^2$, or even less than about 314 $nm^2$.

Also provided are methods of fabricating devices. These methods suitably include placing a graphene sheet that contacts an insulating membrane into electrical communication with a segment of conductive material, the segment of conductive material being in electrical communication with first and second contact pads, the graphene sheet being in electrical communication with the first and second contact electrodes.

Further disclosed are devices. The devices suitably include a first graphene body; a membrane contacting the first graphene body, the membrane having an aperture formed therethrough, the aperture having a characteristic cross-sectional dimension in the range of from about 1 nm to about 1000 nm.

The first graphene body may include at least one pore extending at least partially therethrough, the pore being in register with the aperture of the membrane. The pore may have a cross-sectional dimension in the range of from about 0.1 nm to about 500 nm.

In some embodiments (e.g., FIG. 64), an edge of the first graphene body is within 1000 nm of an edge of the aperture of the membrane. The first graphene body may, in some cases, be characterized as being a ribbon.

The devices may also include a second graphene body. An edge of the second graphene body is within 1000 nm of an edge of the aperture of the membrane. At least a portion of the second graphene body may overlap at least a portion of the first graphene body. The first and second graphene bodies may contact each other, but may also be separated from one another (e.g., FIG. 63). The second graphene body may be characterized as being a ribbon. The second graphene body may, in some embodiments, include a pore that is in register with a pore in the first graphene body, in register with an aperture formed in the membrane, or both.

REFERENCES

The following references are incorporated herein in their entireties for any and all purposes.

1. M. Rhee; M. A. Burns *Trends Biotech* 2006, 24, 580.
2. K. Healy; B. Schiedt; A. P. Morrison *Nanomedicine* 2007, 2, 875.
3. C. Dekker *Nat Nanotechnol* 2007 2, 209.
4. D. Branton; D. W. Deamer; A. Marziali; H. Bayley; S. A. Benner; T. Butler; M. Di Ventra; S. Garaj; A. Hibbs; X. Huang; S. B. Jovanovich; P. S. Krstic; S. Lindsay; X. S. Ling; C. H. Mastrangelo; A. Meller; J. S. Oliver; Y. V. Pershin; J. M. Ramsey; R. Riehn; G. V. Soni; V. Tabard-Cossa; M. Wanunu; M. Wiggin; J. A. Schloss *Nat Biotechnol* 2008, 10, 1146.
5. Wanunu M., Soni G. V., Meller A. (2009) in *Springer Handbook of Single-Molecule Biophysics* (ed. A. Van Oijen), Springer Publishing, New York.
6. L.-Q. Gu; J. W. Shim *Analyst* 2010, 135, 441.
7. Z. S. Siwy, S. Howorka, *Chem Soc Rev,* 2010, 39, 1115-1132
8. A. Meller; D. Branton *Electrophoresis* 2002, 23, 2563.
9. J. J. Kasianowicz; E. Brandin; D. Branton; D. W. Deamer *Proc Nat Acad Sci* 1996, 93, 13770.
10. Y. Astier; O. Braha; H. Bayley *J Am Chem Soc* 2006, 128, 1705.
11. J. Clarke; H.-C. Wu; L. Jayasinghe; A. Patel; S. Reid; H. Bayley *Nature Nano* 2009, 4, 265.
12. M. Zwolak; M. Di Ventra *Nano Lett* 2005, 5, 421.
13. H. W. Ch. Postma *Nano Lett.,* 2010, 10, 420.
14. J. Li; D. Stein; C. McMullan; D. Branton; M. J. Aziz; J. A. Golovchenko *Nature* 2001, 412, 166.
15. B. M. Venkatesan; A. B. Shah; J.-M. Zuo; R. Bashir *Adv Func Mat* 2010, 20 1616.
16. A. J. Storm; J. H. Chen; X. S. Ling; H. W. Zandbergen; C. Dekker *Nat Mater* 2003, 2, 537.
17. K. S. Novoselov; A. K. Geim; S. V. Morozov; D. Jiang; Y. Zhang; S. V. Dubonos; I. V. Grigorieva; A. A. Firsov *Science* 2004, 306, 666.
18. M. Y. Han; B. Özyilmaz; Y. Zhang; P. Kim *Phys Rev Lett* 2007, 98, 206805.
19. S. Cho; Y.-F. Chen; M. S. Fuhrer *Appl Phys Lett* 2007, 91, 123105.
20. J. C. Meyer; A. K. Geim; M. I. Katsnelson; K. S. Novoselov; T. J. Booth; S. Roth *Nature* 2007, 446, 60.
21. M. D. Fischbein; M. Drndić *Appl Phys Lett* 2008, 93, 113107.
22. M. E. Gracheva; D. V. Melnikov; J.-P. Leburton *ACS Nano* 2008, 2, 2349.
23. M. E. Gracheva; J. Vidal; J.-P. Leburton *Nano Lett* 2007, 7, 1717.
24. X. Li; W. Cai; J. An; S. Kim; J. Nah; D. Yang; R. Piner; A. Velamakanni; I. Jung; E. Tutuc; S. K. Banerjee; L. Colombo; R. S. Ruoff *Science* 2009, 324, 1312.
25. M. D. Fischbein; M. Drndić *Nano Lett* 2007, 7, 1329.

26. S. Wang; http://pubs.acs.org/doi/abs/10.1021/1a901402f-aff1 Y. Zhang http://pubs.acs.org/doi/abs/10.1021/1a901402f-aff1; N. Abidi; http://pubs.acs.org/doi/abs/10.1021/1a901402f-aff2L. Cabrales *Langmuir* 2009, 25, 11078.
27. Z. Liu; K. Suenaga; P. J. F. Harris; S. Iijima *Phys Rev Lett* 2009, 102, 015501.
28. J. M. Simmons; B. M. Nichols; S. E. Baker; M. S. Marcus; O. M. Castellini; C.-S. Lee; R. J. Hamers; M. A. Eriksson *J Phys Chem B* 2006, 110, 7113.
29 A. Hashimoto; K. Suenaga; A. Gloter; K. Urita; S. Iijima *Nature* 2004, 430, 870.
30. K. S. Kim; Y. Zhao; H. Jang; S. Y. Lee; J. M. Kim; K. S. Kim; J.-H. Ahn; P. Kim; J.-Y. Choi; B. H. Hong *Nature* 2009, 457, 706.
31. M. Wanunu; J. Sutin; B. McNally; A. Chow; A. Meller *Biophys Journal* 2008, 95, 4716.
32. J. Li; M. Gershow; D. Stein; E. Brandin; J. A. Golovchenko *Nat Mater* 2003, 2, 611.
33. J. Aarik; A. Aidla; T. Uustare; K. Kukli; V. Sammelselg; M. Ritala; M. Leskelä *Appl Surf Sci* 2002, 193, 277.
34. R. Wang; K. Hashimoto; A. Fujishima; M. Chikuni; E. Kojima; A. Kitamura; M. Shimohigoshi; T. Watanabe *Nature* 1997, 388, 431.
35. Y. Zhang; H. Dai *Appl Phys Lett* 2000, 77, 3015.
36. P. Chen; T. Mitsui; D. B. Farmer; J. Golovchenko; R. G. Gordon; D. Branton *Nano Lett* 2004, 7, 1333.
37. B. M. Venkatesan; B. Dorvel; S. Yemenicioglu; N. Watkins; I. Petrov; R. Bashir *Adv Mater* 2009, 21, 2771.
38 R. M. M. Smeets; U. F. Keyser; M. Y. Wu; N. H. Dekker; C. Dekker *Phys Rev Lett* 2006, 97, 088101.
39. A. J. Storm; J. H. Chen; H. W. Zandbergen; C. Dekker *Phys Rev E* 2005, 71, 051903.
40. G. M. Skinner; M. van den Hout; O. Broekmans; C. Dekker; N. H. Dekker *Nano Lett* 2009, 9, 2953.
41. P. Chen; J. Gu; E. Brandin; Y.-R. Kim; Q. Wang; D. Branton *Nano Lett* 2004, 4, 2293.
42. Merchant, C. A.; Healy, K.; Wanunu, M.; Ray, V.; Peterman, N.; Bartel, J.; Fischbein, M. D.; Venta, K.; Luo, Z.; Johnson, A. T. C.; Drndic', M. Nano Lett. 2010, 10, 2915-2921.
43. Schneider, G. F.; Kowalczyk, S. W.; Calado, V. E.; Pandraud, G.; Zandbergen, H. W.; Vandersypen, L. M. K.; Dekker, C. Nano Lett. 2010, 10, 3163-3167.
44. Garaj, S.; Hubbard, W.; Reina, A.; Kong, J.; Branton, D.; Golovchenko, J. A. Nature 2010, 467, 190-193.

What is claimed:

1. A device, comprising:
   a first graphene sheet being characterized as having a bowtie profile and having a narrowed region that defines a width in a direction,
     the narrowed region bridging first and second regions of the first graphene sheet, each of the first and second regions defining a width in the direction that is greater than the width of the narrowed region in the direction, the narrowed region having a thickness and further comprising at least one pore extending through the thickness of the narrowed region, the pore being contained within the narrowed region,
     the pore characterized by a cross-sectional dimension in the range of from about 0.1 nm to about 100 nm, the cross-sectional dimension of the pore being less than the width of the narrowed region; and
   a membrane contacting the first graphene sheet,
     the membrane having an aperture in register with the pore of the first graphene sheet.

2. The device of claim 1, wherein the graphene sheet has an area of less than about 31400 nm2.
3. The device of claim 1, further comprising a graphene ribbon contacting the first graphene sheet.
4. The device of claim 1, further comprising a second graphene sheet, the first and second graphene sheets at least partially overlapping one another.
5. The device of claim 1, wherein the aperture has a cross-sectional dimension in the range of from about 10 nm to about 30 nm.
6. The device of claim 5, wherein the pore has a cross-sectional dimension in the range of from about 1 nm to about 10 nm.
7. The device of claim 6, wherein the cross-sectional dimension of the aperture differs from the cross-sectional dimension of the pore by less than about 5 nm.
8. The device of claim 1, wherein the first graphene sheet has a cross-sectional dimension that is larger than a cross-sectional dimension of the aperture by less than about 20 nm.
9. The device of claim 1, wherein the first graphene sheet has a cross-sectional dimension that is larger than a cross-sectional dimension of the aperture by less than about 10 nm.
10. The device of claim 1, wherein the first graphene sheet comprises from 1 to about 50 layers of graphene.
11. The device of claim 1, wherein the membrane comprises silicon nitride, silicon oxide, boron nitride, aluminum oxide, hafnium oxide, borosilicate glass, quartz, or any combination thereof.
12. The device of claim 1, further comprising a voltage source capable of applying a voltage across the pore of the first graphene sheet.
13. The device of claim 1, further comprising a current amplifier capable of measuring the ionic current flowing through the pore in the first graphene sheet.
14. The device of claim 1, further comprising a voltage sensor capable of measuring the voltage on the first graphene sheet.
15. The device of claim 1, further comprising a first amount of an insulating material surmounting at least a portion of the first graphene sheet, through which insulating material the pore of the first graphene sheet extends.
16. The device of claim 15, wherein the insulating material has a thickness in the range of from about 0.1 nm to about 100 nm.
17. The device of claim 15, wherein at least a portion of an interior wall of the pore of the graphene sheet is surmounted by the insulating material.
18. The device of claim 15, wherein the insulating material is disposed between the first graphene sheet and a second graphene sheet, the second graphene sheet comprising a pore at least partially in register with the pore of the first graphene sheet.
19. The device of claim 4, wherein the first and second graphene sheets are characterized as being ribbons.
20. The device of claim 19, wherein the ribbons overlap one another.
21. The device of claim 20, wherein the ribbons are characterized as being crossed.
22. The device of claim 1, wherein at least a portion of the graphene sheet comprises graphene annealed by application of an electric current, graphene annealed by application of thermal annealing, graphene that has been exposed to a plasma, graphene that has been exposed to ozone, or any combination thereof.

23. The device of claim 1, wherein the graphene sheet has a resistivity in the range of from about 1 k-ohms to about 2 M-ohms.

* * * * *